(12) United States Patent
Warren et al.

(10) Patent No.: US 10,413,334 B2
(45) Date of Patent: Sep. 17, 2019

(54) METHOD AND APPARATUS FOR SPONDYLOLYSIS REPAIR

(71) Applicant: DePuy Synthes Products, Inc., Raynham, MA (US)

(72) Inventors: Christopher R. Warren, Aliso Viejo, CA (US); Robert Flower, Sun City, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/723,377

(22) Filed: May 27, 2015

(65) Prior Publication Data
US 2015/0374416 A1   Dec. 31, 2015

Related U.S. Application Data

(60) Provisional application No. 62/003,384, filed on May 27, 2014, provisional application No. 62/035,703, (Continued)

(51) Int. Cl.
*A61B 17/70* (2006.01)
*A61B 17/86* (2006.01)
(Continued)

(52) U.S. Cl.
CPC ...... *A61B 17/7065* (2013.01); *A61B 17/0642* (2013.01); *A61B 17/1659* (2013.01); *A61B 17/70* (2013.01); *A61B 17/7001* (2013.01); *A61B 17/7002* (2013.01); *A61B 17/7014* (2013.01); *A61B 17/7047* (2013.01);
(Continued)

(58) Field of Classification Search
CPC ............ A61B 17/7065; A61B 17/7047; A61B 17/7014; A61B 17/8685; A61B 17/3417
See application file for complete search history.

(56) References Cited

U.S. PATENT DOCUMENTS 4,611,582 A   9/1986   Duff
4,646,741 A   3/1987   Smith
(Continued)

FOREIGN PATENT DOCUMENTS

CN   201516081 U   6/2010
CN   203280475 U   11/2013
(Continued)

OTHER PUBLICATIONS

Aug. 6, 2015 International Search Report and Written Opinion for PCT Application No. PCT/US2015/032712, the PCT counterpart of the present application.
(Continued)

*Primary Examiner* — Julianna N Harvey
(74) *Attorney, Agent, or Firm* — BakerHostetler

(57) ABSTRACT

Disclosed are fixation devices for repairing spondylolysis. The fixation device can include a first anchor, a second anchor, and a bridge that couples the first and second anchors together. In use, the first anchor can be implanted on one side of a pars fracture, the second anchor can be implanted on the other side of the pars fracture, and the bridge can span across the pars fracture. In some embodiments, the fixation device can be compressible to promote healing of the fracture.

19 Claims, 67 Drawing Sheets

Related U.S. Application Data filed on Aug. 11, 2014, provisional application No. 62/068,313, filed on Oct. 24, 2014, provisional application No. 62/094,844, filed on Dec. 19, 2014, provisional application No. 62/096,446, filed on Dec. 23, 2014.

(51) Int. Cl.
*A61B 17/88* (2006.01)
*A61B 17/064* (2006.01)
*A61B 17/16* (2006.01)
*A61B 17/68* (2006.01)
*A61B 17/00* (2006.01)

(52) U.S. Cl.
CPC ........ *A61B 17/869* (2013.01); *A61B 17/8685* (2013.01); *A61B 17/8695* (2013.01); *A61B 17/8875* (2013.01); *A61B 17/8897* (2013.01); *A61B 17/1671* (2013.01); *A61B 2017/00867* (2013.01); *A61B 2017/0641* (2013.01); *A61B 2017/681* (2013.01)

(56) References Cited

U.S. PATENT DOCUMENTS

| | | | |
|---|---|---|---|
| 4,889,119 | A | 12/1989 | Jamiolkowski et al. |
| 6,511,481 | B2 | 1/2003 | Von et al. |
| 6,951,561 | B2 | 10/2005 | Warren et al. |
| 7,588,589 | B2 | 9/2009 | Falahee |
| 7,658,753 | B2 | 2/2010 | Carl et al. |
| 7,824,429 | B2 | 11/2010 | Culbert et al. |
| 7,842,074 | B2 | 11/2010 | Abdou |
| 7,883,532 | B2 | 2/2011 | Biscup et al. |
| 8,083,780 | B2 * | 12/2011 | McClellan, III ... A61B 17/7004 606/277 |
| 8,221,461 | B2 | 7/2012 | Kuiper et al. |
| 8,241,329 | B2 | 8/2012 | Abdou |
| 2002/0022764 | A1 * | 2/2002 | Smith ............... A61B 17/3417 600/114 |
| 2002/0143335 | A1 | 10/2002 | Von et al. |
| 2003/0097132 | A1 | 5/2003 | Padget et al. |
| 2009/0112266 | A1 * | 4/2009 | Weng ................ A61B 17/7067 606/257 |
| 2011/0184472 | A1 * | 7/2011 | Niederberger ....... A61B 17/686 606/304 |
| 2011/0196429 | A1 * | 8/2011 | Hua .................. A61B 17/7001 606/279 |
| 2012/0215264 | A1 * | 8/2012 | Lee .................... A61B 17/7037 606/305 |
| 2013/0178903 | A1 | 7/2013 | Abdou |
| 2013/0268009 | A1 | 10/2013 | Giordano |

FOREIGN PATENT DOCUMENTS

| | | |
|---|---|---|
| KZ | 21759 | 10/2009 |
| WO | WO 2009/025984 | 2/2009 |
| WO | WO 2010/039817 | 4/2010 |

OTHER PUBLICATIONS

Shvyrkov M.B., et al.: Neognestrelnye perelomy chelyustey. Moskva, Medisina, 1999, p. 239.

Gray's Anatomy, Crown Publishers, Inc., 1977, pp. 33-54.

Zhu, Repair of pars defect in a patient accompanied with disc herniation by a modified Buck's, European Review for Medical and Pharmacological Sciences, 2012, 16: 1859-1865.

Widi, Minimally Invasive Direct Repair of Bilateral Lumbar Spine Pars Defects in Athletes, Case Reports in Medicine, Hindawi Publishing Corporation, vol. 2013, Article ID 659078, 5 pages.

Nov. 29, 2016 International Report on Patentability for Application No. PCT/US2015/032712, dated Nov. 29, 2016, the PCT counterpart of the present application.

FXDevices, We Develop Ideas, downloaded Feb. 25, 2015, 7 pages.

Bosma, Direct Spondylolysis repair with Perpos Screws, Perpos Lysis Repair, 2014, 8 pages.

Bone Fixation System, 09/558,057, filed Apr. 26, 2000.

\* cited by examiner

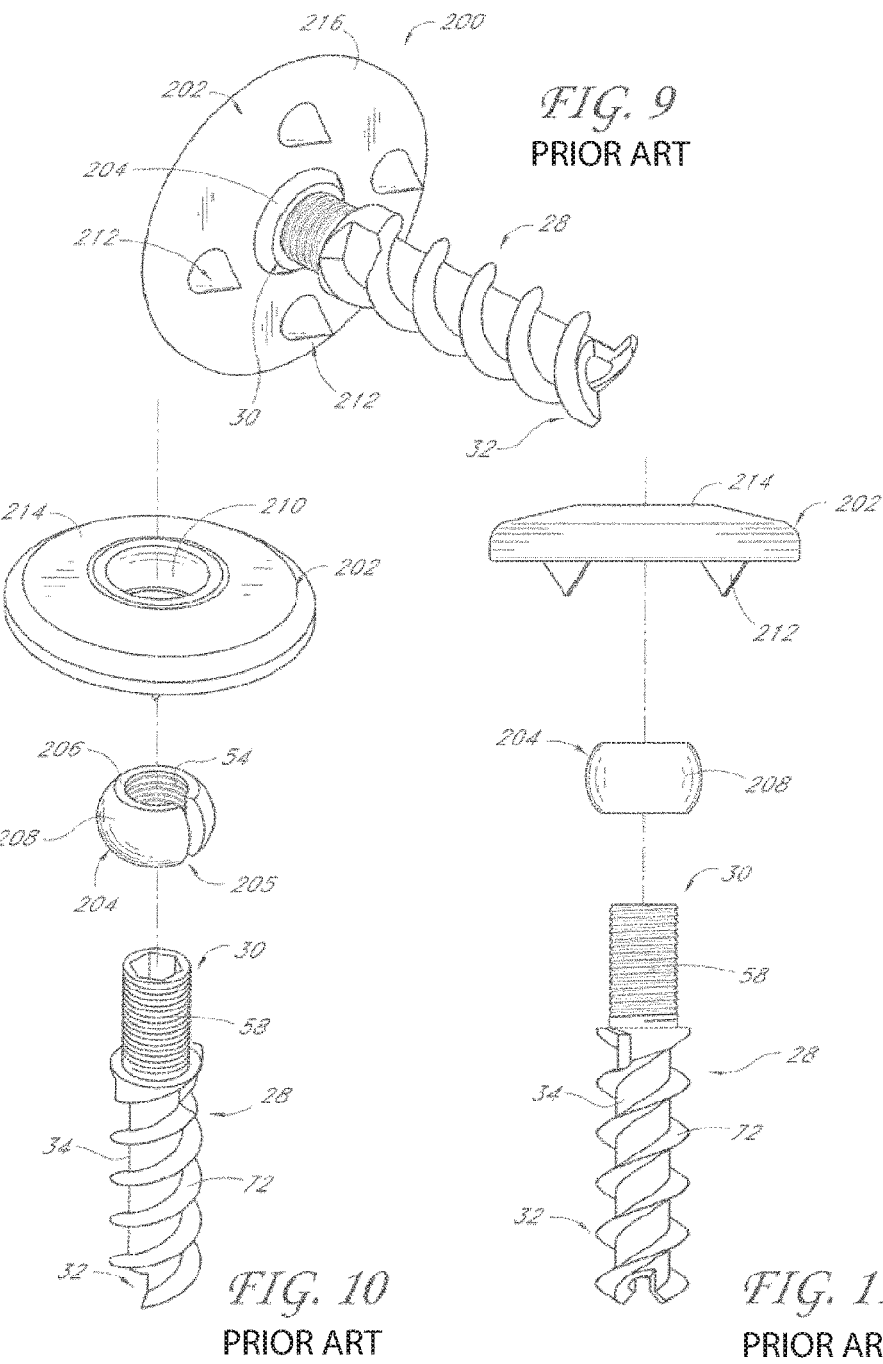

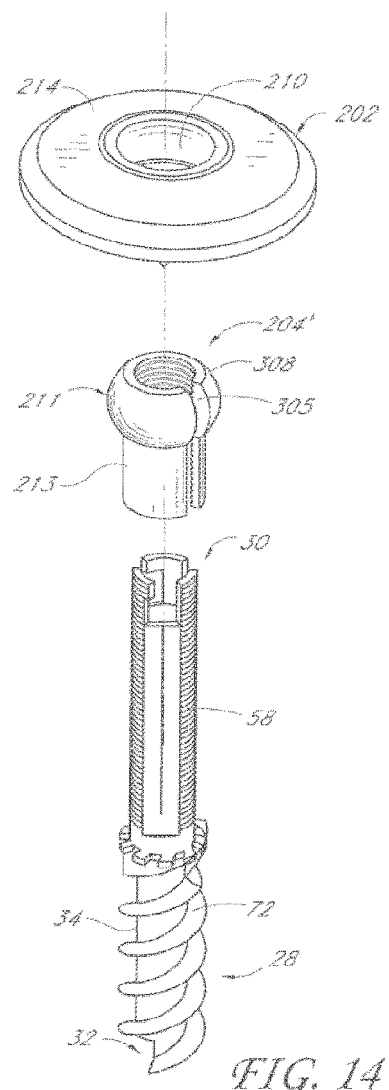
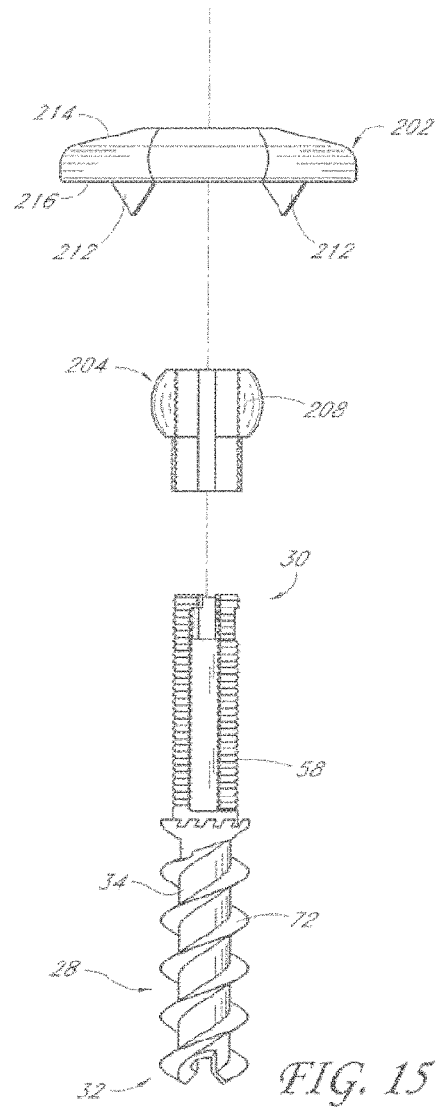
FIG. 14
PRIOR ART
FIG. 15
PRIOR ART

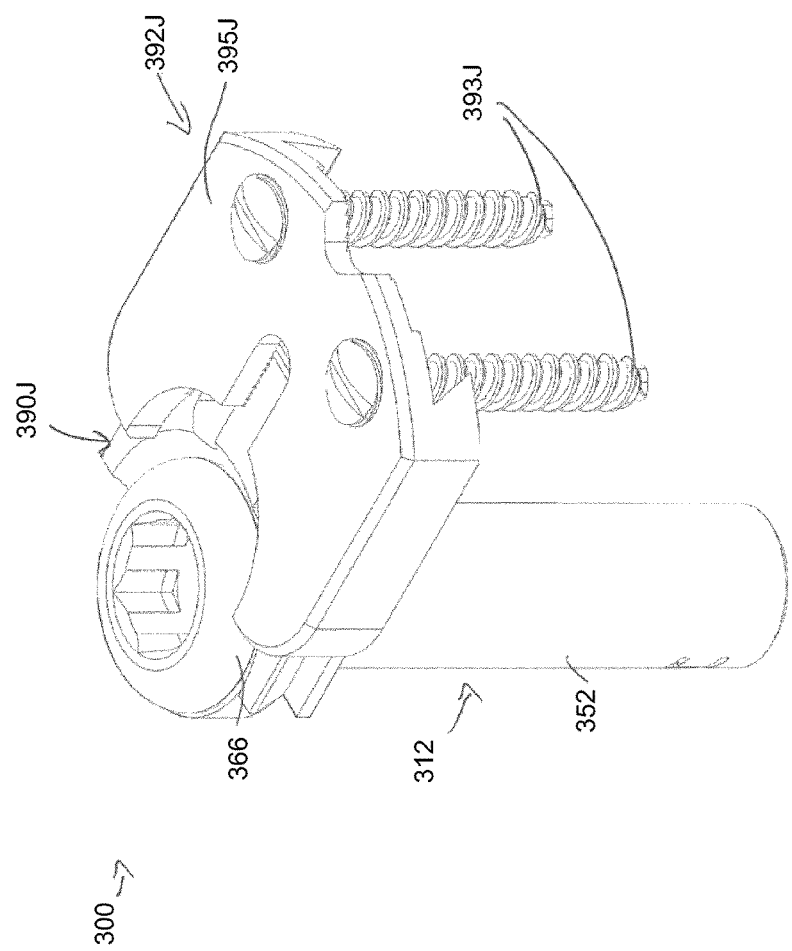

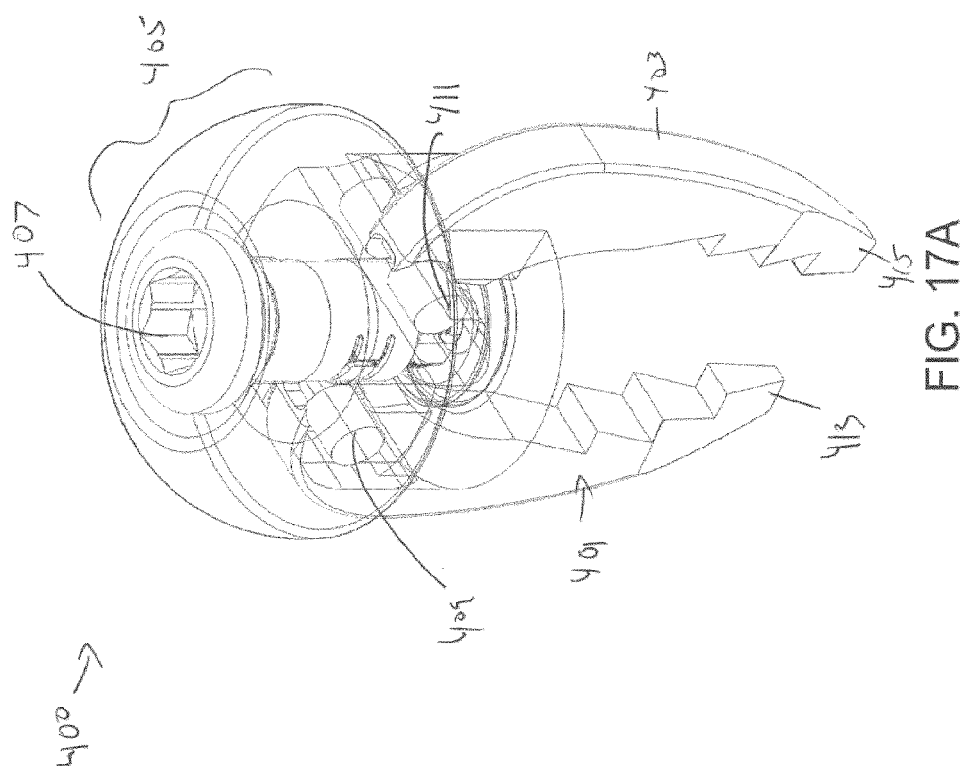

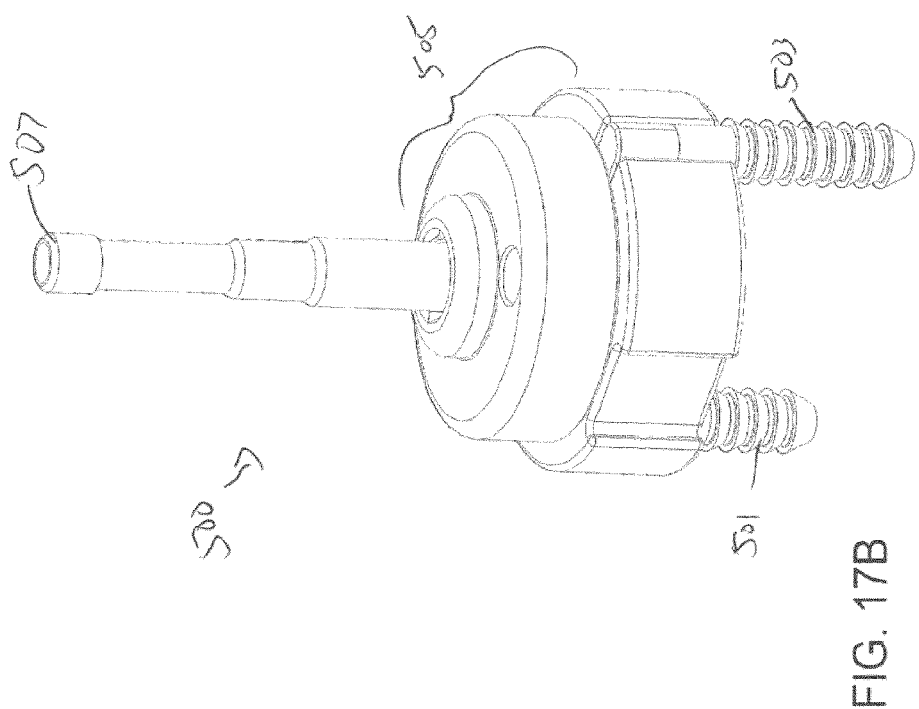

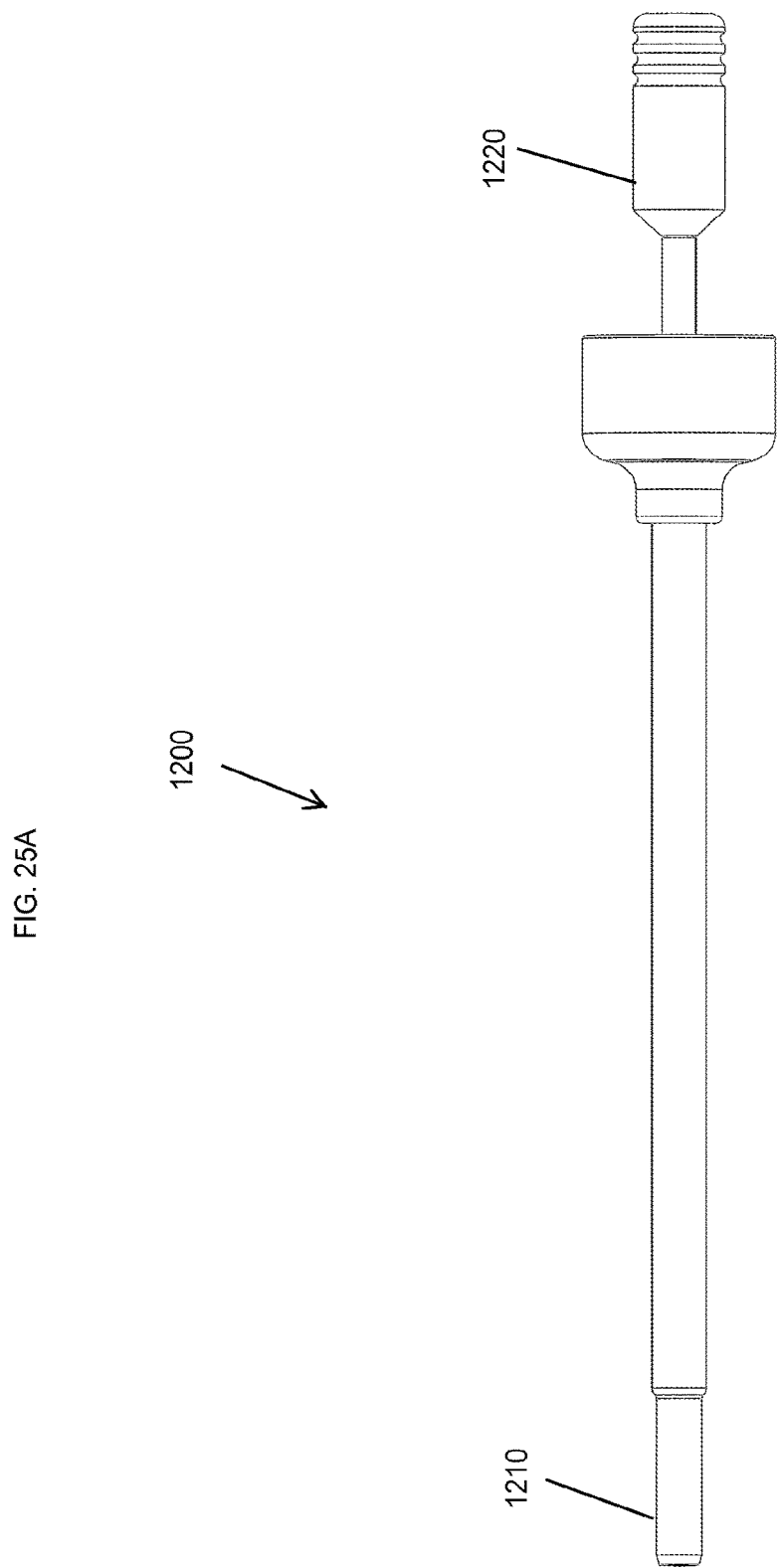

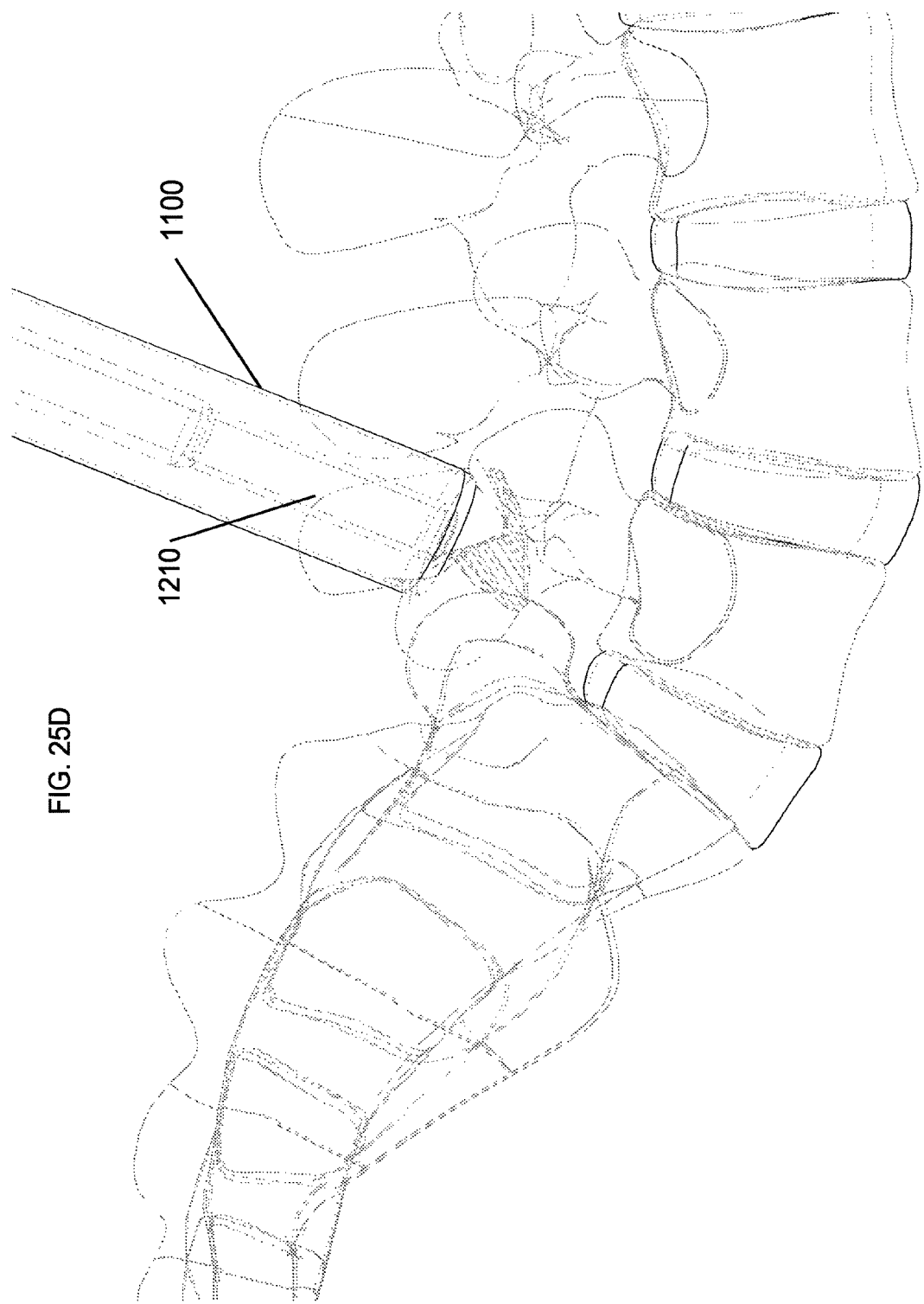

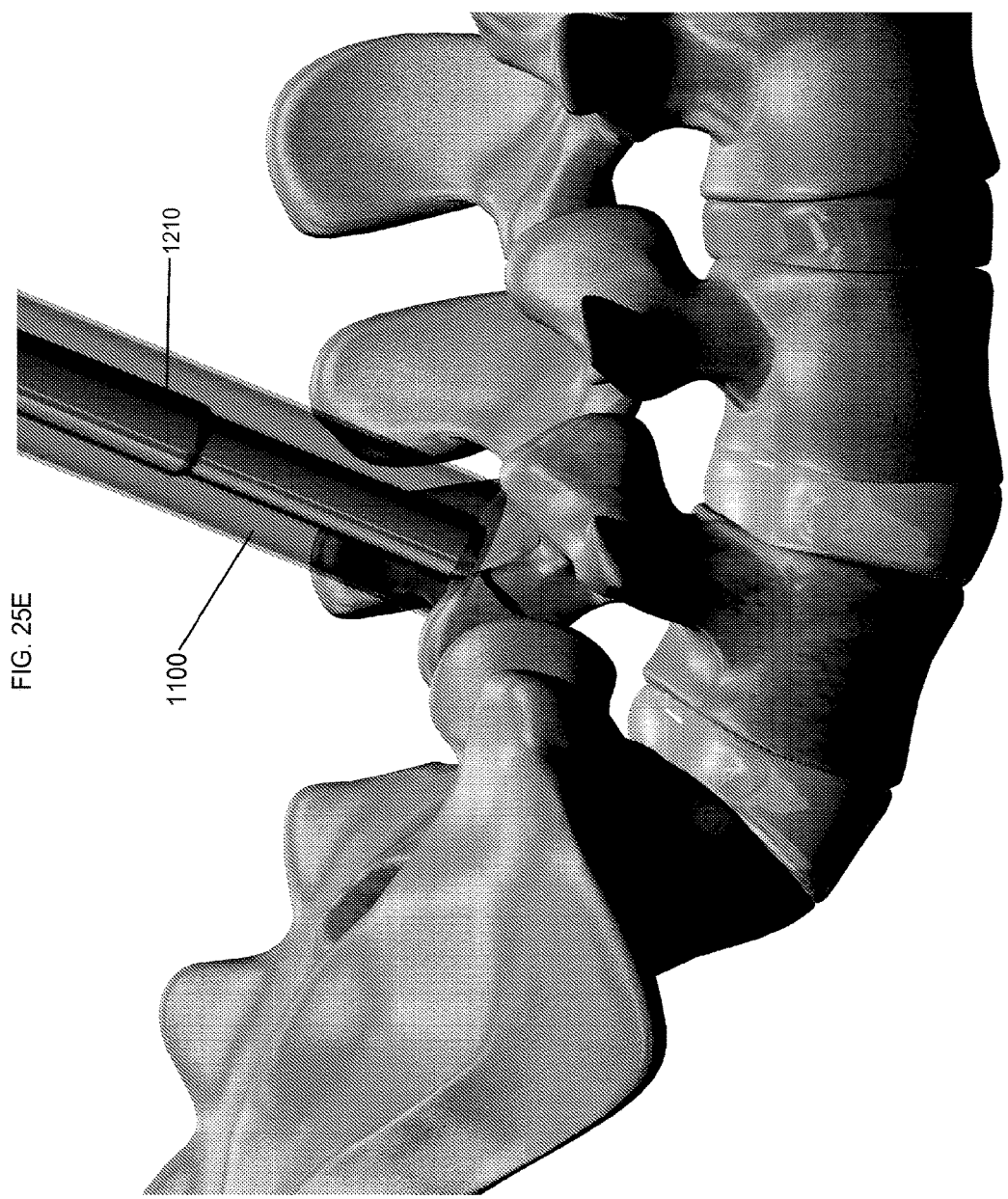

METHOD AND APPARATUS FOR SPONDYLOLYSIS REPAIR

CROSS-REFERENCE TO RELATED APPLICATIONS

This present application claims priority under 35 U.S.C. § 119(e) to U.S. Provisional Patent Application No. 62/003,384, filed May 27, 2014, U.S. Provisional Patent Application No. 62/035,703, filed Aug. 11, 2014, U.S. Provisional Patent Application No. 62/068,313, filed Oct. 24, 2014, U.S. Provisional Patent Application No. 62/094,844, filed Dec. 19, 2014, and U.S. Provisional Patent Application No. 62/096,446, filed Dec. 23, 2014, the disclosure of each of these applications is incorporated by reference herein in their entirety.

BACKGROUND

Field

The present disclosure relates to medical devices and, more particularly, to methods and apparatus for spondylolysis repair.

Description of the Related Art

The human spine is a flexible weight bearing column formed from a plurality of bones called vertebrae. There are thirty-three vertebrae, which can be grouped into one of five regions (cervical, thoracic, lumbar, sacral, and coccygeal). Moving down the spine, there are generally seven cervical vertebrae, twelve thoracic vertebra, five lumbar vertebra, five sacral vertebra, and four coccygeal vertebra. The vertebrae of the cervical, thoracic, and lumbar regions of the spine are typically separate throughout the life of an individual. In contrast, the vertebra of the sacral and coccygeal regions in an adult are fused to form two bones, the five sacral vertebra which form the sacrum and the four coccygeal vertebra which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylolysis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

One particular source of pain and disability is spondylolysis, otherwise known as pars fracture or pars defect, which is a fracture or dislocation of the pars interarticularis. The pars interarticularis is the bony mass between the facet joints, anterior to the lamina and posterior to the pedicle. With a pars fracture, the pars interarticularis is detached and there is a separation of the joints. These fractures are generally caused by mechanical stress and fatigue "stress" fractures caused by repetitive loading. It is reported that between 6% and 10% of the population have pars defects, with a higher prevalence among athletes. Spondylolysis can be treated conservatively by bracing, or by injections which do not themselves correct the condition but may relieve the associated pain. While some patients with spondylolysis do not require surgery, for others surgical intervention is necessary. One approach is full interbody fusion, which is typically associated with patients for whom the pars defect has caused or contributed to a spondylolysis of greater than grade 1, or where leg pain or weakness is present. Full interbody fusion is a high-profile, disruptive technique with significant operating and recovery times. Additionally, full body fusion is particularly inappropriate for younger patients, and for athletes of any age, as it results in loss of motion at one level.

Another surgical approach is direct repair of spondylolysis, without interbody fusion. Existing systems include a pedicle screw and hook fixation, pedicle screw and V-rod system, a cable-screw construct, or a direct insertion of a bone screw across the fracture (i.e., Buck's technique). Each of these techniques suffers from significant shortcomings. For example Buck's technique is an unfamiliar technique for surgeons and requires anchoring the screw in a thin portion of the vertebrae, thereby risking further fracture or dislocation of the bone screw. Pedicle screw and hook, pedicle screw and V-rod, or cable-screw constructs all require open surgery, with no option for minimally invasive surgery. Each also relies on complex hardware, with long operating times and long recovery times.

Notwithstanding the variety of efforts in the prior art, there remains a need for a fixation device for treatment of spondylolysis which provides improved locking force, which resists migration, and which can be easily and rapidly deployed via a minimally invasive approach.

SUMMARY

In some embodiments, a method for repairing spondylolysis is provided. The method can include the step of advancing a fixation device having a first anchor, a second anchor, and a bridge extending between the two towards a target site. The method can include the step of positioning the first anchor of a fixation device against bone on one side of a pars fracture. The method can include the step of positioning the second anchor of the fixation device against bone on the other side of the pars fracture. The method can include the step of advancing the first and second anchors into bone.

In some embodiments, the first anchor comprises a compression screw. In some embodiments, the compression screw comprises a body having a distal anchor, a proximal anchor, and an inner member disposed within the body. In some embodiments, advancing the first anchor into bone comprises: advancing the distal anchor into the bone; and axially shortening the compression screw by reducing the distance between the distal anchor and the proximal anchor, such that a locking element on the proximal anchor engages at least one retention structure on the body. In some embodiments, the second anchor comprises a spike. In some embodiments, the spike includes a plurality of retention structures. In some embodiments, the second anchor is slidably movable with respect to the first anchor. In some embodiments, the second anchor is rotatable with respect to the first anchor. In some embodiments, the second anchor comprises a threaded screw. In some embodiments, the fixation device is configured such that, after being advanced into bone, the first and second anchors are pulled toward one another. In some embodiments, each of the first and second anchors comprises a spike. In some embodiments, the spikes comprise a plurality of retention structures. In some embodiments, the fixation device comprises a compressible staple made substantially of a shape memory material. In some embodiments, the first and second anchors are advanced into bone substantially simultaneously. In some embodiments, the first anchor is advanced into bone before the second anchor is advanced into bone. In some embodiments, the method can include the step of pre-drilling a guide hole into bone for the first anchor. In some embodiments, the fixation device is positioned against the bone through a cannula. In some embodiments, the method can include the step of disposing bone graft material, bone growth promoters, and/or bone cement into the pars fracture.

In some embodiments, a fixation device for repairing spondylolysis is provided. The fixation device can include first and second anchors. Each of the first and second anchors can include an elongate body, having a proximal end and a distal end. Each of the first and second anchors can include an anchor on the distal end. Each of the first and second anchors can include a first retention structure on the body, proximal to the anchor. Each of the first and second anchors can include a proximal anchor, movably carried by the body. Each of the first and second anchors can include a second retention structure on the interior of the proximal anchor for cooperating with the first retention structure on the body. In some embodiments, the proximal anchor is movable in the distal direction with respect to the body and the retention structure resists proximal movement of the proximal anchor with respect to the body. The fixation device can include a bridge coupling the first anchor and the second anchor together.

In some embodiments, a fixation device for repairing spondylolysis is provided. The fixation device can include a first anchor. The first anchor can include an elongate body, having a proximal end and a distal end. The first anchor can include an anchor on the distal end. The first anchor can include a first retention structure on the body, proximal to the anchor. The first anchor can include a proximal anchor, movably carried by the body. The first anchor can include a second retention structure on the interior of the proximal anchor for cooperating with the first retention structure on the body. In some embodiments, the proximal anchor is movable in the distal direction with respect to the body and the retention structure resists proximal movement of the proximal anchor with respect to the body. The fixation device can include a bridge extending laterally from the proximal anchor of the first anchor. The fixation device can include a second anchor coupled to the bridge, the second anchor extending substantially parallel to the first anchor.

In some embodiments, a fixation device for repairing spondylolysis is provided. The fixation device can include a bridge having a proximal end, a distal end, and a longitudinal axis extending between the first end and the second end, wherein the bridge comprises a first retention structure. The fixation device can include a first anchor coupled to the bridge at the proximal end, the first anchor comprising a second retention structure for cooperating with the first retention structure on the bridge. The fixation device can include a second anchor coupled to the bridge at the distal end. In some embodiments, the first anchor is movable in the distal direction with respect to the bridge and the retention structure resists distal movement of the first anchor with respect to the bridge.

In some embodiments, a fixation device for repairing spondylolysis is provided. The fixation device can include a staple comprising a first prong, a second prong, and a bridge extending between the two. In some embodiments, the staple is made substantially of shape memory metal.

In some embodiments, a fixation device for repairing spondylolysis is provided. The fixation device can include a staple comprising a first prong, a second prong, and a bridge extending between the two. In some embodiments, the bridge comprises a spring element. In some embodiments, the staple further comprises a third prong coupled to the bridge. In some embodiments, the staple further comprises a fourth prong coupled to the bridge.

In some embodiments, a method for repairing spondylolysis in provided. The method can include the step of creating an access path from a position above, posterolaterally or lateral to a pars fracture. The method can include the step of preparing the pars facture through the access path. The method can include the step of securing the pars facture from along the access path.

In some embodiments, the step of preparing the pars fracture through the access site includes at least one of placing bone graft, rasping eroding, grinding or burring. In some embodiments, the step of creating an access path from a position above a pars facture to the pars fracture comprises placing a guide member from a position above the fracture site into the facture site and then advancing a dilator over the guide member to form the access path. In some embodiments, the guide member comprises a k-wire or guide wire. In some embodiments, the dilator comprises a series of sequential dilators. In some embodiments, the step of securing the pars facture comprises inserting a fixation device through the access path.

In some embodiments, a method for repairing spondylolysis is provided. The method can include the step of creating an access path from a position above, posterolaterally or lateral to a pars fracture. The method can include the step of inserting a fixation device through the access path. The method can include the step of securing the pars facture. In some embodiments, the step of creating an access path from a position above a pars facture to the pars fracture comprises placing a guide member from a position above the fracture site into a facture site and then advancing a dilator over the guide member to form the access path. In some embodiments, the guide member comprises a k-wire or guide wire. In some embodiments, the dilator comprises a series of sequential dilators. In some embodiments, the fixation device is made at least partially from a bioabsorbable metallic material or metallic alloy. In some embodiments, bioabsorbable metallic material or metallic alloy comprises magnesium, a magnesium alloy, zinc and/or a zinc alloy. In some embodiments, the fixation device is made at least partially from a bioabsorbable metallic material or metallic alloy. In some embodiments, bioabsorbable metallic material or metallic alloy comprises magnesium, a magnesium alloy, zinc and/or a zinc alloy.

BRIEF DESCRIPTION OF THE DRAWINGS

FIG. 9 is a bottom perspective view of a modified embodiment of a bone fixation device.

FIG. 10 is an unassembled side perspective view of the bone fixation device of FIG. 9.

FIG. 11 is an unassembled side view of the bone fixation device of FIG. 9.

FIG. 14 is an unassembled side perspective view of another modified embodiment of a bone fixation device.

FIG. 15 is an unassembled side view of the bone fixation device of FIG. 9.

FIG. 16A-16J illustrate various embodiments of an implant for pars defect repair comprising a bone compression screw.

FIGS. 17A-17B illustrate additional embodiments of an implant for pars defect repair.

FIGS. 25A-E illustrate an embodiment of a tool delivered through the cannula of FIGS. 23A-23J.

DETAILED DESCRIPTION

Although the fixation devices of the present disclosure will be disclosed primarily in the context of a spondylolysis repair procedure, the methods and structures disclosed herein are intended for application in any of a variety medical applications, as will be apparent to those of skill in the art in view of the disclosure herein. For example, the bone fixation device may be applicable to fractures in other bones, for example in elsewhere in the spine, in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. The fixation devices may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation devices may also be used to attach sutures to the bone, such as in any of a variety of tissue suspension procedures. The bone fixation device described herein may be used with or without plate(s) or washer(s), all of which can be either permanent, absorbable, or combinations.

Figure 1:
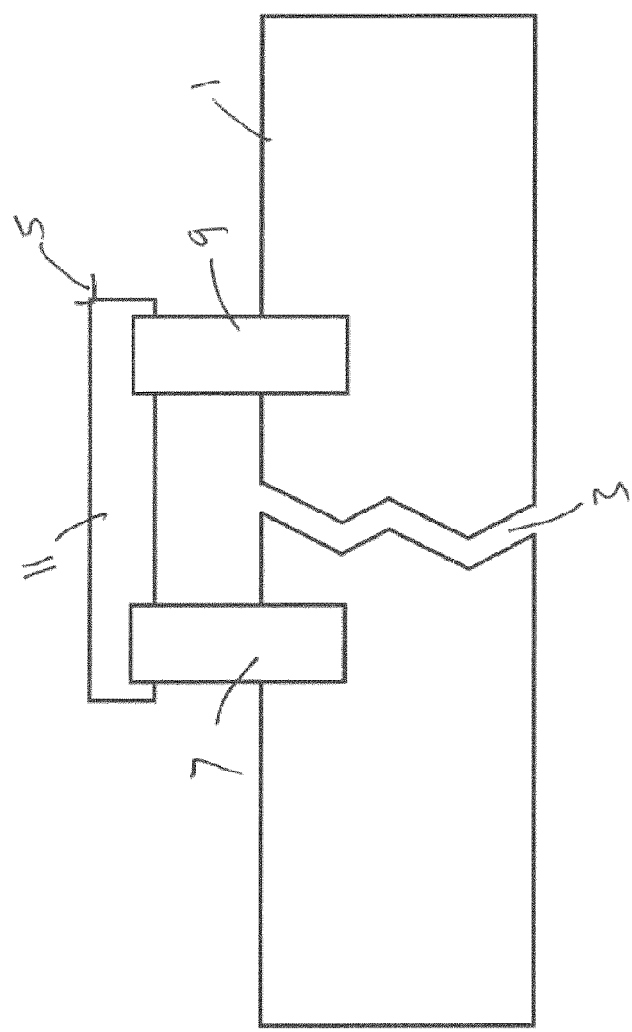
FIG. 1 is a schematic view of an implant spanning a pars fracture.

Referring to FIG. 1, there is illustrated a schematic view of a fixation device that can be implanted over a pars fracture and/or in certain arrangements posterolaterally or lateral to a pars fracture. The vertebra 1 includes a fracture 3, which may be disposed in the pars interarticularis. An implant 5 is disposed across the fracture 3, and includes a first anchor 7, a second anchor 9, and a bridge 11 spanning the first and second anchors. As will be described in more detail below, the anchors and bridge may take a variety of forms, for example each anchor may be a screw, a spike, a post, or other structure configured to be inserted into a bore (either pre-formed or formed upon entry of the anchor) in the bone. In some embodiments, the implant 5 may be configured to provide compression between the first anchor 7 and the second anchor 9, so as to compress the two portions of bone together at the point of the fracture 3. In some embodiments, bone graft, bone growth promoting material, or other material may be inserted into the fracture either before insertion of the implant, during insertion of the implant, and/or after. In some embodiments, the fracture is prepared before insertion of the implant, during insertion of the implant or after insertion. Such preparation of the fracture site can include rasping, eroding, grinding, burring etc. of the fracture site, removing bone tissue, scar tissue, cartilage formation, placement of bone graft material and/or bone cement. In some embodiments, the first anchor may be inserted into bone, with the bridge coupled to the first anchor, after which the second anchor may be inserted. In other embodiments, the process may be reversed. In some embodiments, the implant 5 is configured such that opening tightening of the first anchor 7, the bridge 11 and second anchor 9 together exert a compressive force such that the second anchor 9 is urged towards the first anchor 7. In such embodiments, tightening of the first anchor 7 not only further secures the first anchor into bone, but also contributes compression of the second anchor 9 towards the first anchor 7, which can aid in reducing or repairing the fracture. In some embodiments, the first anchor 7, the second anchor 9, and the bridge 11 can be formed of a single integral component. In other embodiments, the first anchor 7, the second anchor 9, and the bridge 11 can comprise separate components that are formed of multiple parts and/or some components can be combined into a single component. In some embodiments, the implant 5 can be inserted along the same access path and/or through the same access instrument (or portion thereof) that is used to prepare the pars facture. Accordingly in certain arrangements, an access path can be created from a position above, posterolaterally or lateral to a pars fracture. The pars facture can be prepared through the access path. The pars fracture can be secured using by inserting an implant 5 along the access path. In certain embodiments, an access path is created from a a position above, posterolaterally or lateral to a pars fracture. The implant 5 can be inserted through the access path to secure the pars facture. The fracture can be prepared through or along the same access path.

Referring to FIGS. 2-15, exemplary fixation devices are described below. Additional embodiments and modifications of the fixation 12 device can also be found in U.S. Pat. Nos. 7,824,429 and 6,951,561, the entirety of which are hereby incorporated by reference in their entirety. As will be described below, certain features of these devices can be used in the embodiments described below and the description of these exemplary fixation devices will be used to explain the later embodiments.

In one arrangement, the fixation device 12 includes a body 28 comprising titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. In the illustrated arrangement, the distal anchor 34 comprises a helical locking structure 72 for engaging cancellous and/or distal cortical bone. In the illustrated arrangement, the locking structure 72 comprises a flange that is wrapped around an axial lumen. The flange extends through at least one and generally from about 2 to about 50 or more full revolutions depending upon the axial length of the distal anchor and intended application. The flange will can complete from about 2 to about 20 revolutions. The helical flange 72 is provided with a pitch and an axial spacing to optimize the retention force within cancellous bone, to optimize compression.

Figure 4:
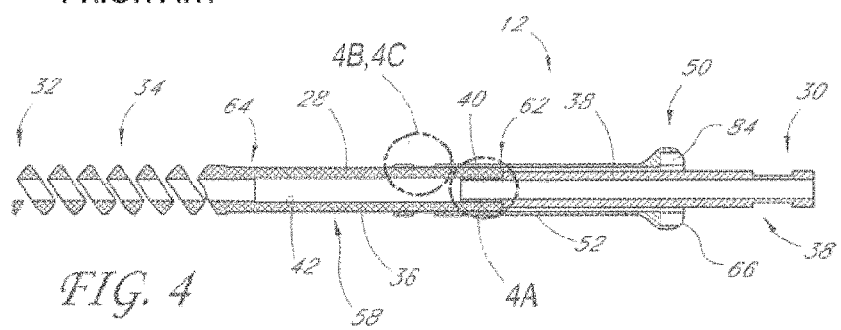
FIG. 4 is a cross-sectional view taken through line 4-4 of FIG. 3.

The helical flange 72 of the illustrated arrangement has a generally triangular cross-sectional shape (see FIG. 4). However, it should be appreciated that the helical flange 72 can have any of a variety of cross sectional shapes, such as rectangular, oval or other as deemed desirable for a particular application through routine experimentation in view of the disclosure herein. The outer edge of the helical flange 72 defines an outer boundary. The ratio of the diameter of the outer boundary to the diameter of the central lumen can be optimized with respect to the desired retention force within the cancellous bone and giving due consideration to the structural integrity and strength of the distal anchor 34. Another aspect of the distal anchor 34 that can be optimized is the shape of the outer boundary and the central core, which in the illustrated embodiment are generally cylindrical.

The distal end 32 and/or the outer edges of the helical flange 72 may be atraumatic (e.g., blunt or soft). This inhibits the tendency of the fixation device 12 to migrate anatomically distally after implantation. Distal migration is also inhibited by the dimensions and presence of a proximal anchor 50, which will be described below.

A variety of other arrangements for the distal anchor 32 can also be used. For example, the various distal anchors described in co-pending U.S. patent application Ser. No. 10/012,687, filed Nov. 13, 2001 can be incorporated into the fixation device 12 described herein. The entire contents of this application is hereby expressly incorporated by reference. In particular, the distal anchor may comprise a single helical thread surrounding a central core, much as in a conventional screw, which has been cannulated to facilitate placement over a wire. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone.

Figure 3:
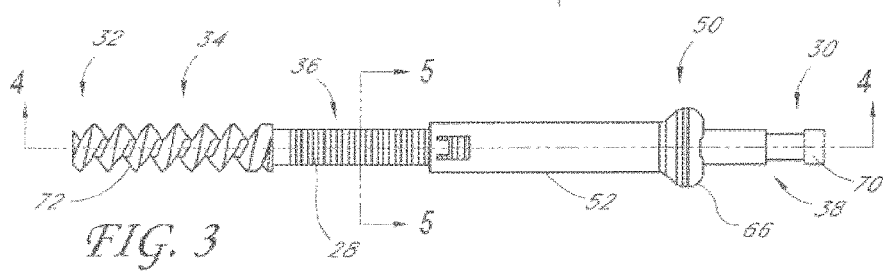
FIG. 3 is a side elevational view of the fixation device of FIG. 2.
Figure 4A:
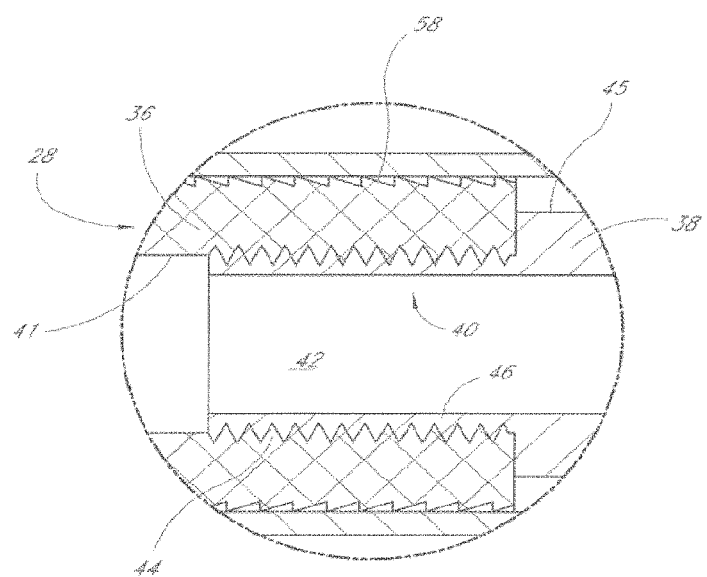
FIG. 4A is an enlarged view of portion 4A of FIG. 4.

With particular reference to FIGS. 3, 4, and 4A, the body 28 comprises a first portion 36 and a second portion 38 that are coupled together at a junction 40. In the illustrated embodiment, the first portion 36 carries the distal anchor 34 while the second portion 38 forms the proximal end 30 of the body 28. As will be explained in more detail below, in certain embodiments, the second portion 38 may be used to pull the body 28 and therefore will sometimes be referred to as a "pull-pin". The first and second portions 36, 38 are preferably detachably coupled to each other at the junction 40. In the illustrated embodiment, the first and second portions 36, 38 are detachably coupled to each other via interlocking threads. Specifically, as best seen in FIG. 4A, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally to compress the fracture. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein. It should also be appreciated that the body may be from a single piece as described in U.S. Pat. No. 6,511,481, which has been incorporated by reference herein.

As shown in FIG. 4, the body 28 is cannulated to accommodate installation over a placement wire as is understood in the art. The cross section of the illustrated central cannulation is circular but in other embodiments may be non-circular, e.g., hexagonal, to accommodate a corresponding male tool for installation or removal of the second portion 38 of the body 28 as explained above. In other embodiments, the body 28 may partially or wholly solid.

Figure 2:
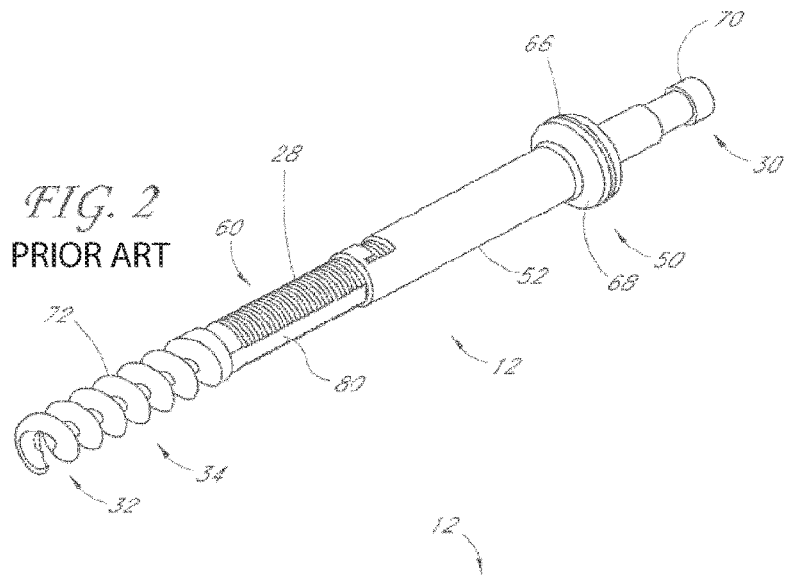
FIG. 2 is a side perspective view of an exemplary fixation device.

With continued reference to FIGS. 2-4, the proximal end 30 of the body 28 may be provided with a rotational coupling 70, for allowing the second portion 38 of the body 28 to be rotationally coupled to a rotation device. The proximal end 30 of the body 28 may be desirably rotated to accomplish one or two discrete functions. In one application, the proximal end 30 is rotated to remove the second portion 38 of the body 28 following tensioning of the device to anchor an attachment to the bone. Rotation of the rotational coupling 70 may also be utilized to rotationally drive the distal anchor into the bone. Any of a variety of rotation devices may be utilized, such as electric drills or hand tools, which allow the clinician to manually rotate the proximal end 30 of the body. Thus, the rotational coupling 70 may have any of a variety of cross sectional configurations, such as one or more flats or splines.

In one embodiment, the rotational coupling 70 comprises a proximal projection of the body 28 having an axial recess with a polygonal cross section, such as a hexagonal cross section. The rotational coupling 70 is illustrated as a female component, machined or milled or attached to the proximal end 30 of the body 28. However, the rotational coupling may also be in the form of a male element, such as a hexagonal or other noncircular cross sectioned projection.

The proximal end 30 of the fixation device is provided with a proximal anchor 50. Proximal anchor 50 is axially distally moveable along the body 28, to permit compression of between the distal and proximal ends 32, 30 of the fixation device 12. As will be explained below, complementary locking structures such as threads or ratchet like structures between the proximal anchor 50 and the body 28 resist proximal movement of the anchor 50 with respect to the body 28 under normal use conditions. The proximal anchor 50 preferably can be axially advanced along the body 28 with and/or without rotation as will be apparent from the disclosure herein.

Referring to FIG. 4, the proximal anchor 50 comprises a housing 52 such as a tubular body, for coaxial movement along the body 28. As will be explained in more detail below, in certain embodiments, the housing 50 may have diameter sized to fit through an opening formed in fixation bar or plate.

In a final position, the distal end of the housing 52 preferably extends distally past the junction 40 between the first portion 36 and the second portion 38. The housing 52 is provided with one or more surface structures 54 such as a radially inwardly projecting flange 56 (see FIGS. 4B and 4C), for cooperating with complementary surface structures 58 on the first portion 36 of the body 28. In the illustrated embodiment, the complementary surface structures 58 comprise a series of annular ridges or grooves and/or threads 60.

The surface structures 54 and complementary surface structures 58 permit distal axial travel of the proximal anchor 50 with respect to the body 28, but resist proximal travel of the proximal anchor 50 with respect to the body 28.

Figure 4B:
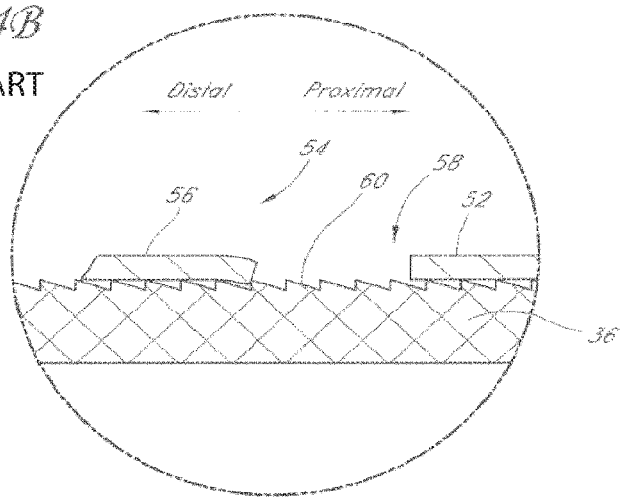
FIG. 4B is an enlarged view of portion 4B of FIG. 4 with the fixation device in a first position.
Figure 4C:
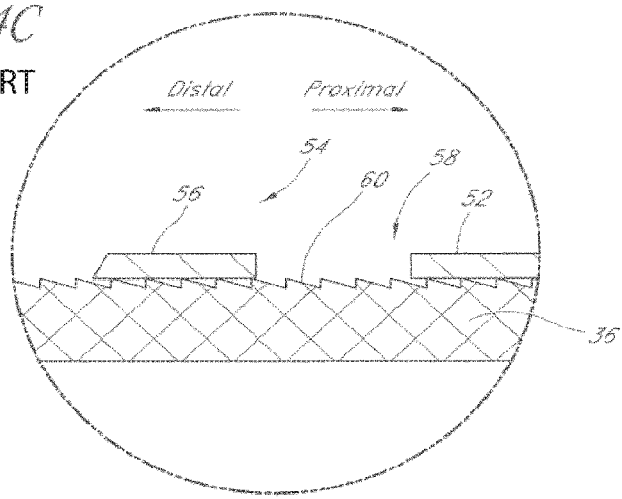
FIG. 4C is an enlarged view of portion 4C of FIG. 4 with the fixation device in a second position.

For example, as best seen in FIG. 4B, the proximal end of the flange 56 is biased towards the longitudinal axis of the body 28. As such, when the proximal anchor 50 is urged proximally with respect to the body 28, the flange 56 engages the grooves or ridges 60 of the complementary surface structures 58. This prevents proximal movement of the proximal anchor 50 with respect to the body 28. In contrast, as best seen in FIG. 4C, when the proximal anchor 50 is moved distally with respect to the body 28, the flange 56 can bend outwardly away from the body 28 and the ridges 60 so as to allow the proximal anchor 50 to move distally. Of course, those of skill in the art will recognize that there are a variety of other complementary surface structures, which permit one way ratchet like movement. For example, a plurality of annular rings or helical threads, ramped ratchet structures and the like for cooperating with an opposing ramped structure or pawl can also be used. In one embodiment, opposing screw threads are dimensioned to function as a ratchet. In other embodiments, the complementary surface structures can comprise complementary threads.

Retention structures 58 (e.g., grooves or threads) are spaced axially apart along the body 28, between a proximal limit 62 and a distal limit 64. The axial distance between proximal limit 62 and distal limit 64 is related to the desired axial working range of the proximal anchor 50, and thus the range of functional sizes of the fixation device 12. Thus, the fixation device 12 of the exemplary embodiment can provide compression between the distal anchor 34 and the proximal anchor 50 throughout a range of motion following the placement of the distal anchor in bone.

In many applications, the working range is at least about 10% of the overall length of the device, and may be as much as 20% or 50% or more of the overall device length. The embodiments disclosed herein can be scaled to have a greater or a lesser working range, as will be apparent to those of skill in the art in view of the disclosure herein.

With reference back to FIGS. 2-4, the proximal anchor 50 includes a flange 66 that, as will be explained below, may be configured to sit against the outer surface of the bone and/or a fixation rod or plate. The flange 66 is preferably an annular flange, to optimize the footprint or contact surface area between the flange 66 and the bone or fixation rod or plate.

Figure 5:
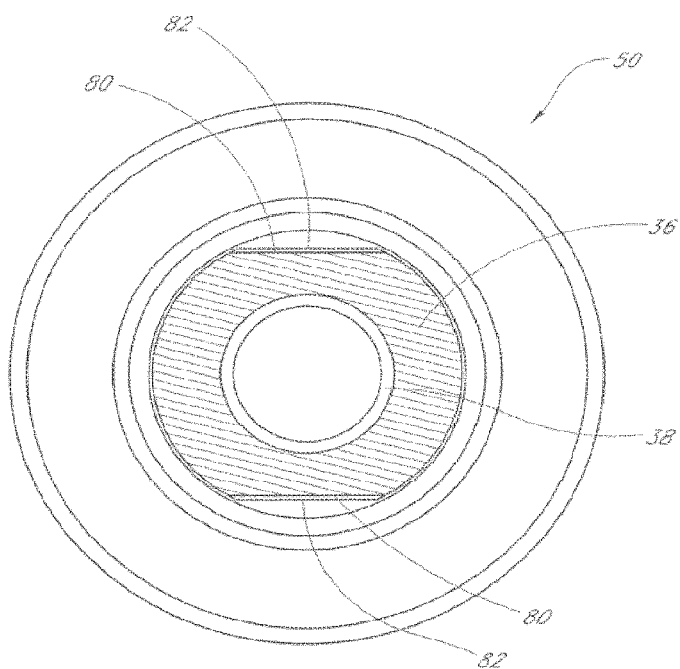
FIG. 5 is a cross-sectional view taken through line 5-5 of FIG. 3.

With particular reference to FIGS. 2 and 5, the fixation device may include an antirotation lock between the first portion 36 of the body 28 and the proximal collar 50. In the illustrated embodiment, the first portion 36 includes a pair of flat sides 80, which interact with corresponding flat structures 82 in the proximal collar 50. One or three or more axially extending flats may also be used. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28.

To rotate the proximal collar, the flange 66 is preferably provided with a gripping structure to permit an insertion tool to rotate the flange 66. Any of a variety of gripping structures may be provided, such as one or more slots, flats, bores or the like. In one embodiment, the flange 44 is provided with a polygonal, and, in particular, a pentagonal or hexagonal recess 84 (see FIG. 4).

In a modified embodiment, the housing 52 of the proximal anchor 50 can include one or more one or more barbs that extend radially outwardly from the tubular housing 52. Such barbs provide for self-tightening after the device has been implanted in the patient as described in a co-pending U.S. patent application Ser. No. 10/012,687, filed Nov. 13, 2001, which was incorporated by reference above. The barbs may be radially symmetrically distributed about the longitudinal axis of the housing 52. Each barb is provided with a transverse engagement surface, for anchoring the proximal anchor 50 in the bone. The transverse engagement surface may lie on a plane which is transverse to the longitudinal axis of the housing 50 or may be inclined with respect to the longitudinal axis of the tubular 50. In either arrangement, the transverse engagement surface 43 generally faces the contacting surface 68 of the flange 44. As such, the transverse engagement surface inhibits proximal movement of the proximal anchor with respect to the bone.

Figure 6A:
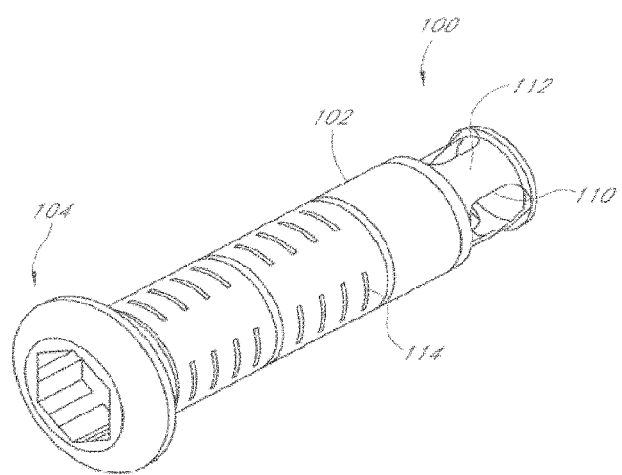
FIG. 6A is a side perspective view of another embodiment of a proximal anchor for the bone fixation device of FIG. 2.
Figure 6B:
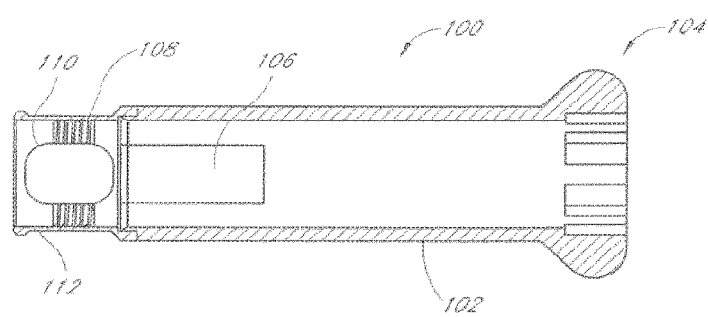
FIG. 6B is a cross-sectional view of the proximal anchor of FIG. 6A.

FIGS. 6A and 6B illustrate another embodiment of a proximal anchor 100. This embodiment also includes a tubular housing 102 and a flange 104 that may be configured as describe above with respect to FIGS. 2-4. The tubular housing 102 may include an anti-rotational lock, which, in the illustrated embodiment, is in the form of one or more sides 106 that interact with corresponding flat structures formed in the body 28 as described above.

In this embodiment, the surfaces structures comprises one or more teeth or grooves 112, which are configured to engage the complementary surfaces structures on the body 28 (see FIG. 2). One or more slots or openings 110 are formed in the tubular housing 102 to form one or more bridges 112, which carry the teeth 102. The anchor proximal anchor 100 may be pushed towards the distal end of the body and the teeth 102 can slide along the and over the complementary surface structures 58 on the body 28. In the illustrated embodiment, the bridge 113 may flex slightly away from the body 28 to allow such movement. The number and shape of the openings 110 and bridges 112 may be varied depending of the desired flexing of the bridges 112 when the proximal anchor 110 is moved distally over the body and the desired retention force of the distal anchor when appropriately tensioned. In one embodiment, the teeth on the proximal anchor 100 and the grooves on the body 28 may be configured such that the proximal anchor 100 can be rotated or threaded onto the pin in the distal direct and/or so that that the proximal anchor can be removed by rotation. The illustrated embodiment also advantageously includes visual indicia 114 (e.g., marks, grooves, ridges etc.) on the tubular housing 102 for indicating the depth of the proximal housing 100 within the bone.

Figure 6C:
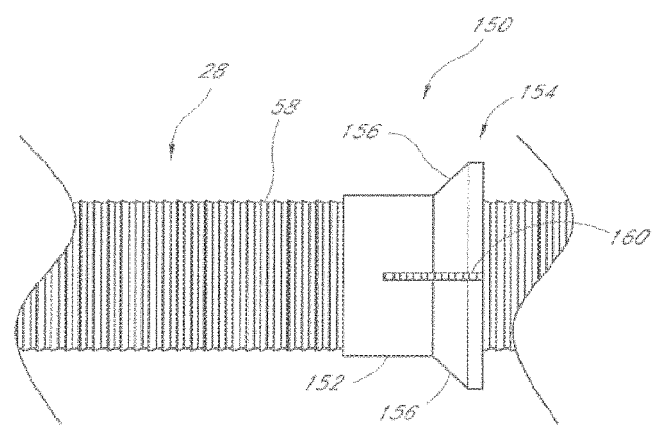
FIG. 6C is a side perspective view of another embodiment of a proximal anchor for the bone fixation device of FIG. 2.
Figure 6D:
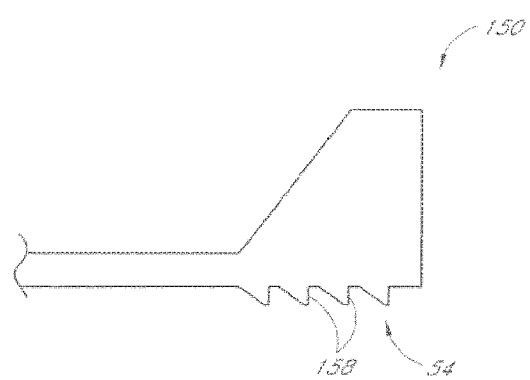
FIG. 6D is a cross-sectional view of the proximal anchor of FIG. 6C.

FIGS. 6C and 6D illustrate another embodiment of a proximal anchor 150. In this embodiment, the proximal anchor 150 comprises a housing 152 such as a tubular body, for coaxial movement along the body 28. The proximal anchor 150 also includes a flange 154 that is configured that to set against the outer surface of, for example, a bone or fixation bar or rod. In the illustrated embodiment, the flange 154 defines a contacting surface 156, which preferably forms an obtuse angle with respect to the exterior of the housing 152. However, in modified embodiments, the contacting surface 154 may be perpendicular or form an acute angle with respect to the housing 152.

Referring to FIG. 6D, in the illustrated embodiment, the complementary retention structures 54 comprise one or more inwardly projecting teeth or flanges 158, for cooperating with the complementary retention structures 58 on the body 28. The complementary retention structures 58 of the body preferably comprise a plurality of annular ridges or grooves a first surface and a second surface. The first surface generally faces the proximal direction and is preferably inclined with respect to the longitudinal axis of the body 28. In contrast, the second surface generally faces the distal direction and lies generally perpendicular to the longitudinal axis of the body 28.

The proximal anchor 150 preferably includes one or more of axial slots 160. The axial slots 160 cooperate to form lever arm(s) on which the teeth or projections 158 are positioned. Thus, as the anchor 150 is pushed towards the distal end of the body 28, the teeth 158 can slide along the first surface and ride over the retention structures 58 of the body 28 as the teeth 158 are flexed away from the body 28.

After appropriate tensioning of the proximal anchor 150, the bone may push on the angled portion contacting surface 156 of the proximal anchor 150. This force is transmitted to the teeth 158 through the lever arms. As such, the teeth 158 are prevented from flexing away from the body 28, which keeps the teeth 158 engaged with the retention structures 58 of the body 28. By increasing the tensioning force, proximal movement of the proximal anchor 150 with respect to the body 28 is resisted.

The axial length and width of the slots 160 may be varied, depending upon the desired flexing of the lever arms when the proximal anchor 150 is moved distally over the body 28 and the desired retention force of the distal anchor when appropriately tensioned. For a relatively rigid material such as titanium, axial lengths and widths of the slots 160 are approximately 0.5 mm for a proximal anchor having a length of approximately 4 mm, an inner diameter of approximately 3 mm. As such, in the illustrated embodiment, the slots 160 extend through the flange 154 and at least partially into the housing 152.

In this embodiment, the proximal anchor 150 includes four teeth or flanges 158, which are positioned near the proximal end of the anchor 150. In modified embodiments, the proximal anchor 150 may include more or less teeth and/or the teeth may be positioned more distally or proximally on the anchor 150. It should also be appreciated that these retention structures may be configured such that the proximal anchor 150 may be proximally and/or distally advanced with rotation by providing for a screw like configuration between the retention structures.

Figure 6E:
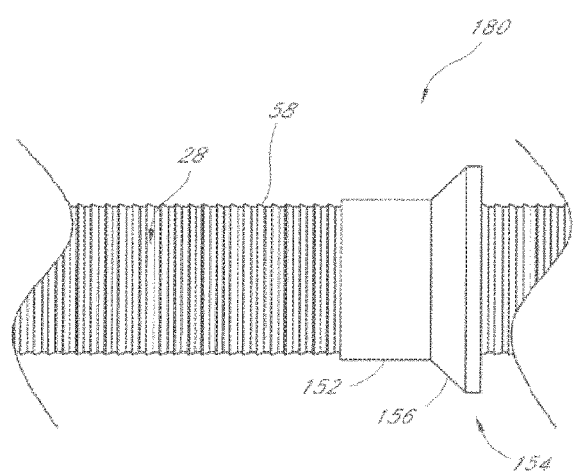
FIG. 6E is a cross-sectional view of another embodiment of a proximal anchor for the bone fixation device of FIG. 2.
Figure 6F:
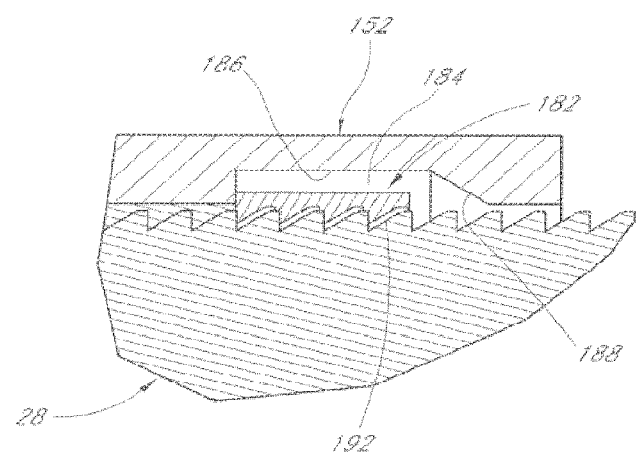
FIG. 6F is a cross-sectional view of the proximal anchor of FIG. 6E.

Another embodiment of a proximal anchor 180 is illustrated in FIGS. 6E and 6F. As with the previous embodiment, the proximal anchor 180 may include a tubular housing 152 and a flange 154 with a bone contacting surface 156. In this embodiment, the complementary structure of the proximal anchor 180 comprises an annular ring 182, which is positioned within an annular recess 184 that is preferably positioned at the distal end of the tubular housing 152. The annular recess 184 includes a proximal portion 186 and a distal portion 188.

The proximal portion 186 is sized and dimensioned such that as the proximal anchor 180 is advanced distally over the body 28 the annular ring 182 can ride over the complementary retention structures 58 of the body 28. That is, the proximal portion 182 provides a space for the annular ring 182 can move radially away from the body 28 as the proximal anchor 180 is advanced distally. Preferably, the annular ring 182 is made from a material that provides sufficient strength and elasticity such as, for example, stainless steel or titanium. The annular ring 182 is preferably split such that it can be positioned over the body 405. In the illustrated embodiment, the annular ring 182 includes a plurality of teeth 192 although in modified embodiments the annular ring 182 may be formed without the teeth.

The distal portion 188 of the recess 184 is sized and dimensioned such that after the proximal anchor 180 is appropriately tensioned the annular ring 192 becomes wedged between the body 28 and an angled engagement surface of the distal portion 188. In this manner, proximal movement of the proximal anchor 180 with respect to the body is prevented. Although not illustrated, it should be appreciated that in modified embodiments, the ring 192 can be formed without a gap. Other embodiments and further details of the proximal anchor described above can be found in U.S. patent application Ser. No. 09/990,587, filed Nov. 19, 2001, which is hereby incorporated by reference herein.

With reference back to FIGS. 2-4, in the illustrated embodiment, the contacting surface 68 of the flange 44 is tapered and generally faces the outer surface of the bone, fixation rod, and/or plate. In other embodiments, the bone contacting surface 69 can reside in or approximately on a plane, which is perpendicular with respect to the longitudinal axis of the body 28. In other embodiments, other angular relationships between the bone contacting surface 68 of the flange 66 and the longitudinal axis of the body 28 and housing 52 may be utilized, depending upon the anticipated entrance angle of the body 28 and associated entrance point surface of the bone.

The clinician may be provided an array of proximal anchors 50 of varying angular relationships between the contacting surface 68 and the longitudinal axis of the body 28 and housing 52 (e.g., 90°, 100°, 110°, 120°, and 130°). A single body 28 can be associated with the array such as in a single sterile package. The clinician upon identifying the entrance angle of the body 28 and the associated entrance point surface orientation can choose the anchor 50 from the array with the best fit angular relationship, for use with the body 28.

Figure 8:
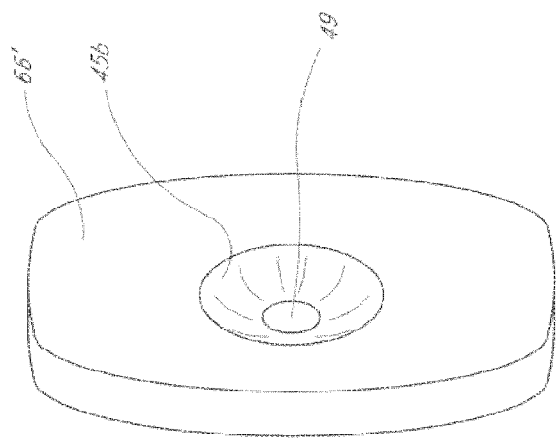
FIG. 8 is a front perspective view of the proximal anchor plate of FIG. 7.
Figure 7:
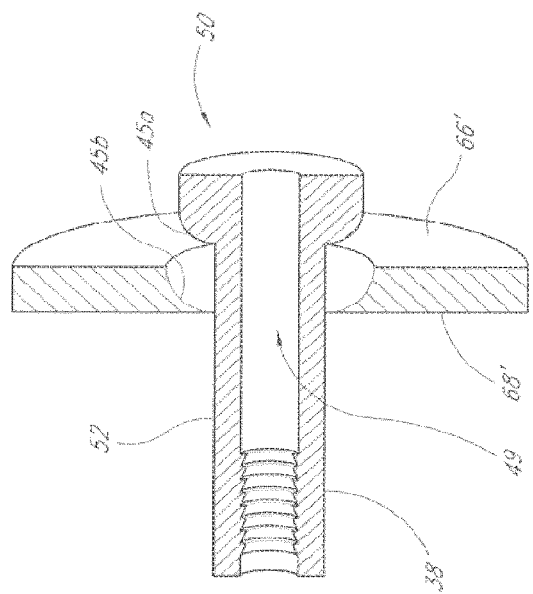
FIG. 7 is a cross sectional view through an angularly adjustable proximal anchor plate.
Figure 13:
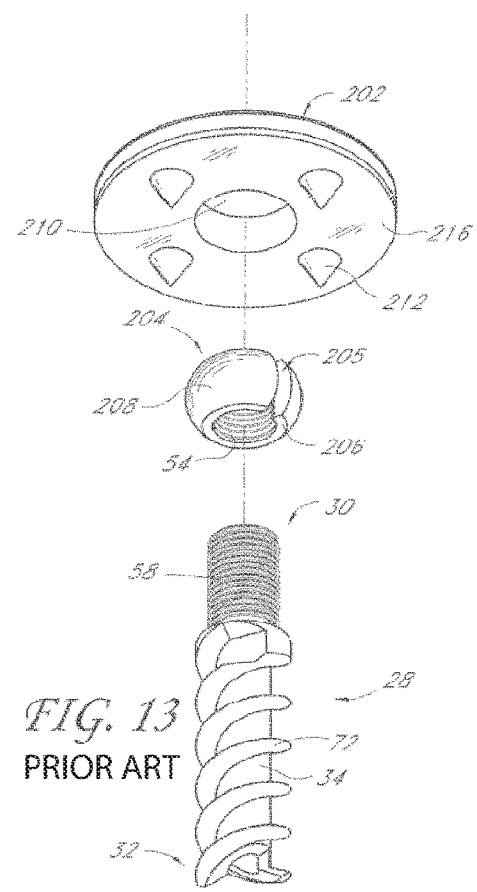
FIG. 13 is an unassembled bottom perspective view of the bone fixation device of FIG. 9.

In accordance with a modified arrangement, illustrated in FIGS. 7 and 8, the proximal anchor 50 may be used with a washer 66' that is angularly adjustable with respect to the longitudinal axis of the body 28. More specifically, in this embodiment, the proximal anchor 50 and the washer 66' include corresponding semi-spherical or radiused surfaces 45a and 45b. The surface 45b surrounds an aperture 49 in the washer 66. This arrangement allows the proximal anchor 50 to extend through and pivot with respect to the washer 66'. As such, the angular relationship between the bone contacting surface 68' of the washer 66' and the longitudinal axis of the body 28 can vary in response to the entrance angle.

FIGS. 9-13 illustrate another embodiment of a bone fixation device 200 with an angularly adjustable proximal anchor 202. In this embodiment, similar reference numbers are used to identify components that are similar components described above.

The bone fixation device 200 comprises a body 28 that extending between a proximal end 30 and a distal end 32. The distal end 32 of the body is provide with a bone anchor 34 as described above. The illustrated body 28 is cannulated; however, it should be appreciated that in modified embodiments the body 28 can be solid. The proximal end of the anchor is provided with a hexagonal recess, which can be used in combination with a rotational tool to rotate the body 28. Of course, modified embodiments may use a variety of different male or female anti-rotational couplings.

The illustrated fixation device includes an annular flange 202 and proximal anchor 204. As with the proximal anchor described above, the proximal anchor 204 defines a housing 206 that is axially distally moveable along the body 28. Complementary locking structures 54, 58 on the housing 206 and the body 28 such as threads or ratchet like structures resist proximal movement of the anchor 204 with respect to the body 28 under normal use conditions. In some embodiments, the complementary locking structures 54, 48 may permit the anchor 204 to be axially advanced along the body 28 by rotation. In other embodiments, the complementary locking structures 54, 58 may permit the anchor 204 to be axially advanced along the body 24 without rotation. The illustrated proximal anchor 204 also includes a gap 205 such that the illustrated anchor 204 forms a split ring collar. In modified embodiments, the proximal anchor 204 can be formed without the gap 205.

Figure 12:
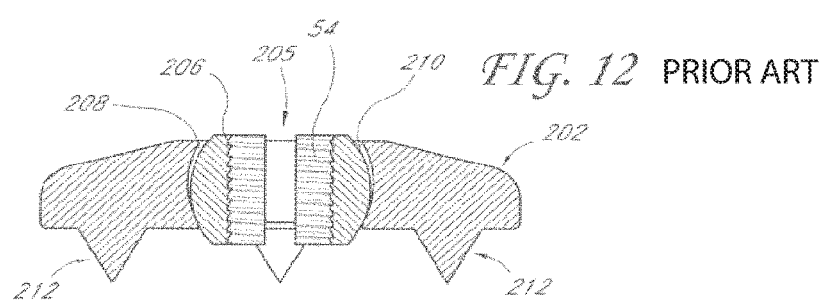
FIG. 12 is a cross-sectional view of the flange and proximal anchor of the bone fixation device of FIG. 11.

The proximal anchor 204 preferably includes a smooth and more preferably rounded or spherical outer surface portion 208, which is configured to fit within a corresponding smooth and preferably rounded recessed portion 210 in the flange 202. As such, as shown in FIG. 12, when the proximal anchor 204 is positioned in the flange 202, the flange 202 resists distal movement of the proximal anchor 204 while permitting at least limited rotation of between the proximal anchor 204 and the flange 202. As such, the illustrate arrangement allows for angular movement of the flange 202 with respect to the anchor 204 to accommodate variable anatomical angles of the bone surface. In such applications, the flange 202 may seat directly against the outer surface of the bone. Because the outer surface of the bone may be non-planar and/or the angle of insertion may not be perpendicular to the outer surface of the bone, a fixed flange may contact only a portion of the outer surface of the bone. This may cause the bone to crack due to high stress concentrations. In contrast, the angularly adjustable flange 202 can rotate with respect to the body and thereby the bone contacting surface may be positioned more closely to the outer surface. More bone contacting surface is thereby utilized and the stress is spread out over a larger area. In addition, the flange 202, which has a larger diameter than the proximal anchor 50, effectively increases the shaft to head diameter of the fixation device, thereby increasing the size of the loading surface and reducing stress concentrations.

In the illustrated embodiment, the flange 202 includes a plurality of bone engagement features 212, which in the illustrated embodiment comprises one or more spikes 212 positioned on a contacting surface 216 of the flange 202. The spikes 212 provide additional gripping support especially when the flange 202 is positioned against, for example, uneven bone surfaces and/or soft tissue. However, it should be appreciated that in modified embodiments the flange 202 may be formed without the bone engagement features 212. Other structures for the bone engagement feature 212 may also be used, such as, for example, ridges, serrations etc. The illustrated embodiment also includes a tapered upper surface 214 that in certain embodiments may be flat.

FIGS. 14 and 15 illustrate a modified embodiment of the angularity adjustable fixation device 200. In this embodiment, the proximal anchor 204' includes an upper portion 211 and a lower portion 213. The upper portion 211 is configured as described above with respect to the housing. The lower portion in the illustrated embodiment is generally tubular and a generally smaller diameter than the upper portion. The lower portion includes complementary retention structures 54 and generally provides the fixation device with a greater range of adjustable compression and additional retention structures as compared to the previous embodiment.

In one arrangement, where the device is inserted directly across the facture (described below) a fixation device (such as described above) can be inserted across a facture in a spine (e.g., a pars fracture). In certain of these arrangements, the distal anchor of the fixation device may be inserted into a first bone portion, across the fracture and into a second bone portion. The proximal anchor may be carried by the fixation device prior to advancing the distal anchor across the fracture, or may be attached following placement of the distal anchor within the spine.

Once the anchor is in the desired location, proximal traction can be applied to the proximal end 30 of body 28, such as by conventional hemostats, pliers or a calibrated loading device, while distal force is applied to the proximal anchor. In this manner, the proximal anchor is advanced distally with respect to the body until the proximal anchor fits snugly against the outer surface of a portion of a spine or an intermediate device (fixation plate/rod/washer) and the distance between the proximal and distal anchors has been shortened. Tensioning of the fixation device can be accomplished by tactile feedback or through the use of a calibration device for applying a predetermined load on the implantation device. As explained above, one advantage of the structure of the illustrated embodiments is the ability to adjust compression independently of the setting of the distal anchor 34 within the bone and with respect to the fracture. In some embodiments, advancement of the proximal anchor can done by distally pushing the anchor over the body 28 or the distal advancement can combine proximal retraction of the body with respect to the anchor and/or distal movement of the anchor or sequenced to shorten the distance between the two components. As described herein, in some arrangements, the proximal anchor can be rotated or threaded onto the pin or body and/or so that that the proximal anchor can be removed by rotation in some arrangements.

Following e.g., tensioning of the proximal anchor, the second portion 38 of the body 28 is can be detached from the first portion 36 and removed. In the an embodiment, this involves rotating the second portion 38 with respect to the first portion via the coupling 70. In other embodiment, this may involve cutting the proximal end of the body 28. For example, the proximal end of the body may be separated by cauterizing. Cauterizing may fuse the proximal anchor 50 to the body 32 thereby adding to the retention force between the proximal anchor 50 and the body 28. Such fusion between the proximal anchor and the body may be particularly advantageous if the pin and the proximal anchor are made from a bioabsorbable and/or biodegradable material. In this manner, as the material of the proximal anchor and/or the pin is absorbed or degrades, the fusion caused by the cauterizing continues to provide retention force between the proximal anchor and the body.

Following or before removal of the second portion 38 of each body 28, additional fixations devices may be implanted and/or additional stabilization implants (e.g., rods, plates, etc.) may be coupled to the body. The access site may be closed and dressed in accordance with conventional wound closure techniques.

In a an arrangement, the second portion 38 may form part of the driving device, which is used to rotate the proximal anchor 50 and thus cancellous bone anchor 34 into the vertebrae. The second portion 38 is used to apply proximal traction. After appropriate tensioning, the second portion 38 can be de-coupled from the first portion 36 and removed with the driving device.

In the foregoing variation, the second portion 38 can be connected to a rotatable control such as a thumb wheel on the deployment device. A container may be opened at the clinical site exposing the proximal end of the implant, such that the distal end of the second portion 38 may be removably coupled thereto. Proximal retraction of the hand tool will pull the implant out of its packaging. The implant may then be positioned within the aperture in the bone, rotated to set the distal anchor, and the hand piece may be manipulated to place proximal traction on the second portion 38 while simultaneously distally advancing the proximal anchor. Following appropriate tensioning, the second portion 38 may be disengaged from the implant, and removed from the patient. In the example of a threaded engagement, the second portion 38 may be disengaged from the implant by rotating a thumb wheel or other rotational control on the hand piece. In an embodiment, such as where the second portion 38 comprises a pull wire, following appropriate tensioning across the fracture, a first end of the pull wire is released such that the pull wire may be removed from the implant by proximal retraction of the second end which may be attached to the hand piece.

FIG. 16A-16J illustrate various embodiments of an implant for pars defect repair comprising a bone compression screw. In each of FIGS. 16A-16J, the implant 300 includes a first anchor 312 which can be substantially identical to the fixation device 12 described above and/or can use features and sub-combinations from various embodiments described herein. The first anchor 312 can include a body 328 extending between a proximal end 330 and a distal end 332. The distal end 332 comprises a helical locking structure 372 for engaging bone. Proximal end 330 comprises a proximal anchor 350 that is axially distally moveable along the body 328 to permits compression of the first anchor 312. The proximal anchor 350 comprises a housing 352 such as a tubular body with complementary retention structures configured to engage ridges 360 on the body 328. A flange 366 is proximal to the housing 352. However, in contrast to the fixation device 12 described above, here the first anchor 312 includes a flange 366 which is either coupled to or integrally formed with a bridge extending to the second anchor, as described in more detail below with respect to various embodiments.

As described above with respect to the fixation device 12, the proximal anchor 350 can be advanced once the helical locking structure 372 has been inserted, thereby shortening the first anchor 312 and providing compression as the flange 366 presses against bone, a plate, or other object. With respect to FIGS. 16F-16J, the housing 352 is illustrated, while the remainder of the first anchor 312 is omitted for simplicity. In use, the components of the first anchor 312 can be substantially identical or similar to those shown in FIGS. 16A-16E.

Figure 16A:
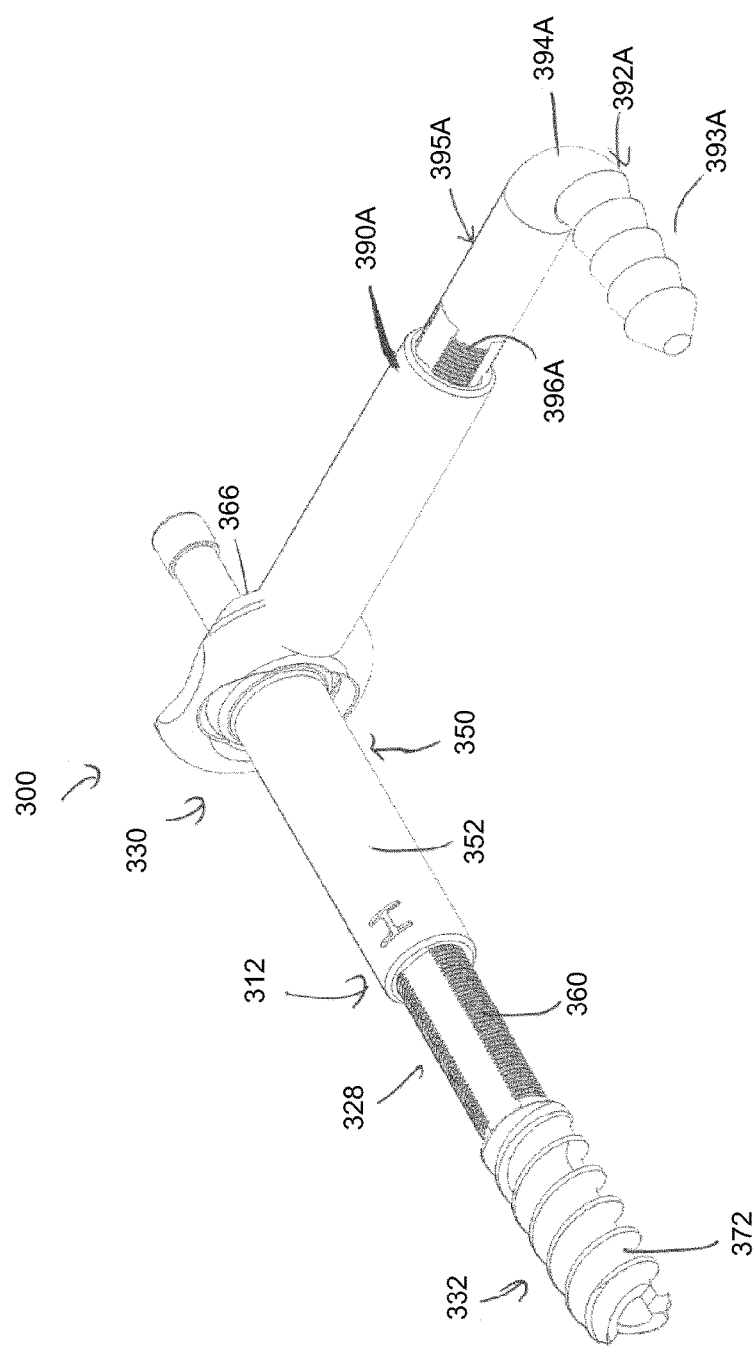

With respect to FIG. 16A, the flange 366 is integrally formed with the bridge 390a, which is coupled to the second anchor 392a. The bridge 390a forms a tubular extension laterally away from the first anchor 312. In the illustrated embodiment, the bridge 390a extends along an axis substantially perpendicular to the longitudinal axis of the first anchor 312. The bridge 390a includes a lumen configured to receive a portion of the second anchor 392a. As shown, the second anchor 392a includes a distal portion 393a with ridges formed annularly around its axis. The distal portion 393a is configured to be inserted into bone, either by self-tapping or by entering through a pre-formed hole in bone. The second anchor 392a includes an elbow 394a connecting the distal portion 393a with the lateral portion 395a, which includes a plurality of ridges 396a. These ridges 396a can be complementary to ridges (not shown) on the interior of the bridge 390a, thereby allowing the second anchor to be slidably moved within the bridge 390a, thereby extending the distance between the first anchor 312 and the second anchor 392a. In some embodiments, rotational movement between the second anchor 392a and the bridge 390a can be restricted, for example by the use of flanges on the lateral portion 395a of the second anchor 392a. In other embodiments, the second anchor 392a can be rotated with respect to the bridge 390a, and therefore with respect to the first anchor 312. In use, position of the second anchor 392a can be adjusted prior to, during, or after insertion of the implant.

Figure 16B:
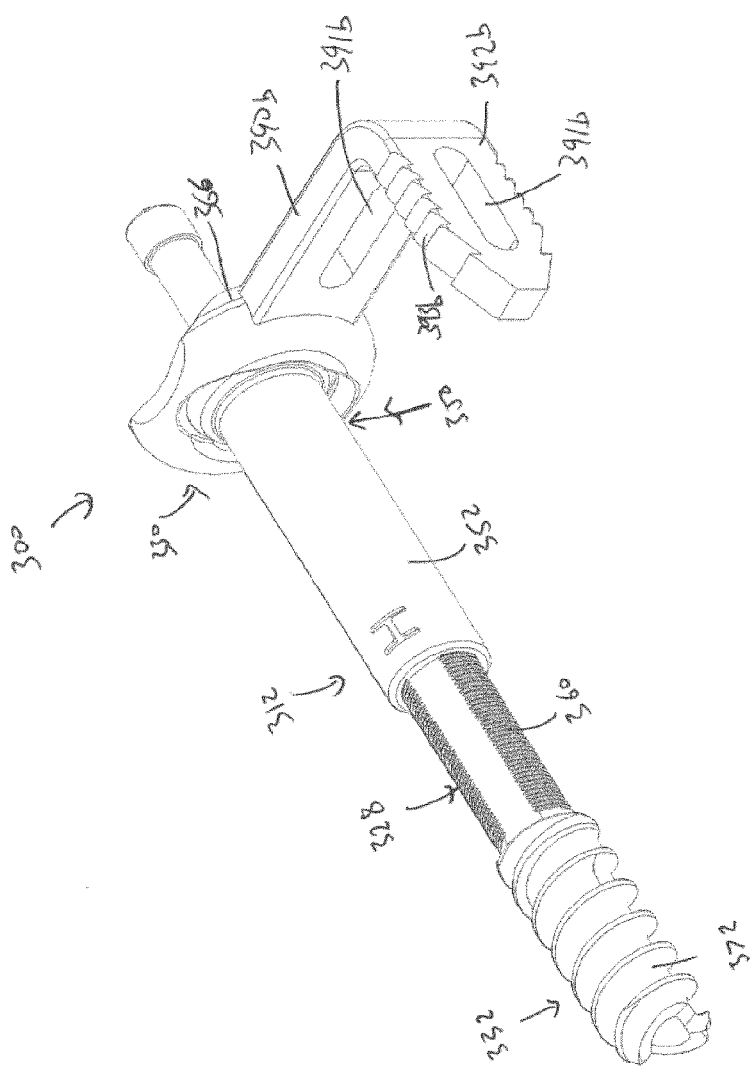

Turning now to FIG. 16B, in the illustrated embodiment, the flange 366 is integrally formed with the bridge 390b and the second anchor 392b. The second anchor 392b extends substantially parallel to a longitudinal axis of the first anchor 312. In other embodiments, the second anchor 392b may extend along an axis that is divergent with or convergent with the axis of the first anchor 312. As illustrated, both the bridge 390b and the second anchor 392b include fenestrations 391b. In use, these fenestrations 391b can receive bone cement, bone growth promoting materials, or other material, prior to, during, or after insertion of the implant 300 into the body. In some embodiments, the use of such bone cement or other material can promote osseointegration of the implant 300 with the vertebra and can promote fusion of the pars fracture. As illustrated, the second anchor 392b includes a plurality of ridges 393b, which can aid retention of the second anchor 392b within the bone.

Figure 16C:
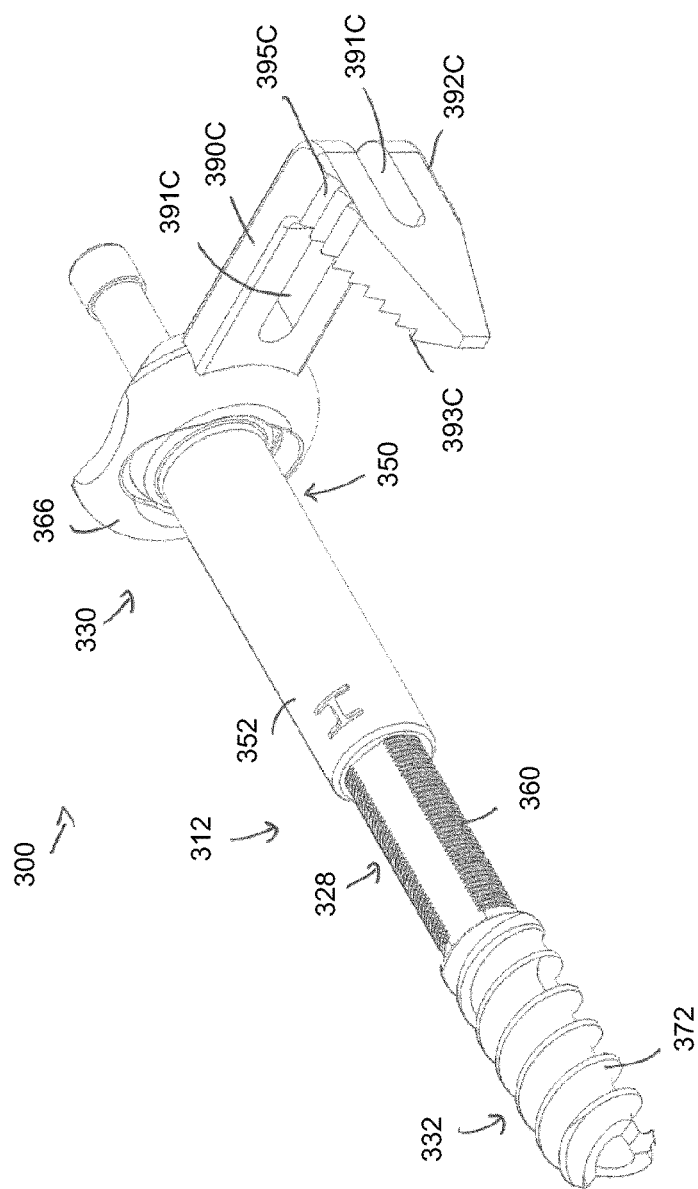

With respect to FIG. 16C, in the illustrated embodiment, the flange 366 is integrally formed with the bridge 390c and the second anchor 392c. The bridge 390c and second anchor 392c are similar to bridge 390b and second anchor 390b described with respect to FIG. 16B, including an fenestration 391c configured to receive bone cement, bone growth promoter, or other material. The second anchor 392c includes a plurality of ridges 393c, here only present on the inner side of the second anchor 392c, facing the first anchor 312 at the lower portion of the second anchor 392c, with additional ridges 395c disposed on lateral surfaces higher up on the second anchor 392c.

Figure 16D:
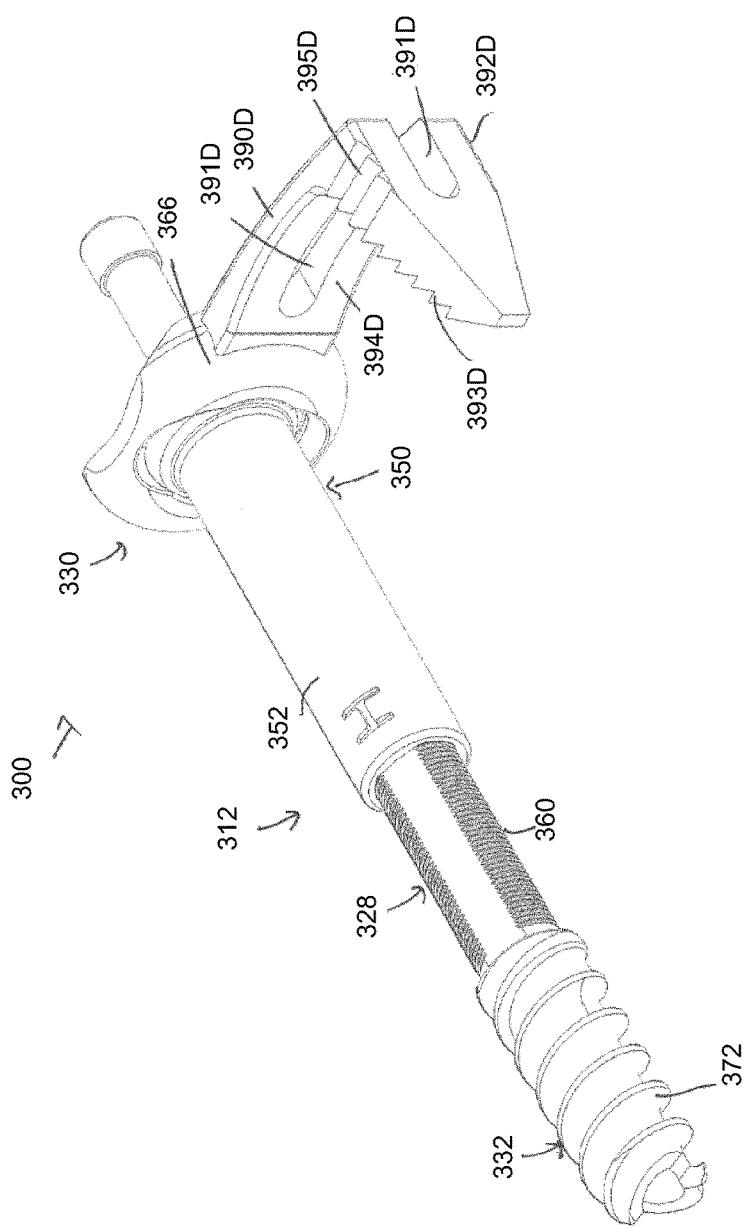

As illustrated in FIG. 16D, the flange 366 can be integrally formed with the bridge 390d and the second anchor 392d, in a manner similar to the bridge 390c and second anchor 392c shown in FIG. 16C. Here, however, the bridge 390d includes a curved lower surface 394d. The bridge 390d and second anchor 392d include an fenestration 391d configured to receive bone cement, bone growth promoter, or other material. The second anchor 392d includes a plurality of ridges 393d, on the inner side of the second anchor 392d, facing the first anchor 312 at the lower portion of the second anchor 392d, with additional ridges 395d disposed on lateral surfaces higher up on the second anchor 392d. The curved surface shape of the bridge 390d can be configured such that, upon insertion of the second anchor 392d into bone, there is compression provided inwardly by the second anchor 392 pressing towards the first anchor 312.

Figure 16E:
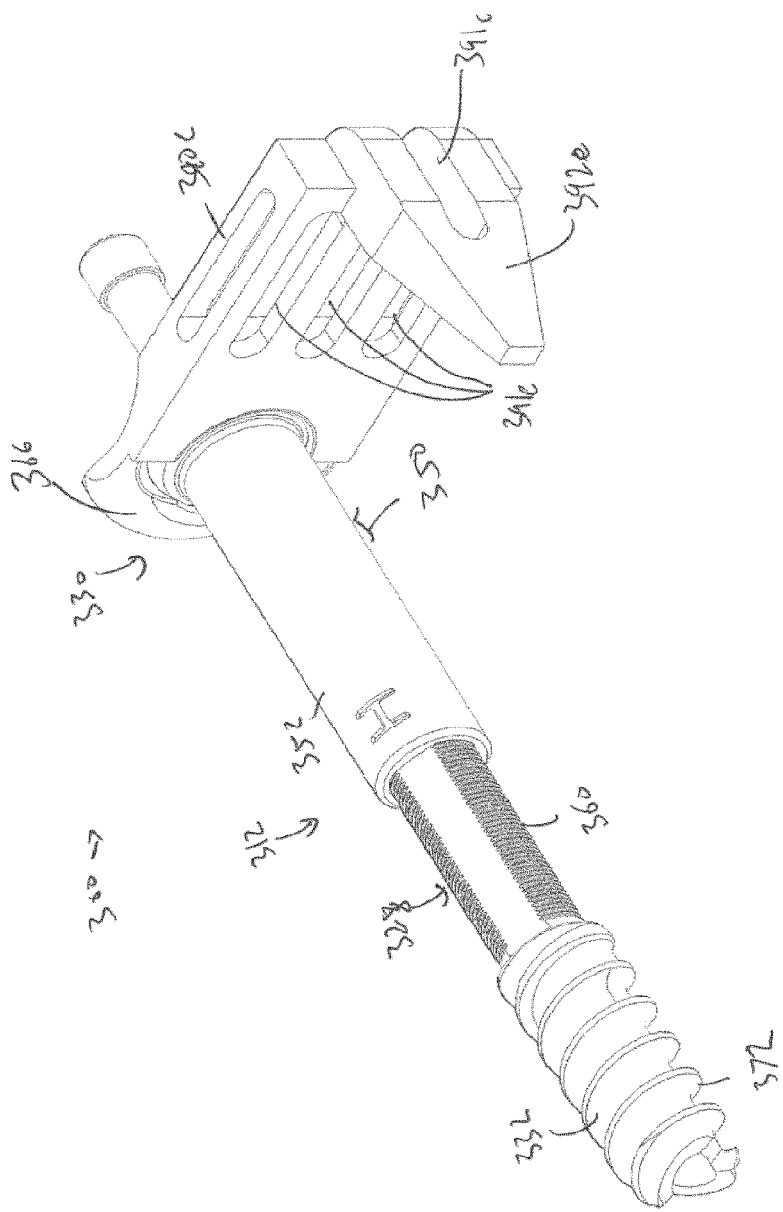

Turning now to FIG. 16E, the flange 366 can be integrally formed with the bridge 390e and the second anchor 392e. Here, the bridge 390e includes a plurality of fenestrations 391e configured to receive bone cement, bone growth promoter, or other material, while the second anchor 392e includes a single fenestration 391e. The second anchor 392e takes the form of a spike which tapers as it extends away from the bridge 390e. The wider bridge 390e, compared with the embodiments illustrated in FIGS. 16B-16D, can allow for the use of more bone cement or other material, and additionally provides more surface area contact between the bridge 390e and the vertebra upon insertion of the implant.

Figure 16F:
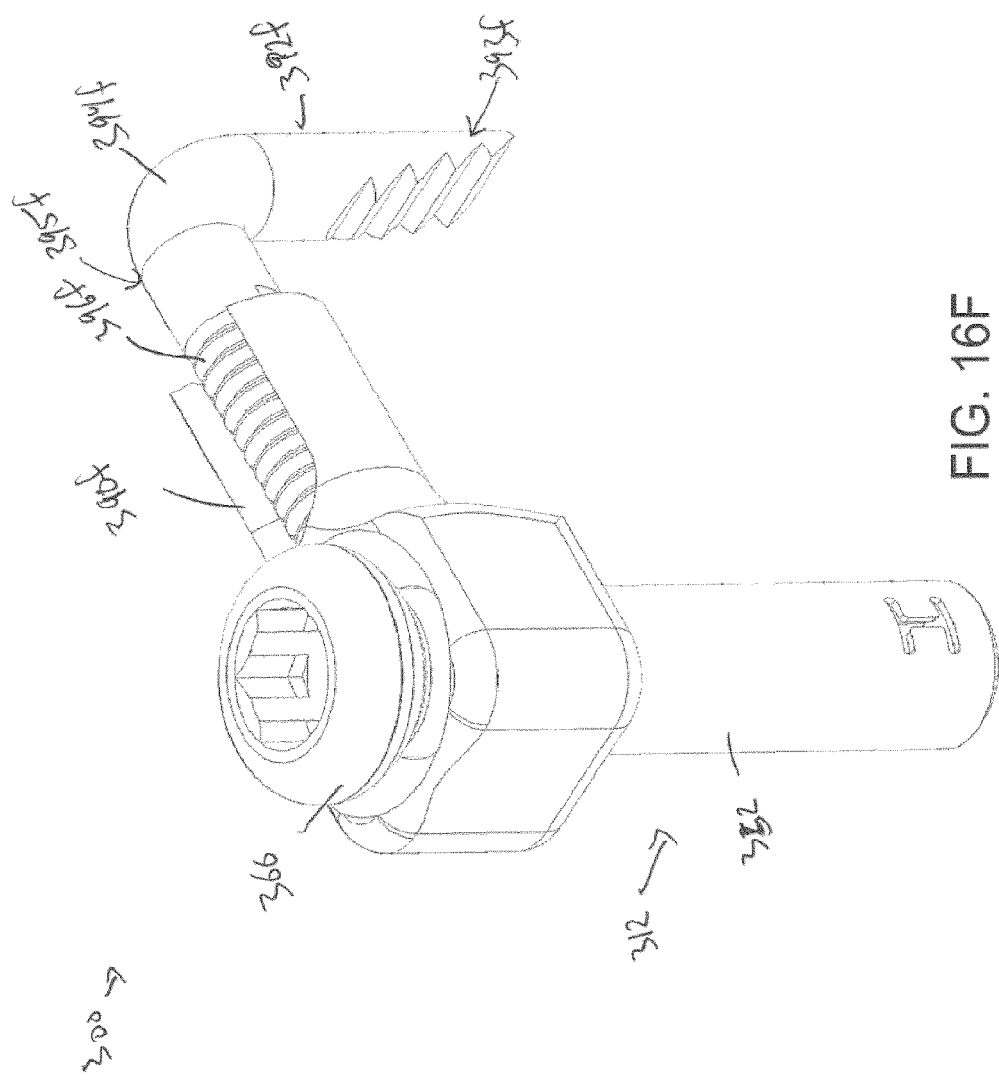

As shown in FIG. 16F, the flange 366 can be integrally formed with the bridge 390f, which is coupled to the second anchor 392f The bridge 390f forms a semi-tubular extension laterally away from the first anchor 312. In the illustrated embodiment, the bridge 390f extends along an axis substantially perpendicular to the longitudinal axis of the first anchor 312. The bridge 390f includes a lumen configured to receive a portion of the second anchor 392f As shown, the second anchor 392f includes a distal portion 393f with ridges formed on an inner surface substantially facing the first anchor 312. The distal portion 393f is configured to be inserted into bone, either by self-tapping or by entering through a pre-formed hole in bone. The second anchor 392f includes an elbow 394a connecting the distal portion 393f with the lateral portion 395f, which includes a plurality of ridges 396f These ridges 396f can be complementary to ridges (not shown) on the interior of the bridge 390f, thereby allowing the second anchor to be slidably rotated within the bridge 390f Additionally, the ridges 396f can be mated with those complementary ridges in the bridge 390f at a number of different positions, allowing for different distances to be achieved between the first anchor 312 and the second anchor 392f One the coupled together, with the complementary ridges of the bridge 390f engaged with the ridges 396f, the second anchor 392f can be rotated freely with respect to the bridge 390f, and therefore with respect to the first anchor 312. In use, position of the second anchor 392f can be adjusted prior to, during, or after insertion of the implant.

Figure 16G:
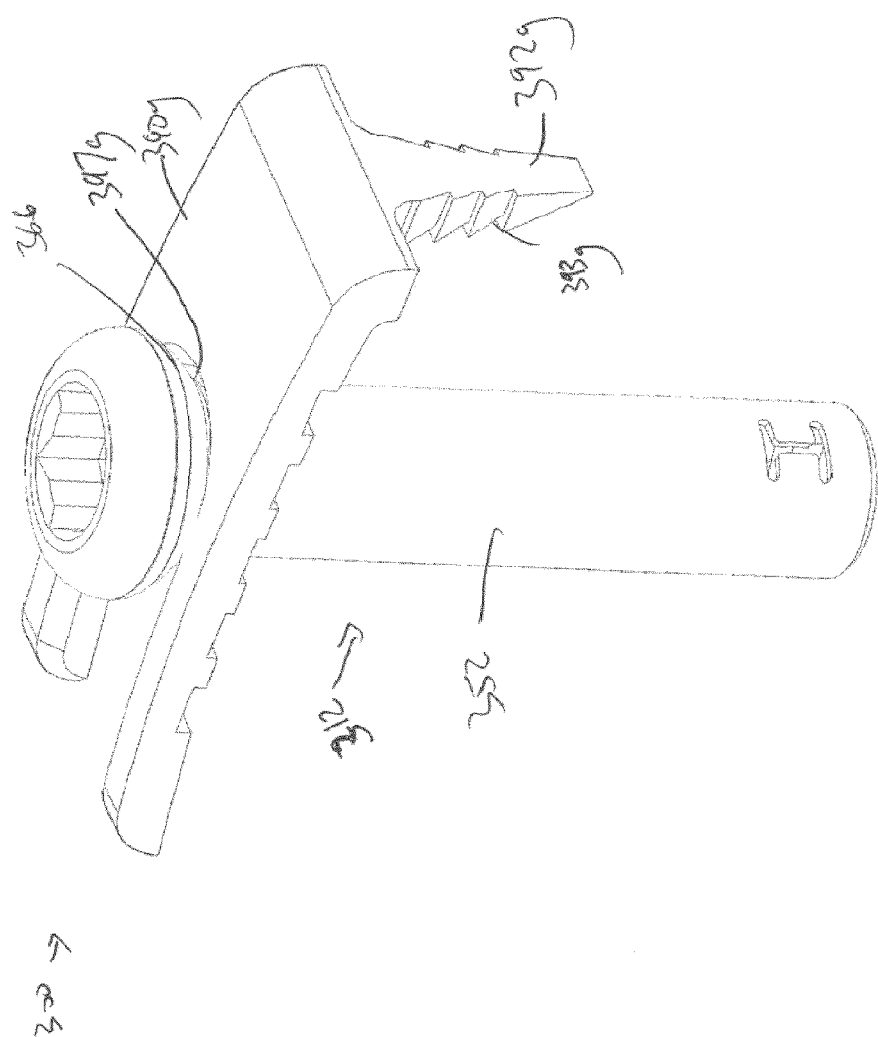

With respect to FIG. 16G, the bridge 390g can be coupled to the housing 352 just below the flange 366, and the second anchor 392 extends outwardly from the bridge 390g. The second anchor 392g takes the form of a spike having ridges 393g formed on some but not all of the side surfaces of the second anchor 392g. The bridge 390g is a plate having an opening 397g configured to slidably receive the flange 366 of the first anchor 352. In use, the position of the second anchor may be determined first, and may be inserted into the bone. The first anchor 312 may then be inserted and, upon tightening and compression of the first anchor 312, the bridge 390g is pressed downwardly towards the bone, which further compresses the second anchor 392g.

Figure 16H:
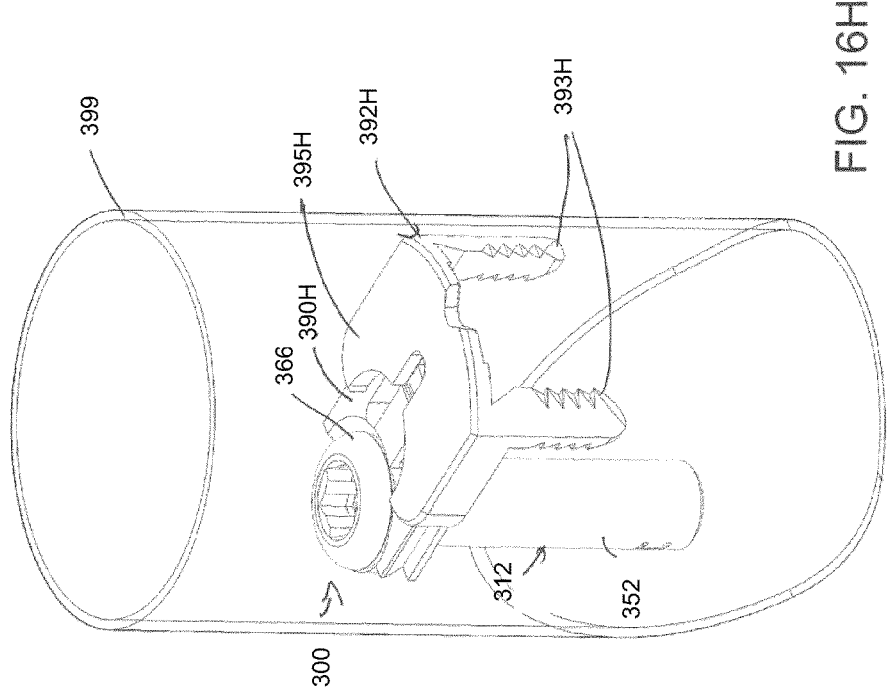
Figure 16I:
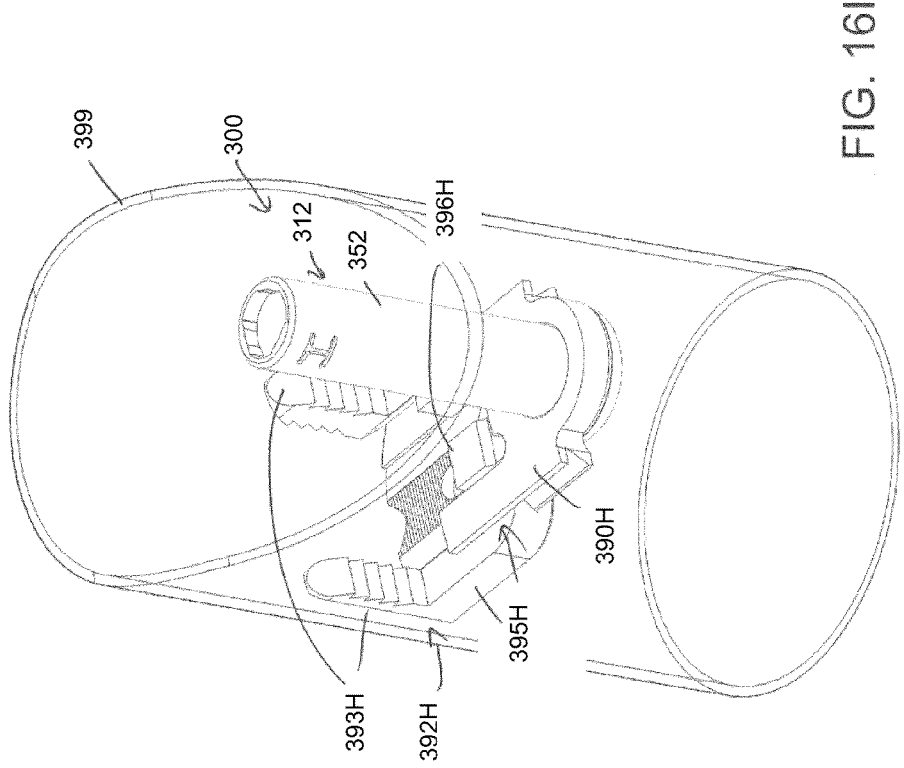

FIGS. 16H and 16I illustrate another embodiment of an implant 300 disposed within a cannula 399. Here, the second anchor 392h takes the form of a plate 395h which is slidably engaged with the bridge 390h. Two distal portions 393h of the second anchor 392h extend downwardly from the plate 395h of the second anchor 392h. As illustrated, the distal portions 393h each include ridges, which can aid retention of the distal portions 393h upon insertion into bone. The plate 395h of the second anchor 392h can be slidably engaged with the bridge 390h through a ratchet mechanism 396h as shown in FIG. 16I. In use, adjustment of the ratchet mechanism can allow for the relative positions of the first anchor 312 and the second anchor 392h to be adjusted. The ratchet mechanism can allow for the second anchor 392h to be moved closer to the first anchor 312 by sliding incrementally, while movement of the second anchor 392h away from the first anchor 312 can be restricted until the ratchet mechanism 396h is released. This can allow for implant 300 to provide compression across the fracture after insertion, without the first anchor 312 and the second anchor 392h being moved away from one another once implanted.

Turning now to FIG. 16J, the implant 300 takes a similar form to that in FIGS. 16H and 16I. The second anchor 392j takes the form of a plate 395j which is slidably engaged with the bridge 390h. Two distal portions 393j of the second anchor 392j extend downwardly from the plate 395j of the second anchor 392*j*. As illustrated, the distal portions 393*j* each include threads, allowing for the distal portions 393 to be independently screwed into bone, which can aid retention of the distal portions 393*j* in the bone. The plate 395*j* of the second anchor 392*j* can be slidably engaged with the bridge 390*j* through a ratchet mechanism as described above with respect to FIGS. 16H and 16I.

FIGS. 17A-17B illustrate additional embodiments of an implant for spondylolysis repair. As shown in FIG. 17A, the implant 400 includes a first anchor 401, a second anchor 403, and a bridge 405 connecting the two anchors. Actuation of the rotary mechanism 407 can cause the first and second anchors 401 and 403 to be pivot toward one another to provide compression across a fracture. The first and second anchors 401 and 403 can rotate about the joints 409 and 411 at which they meet the bridge 405, such that the distal ends 413 and 415 of the first and second anchors 401 and 403 are moved closer to one another upon actuation of the compression mechanism. As illustrated, the first and second anchors 401 and 403 can take the form of curved spikes or posts having ridges or detents formed on one side. In various embodiments, the anchors may take other forms. In other embodiments, the first and second anchors 401 and 403 may be moved closer to one another by other actuator mechanisms. In some embodiments, the first and second anchors 401 and 403 can be moved towards one another linearly, rather than rotationally as illustrated here.

With respect to FIG. 17B, the implant 500 includes a first anchor 501, a second anchor 503 and a bridge 505 connecting the two anchors. Actuation of the compression mechanism 507 can allow for linear movement of the first and second anchors 501 and 503 toward one another, thereby providing compression across a fracture. The first and second anchors 501 and 503 can slide linearly within grooves of the bridge 505, such that the first and second anchors 501 and 503 remain substantially parallel during movement. As illustrated, the first and second anchors 501 and 503 can take the form of substantially straight spikes or posts having ridges or detents formed annularly around the anchors. In various embodiments, the anchors may take other forms. In other embodiments, the first and second anchors 501 and 503 may be moved closer to one another by other actuator mechanisms. In some embodiments, the first and second anchors 501 and 503 can be moved towards one another via pivoting or other relative movement, rather than linearly as illustrated here.

Figure 18A:
FIGS. 18A-18F illustrate various views of a compressible implant spanning a pars fracture.
Figure 18B:
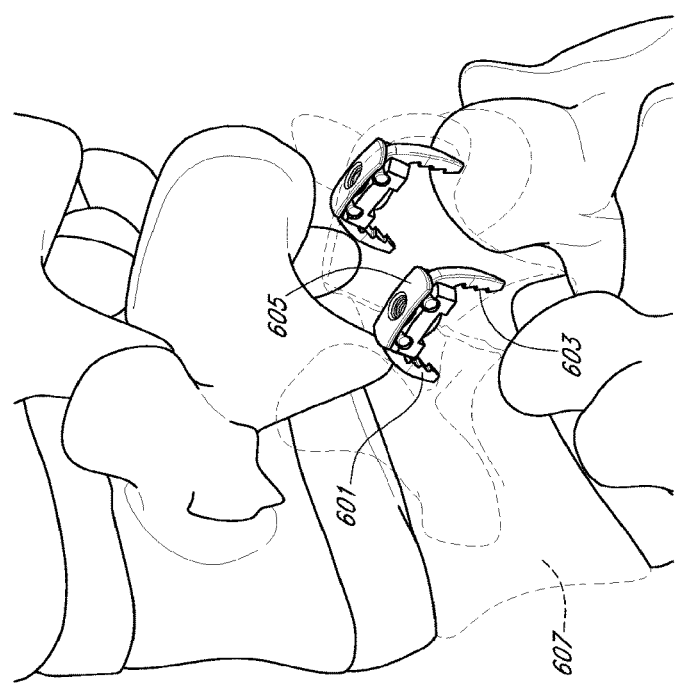
Figure 18C:
Figure 18D:
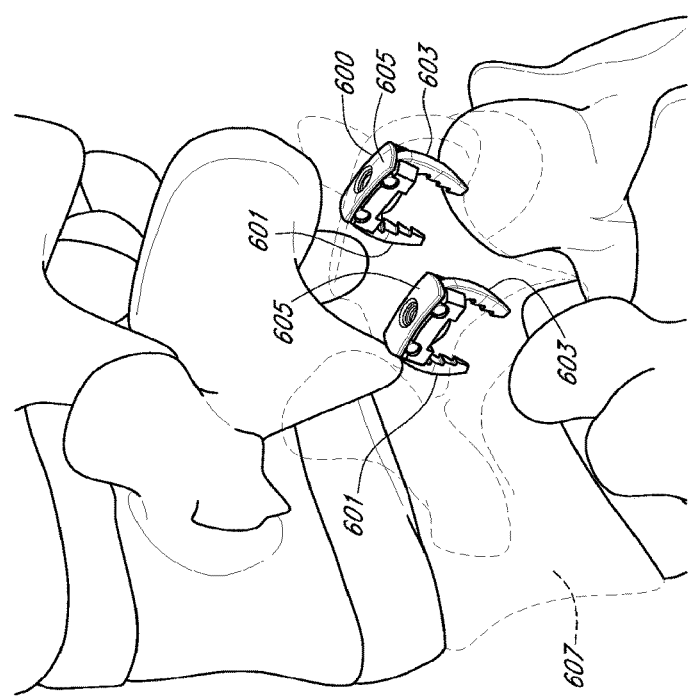
Figure 18E:
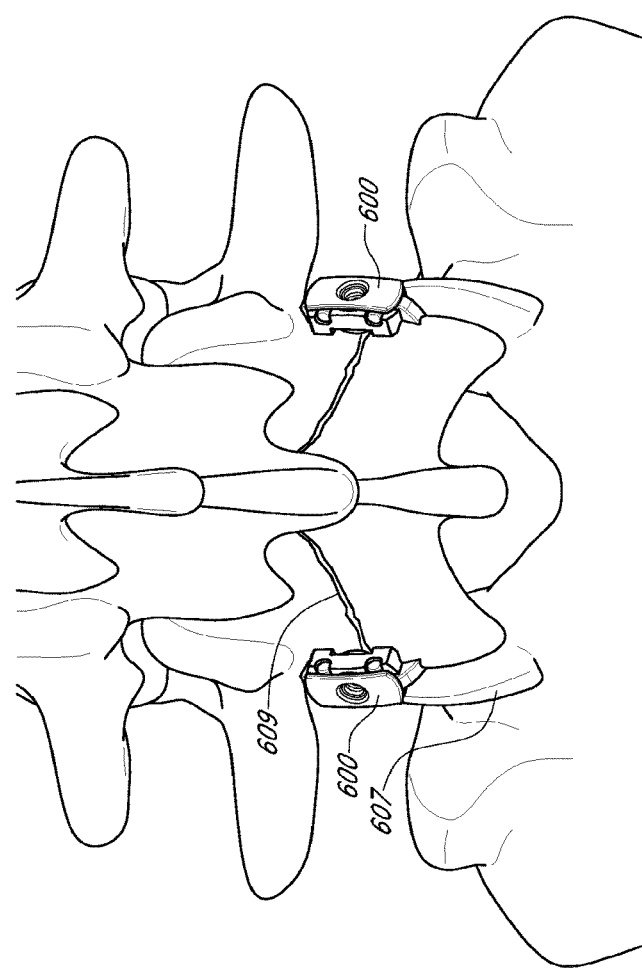
Figure 18F:
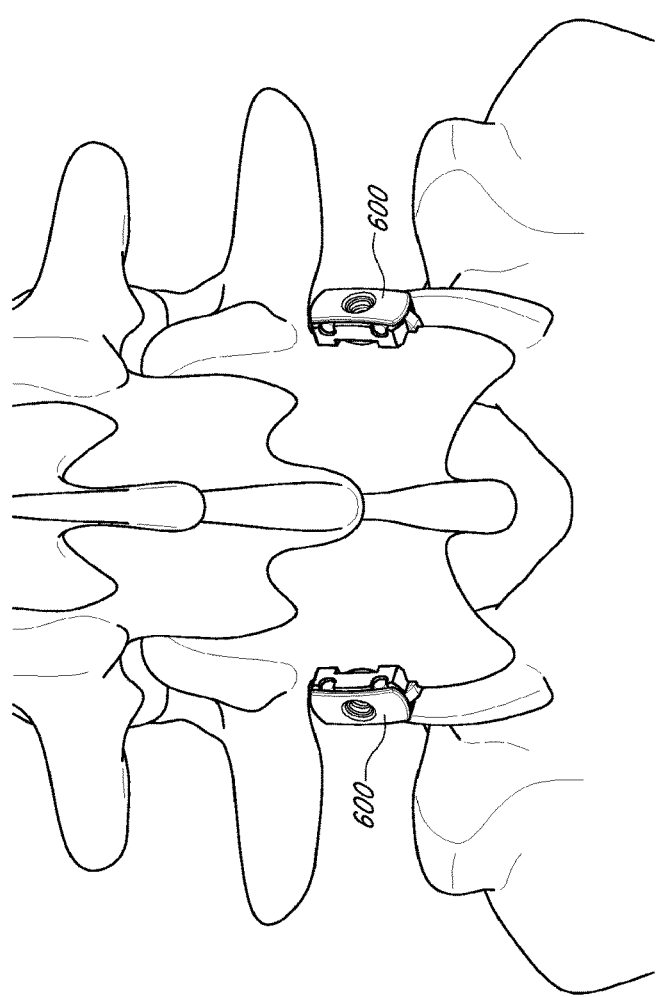

FIGS. 18A-18F illustrate various views of a compressible implant spanning a pars fracture. Compressible implant 600 includes a first anchor 601, a second anchor 603, and a bridge 605 coupling the two together. The implant 600 is shown with the first anchor 601 implanted into the vertebra 607 superior to the fracture 609, with the second anchor 603 implanted into the vertebra 607 inferior to the fracture 609. FIG. 18A illustrates the implant spanning the fracture, while FIG. 18B provides the view with the vertebra shown in transparent view. FIGS. 18C and 18D illustrate solid and transparent views, respectively, of the vertebra after the fracture 607 has healed. FIGS. 18E and 18F illustrate a modified approach in which the implant 600 is inserted via a dorsolateral trajectory, rather than the posterior approach shown in FIGS. 18A-18D. In the dorsolateral approach, the compressible staple 600 can be aligned along the ridge of the pars interarticularis, as shown in FIGS. 18E and 18F.

In some embodiments, a staple can be compressed across the fracture, during or after insertion of the implant, to compress the two parts of the vertebra together. For example, the implant may take the form of the compressible staple shown in FIG. 17A, in which case actuating the rotary mechanism can cause the first and second anchors to pinch together. In some embodiments, bone graft, bone cement, or bone growth promoters can be put in the fracture, or onto or around the implant itself. Although these drawings illustrate bilateral insertion of the implants, in other embodiments a single implant may be employed unilaterally.

Figure 19A:
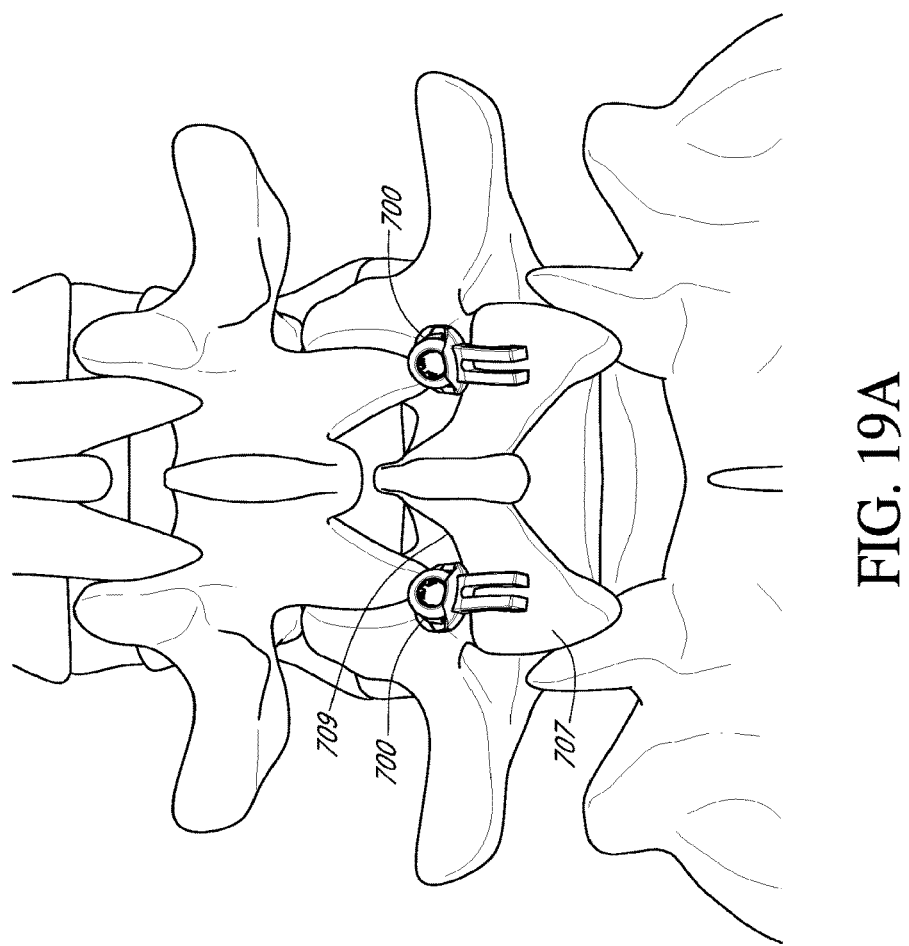
FIGS. 19A-19C illustrate various views of an implant spanning a pars fracture, the implant comprising a bone compression screw and an angular spike.
Figure 19B:
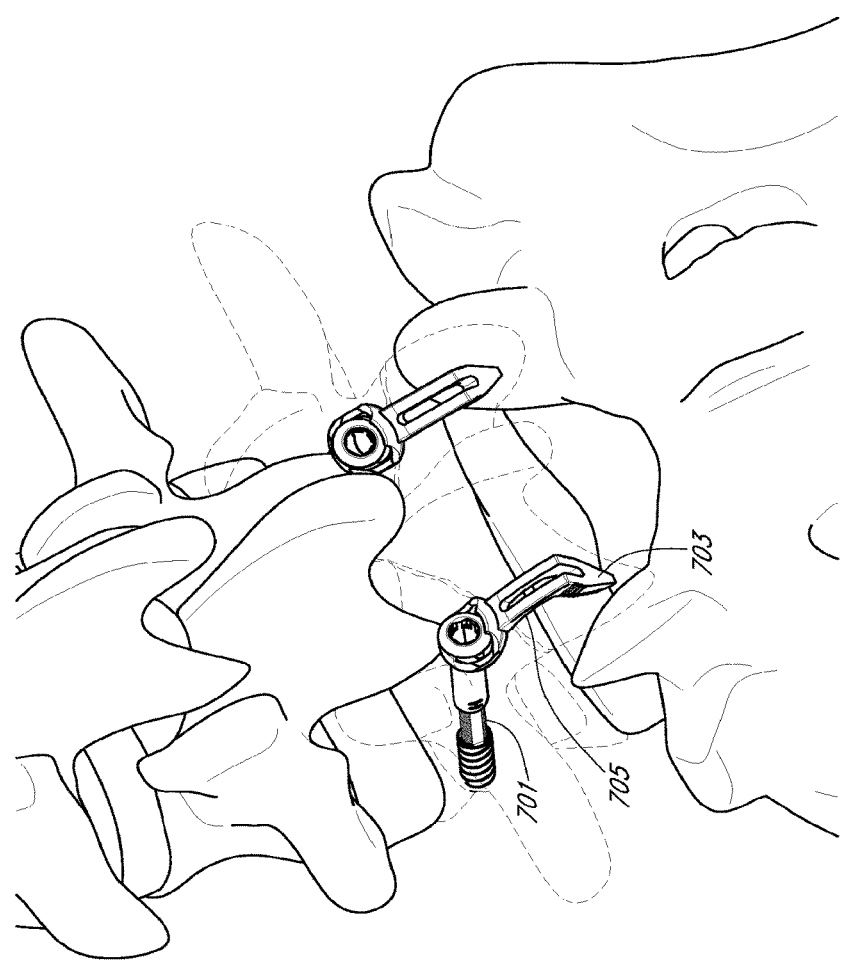
Figure 19C:
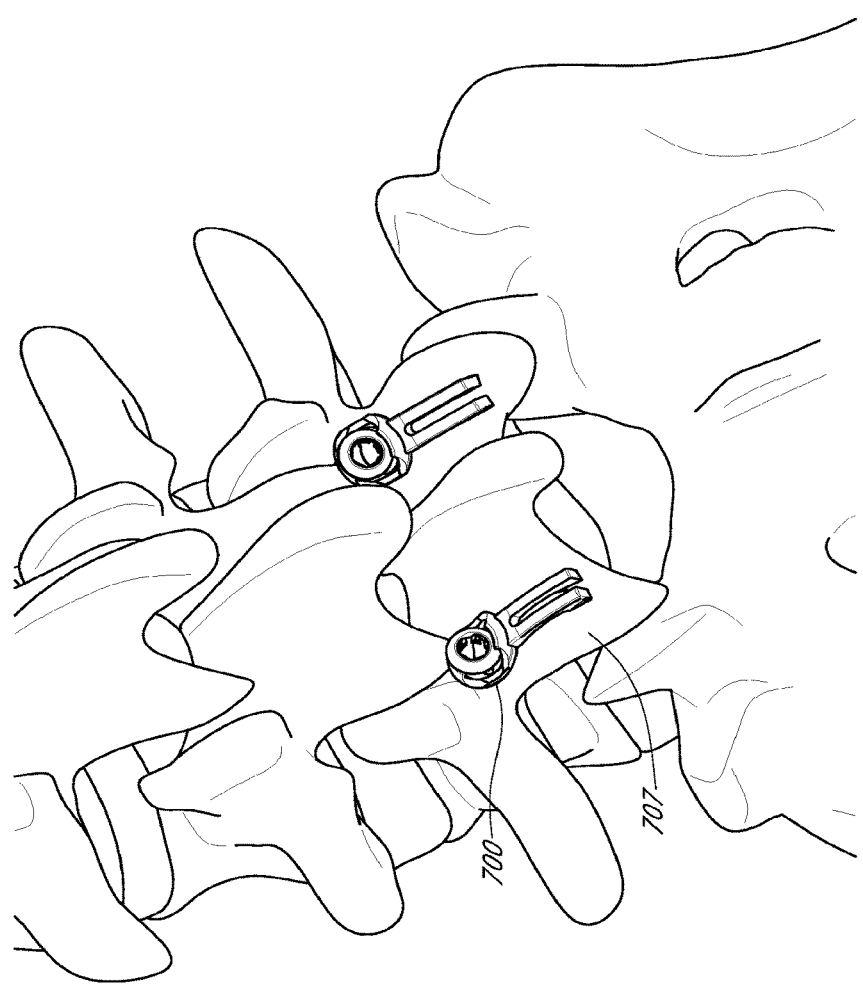

FIGS. 19A-19C illustrate various views of an implant spanning a pars fracture, the implant comprising a bone compression screw and an angular spike. The implant 700 includes a first anchor 701, which takes the form of a bone screw, and a second anchor 703, which takes the form of an angular spike, with the two anchors coupled together via a bridge 705. The implant 700 is shown with the first anchor inserted into the vertebra 707 superior to the fracture 709, and the second anchor 705 inserted into the vertebra 707 inferior to the fracture 709.

In some embodiments, the bridge and second anchor can be configured such that upon tightening of the first anchor/bone screw, the second anchor exerts a compressive force across the fracture. In some embodiments, bone graft, bone cement, or bone growth promoters can be put in the fracture, or onto or around the implant itself. Although these drawings illustrate bilateral insertion of the implants, in other embodiments a single implant may be employed unilaterally.

Figure 20A:
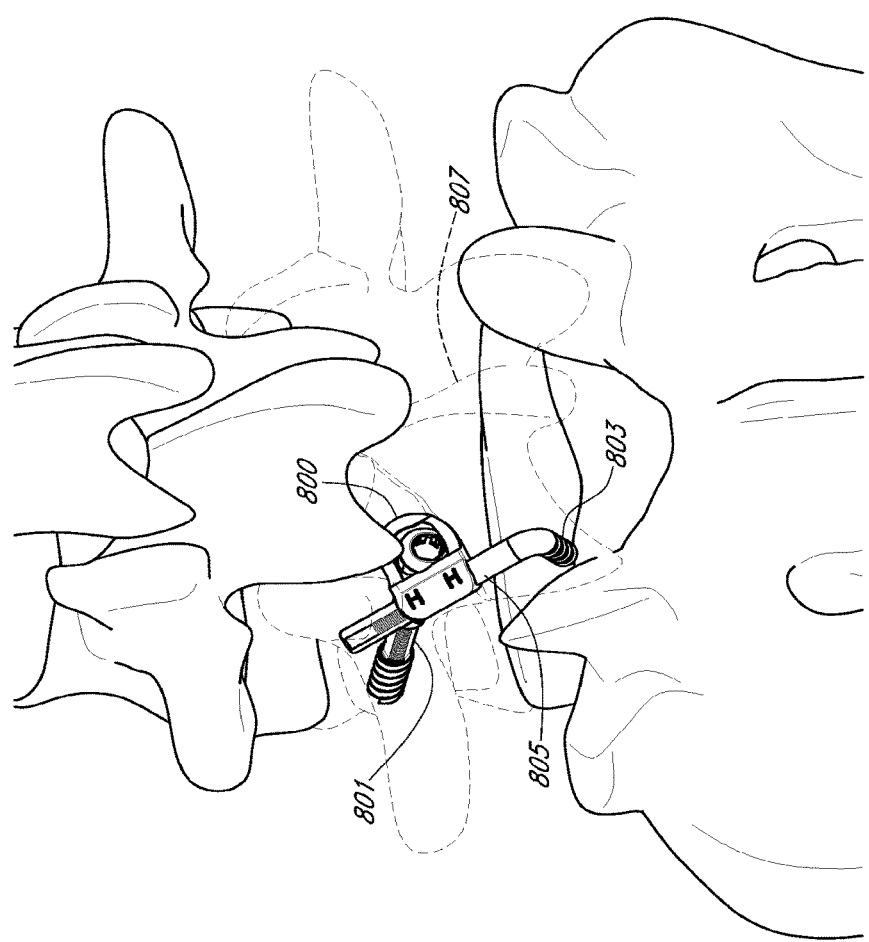
FIGS. 20A-20C illustrate various views of an implant spanning a pars fracture, the implant comprising a bone compression screw and a compressible spike.
Figure 20B:
Figure 20C:

FIGS. 20A-20C illustrate various views of an implant spanning a pars fracture, the implant comprising a bone compression screw and a compressible spike. The implant 800 includes a first anchor 801, which takes the form of a bone screw, and a second anchor 803, which takes the form of a compressible spike, with the two anchors coupled together via a bridge 805. The implant 800 is shown with the first anchor inserted into the vertebra 807 superior to the fracture 809, and the second anchor 805 inserted into the vertebra 807 inferior to the fracture 809.

In some embodiments, the bridge and second anchor can be configured such that upon tightening of the first anchor/bone screw, the second anchor exerts a compressive force across the fracture. In some embodiments, bone graft, bone cement, or bone growth promoters can be put in the fracture, or onto or around the implant itself. Although these drawings illustrate unilteral insertion of the implant, in other embodiments a pair of implants may be employed bilaterally.

Figure 21A:
FIGS. 21A-21F illustrate various views of a compressible staple spanning a pars fracture.
Figure 21B:
Figure 21C:
Figure 21D:
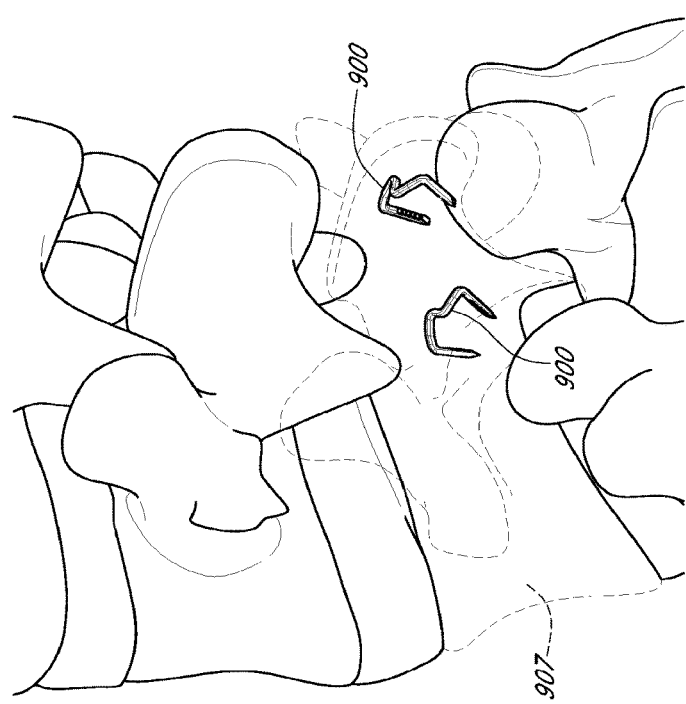
Figure 21E:
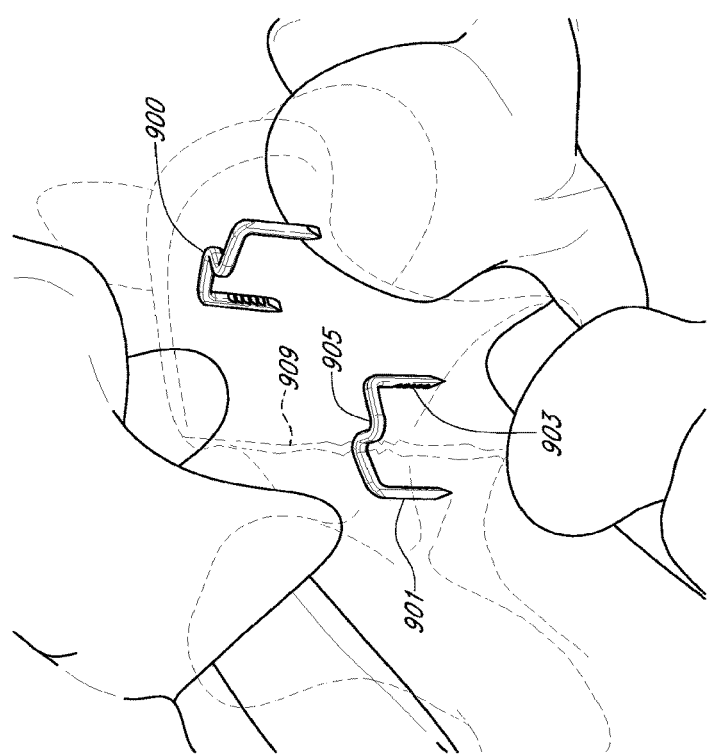
Figure 21F:
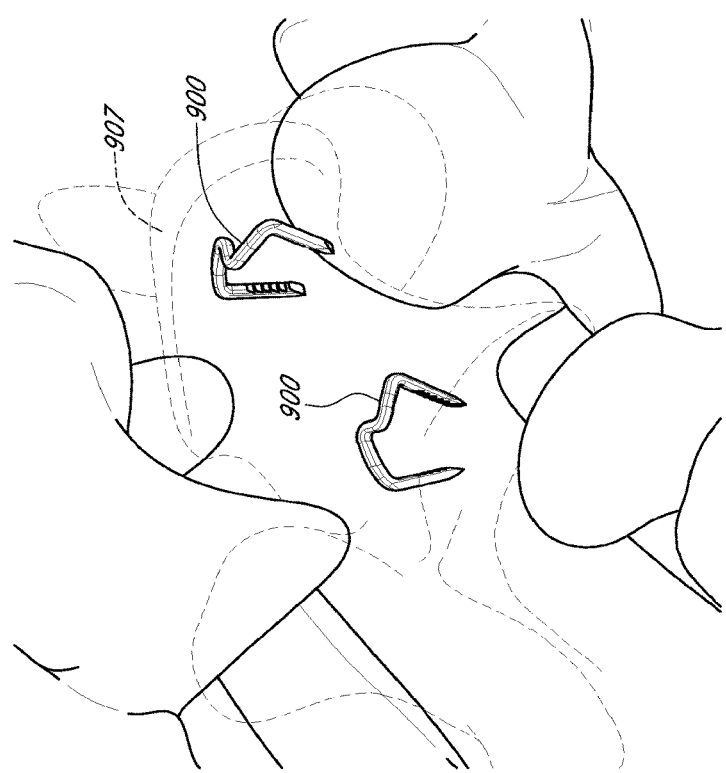

FIGS. 21A-21F illustrate various views of a staple (e.g., a compressible stable) spanning a pars fracture. Compressible staple 900 includes a first anchor 901, a second anchor 903, and a bridge 905 coupling the two together. In the illustrated embodiments the first anchor 901, second anchor 903, and bridge 905 are integrally formed as a single piece. In some embodiments, the compressible staple 900 can be made of memory metal or other memory material so as to impart a compression force after insertion into the vertebra. The implant 900 is shown with the first anchor 901 implanted into the vertebra 907 superior to the fracture 909, with the second anchor 903 implanted into the vertebra 907 inferior to the fracture 909. FIG. 21A illustrates the implant spanning the fracture, while FIG. 21B provides the view with the vertebra shown in transparent view. FIGS. 21C and 21D illustrate solid and transparent views, respectively, of the vertebra after the fracture 909 has healed. FIGS. 21E and 21F illustrate close-up views of the implant 900 spanning the fracture 909 before healing (FIG. 21E) and after healing (FIG. 21F).

As noted above, the compressible staple may be made of memory metal or other memory material such that, after insertion, the implant provides a compressive force across the fracture. For example, the implant may be cooled for insertion, and then upon heating, the shape memory material may reach its transition temperature and assume a new shape which provides compressive force. In some embodiments, bone graft, bone cement, or bone growth promoters can be put in the fracture, or onto or around the implant itself. Although these drawings illustrate bilateral insertion of the implants, in other embodiments a single implant may be employed unilaterally.

Figure 22A:
FIGS. 22A-22D illustrate various views of a compressible staple with spikes spanning a pars fracture.
Figure 22B:
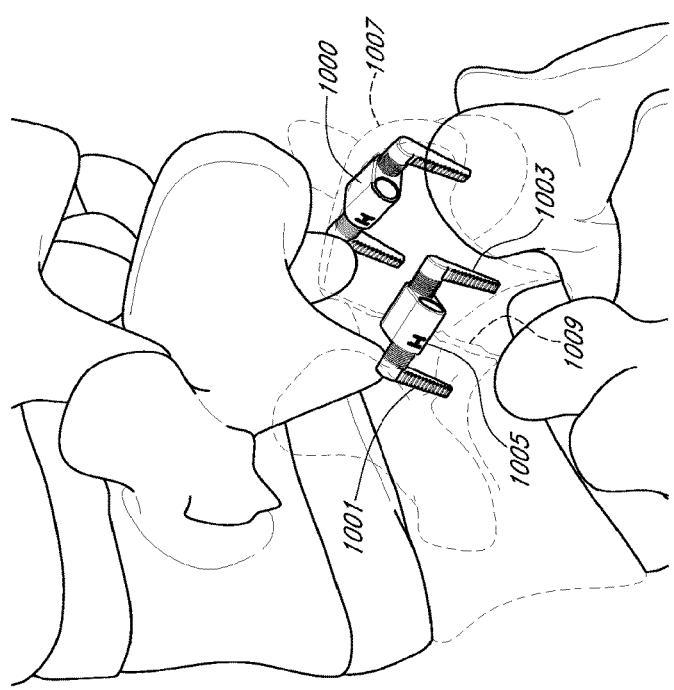
Figure 22C:
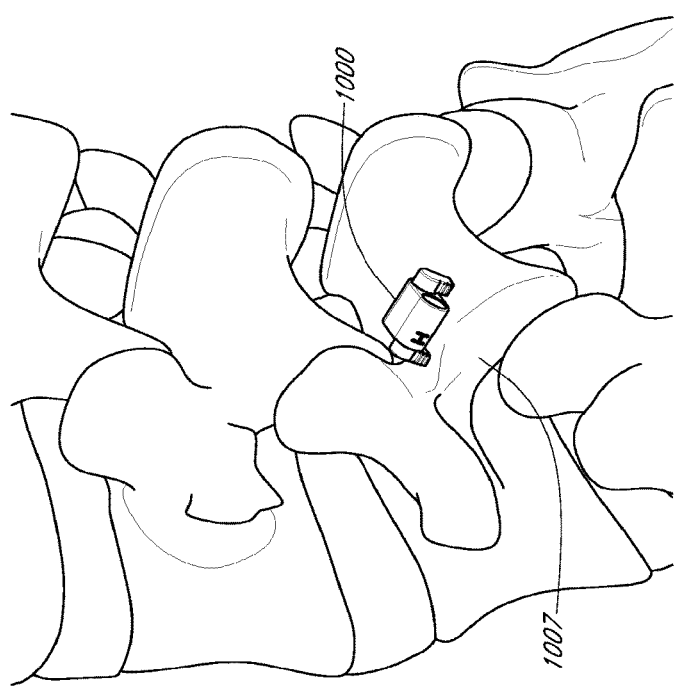
Figure 22D:
Figure 23A:
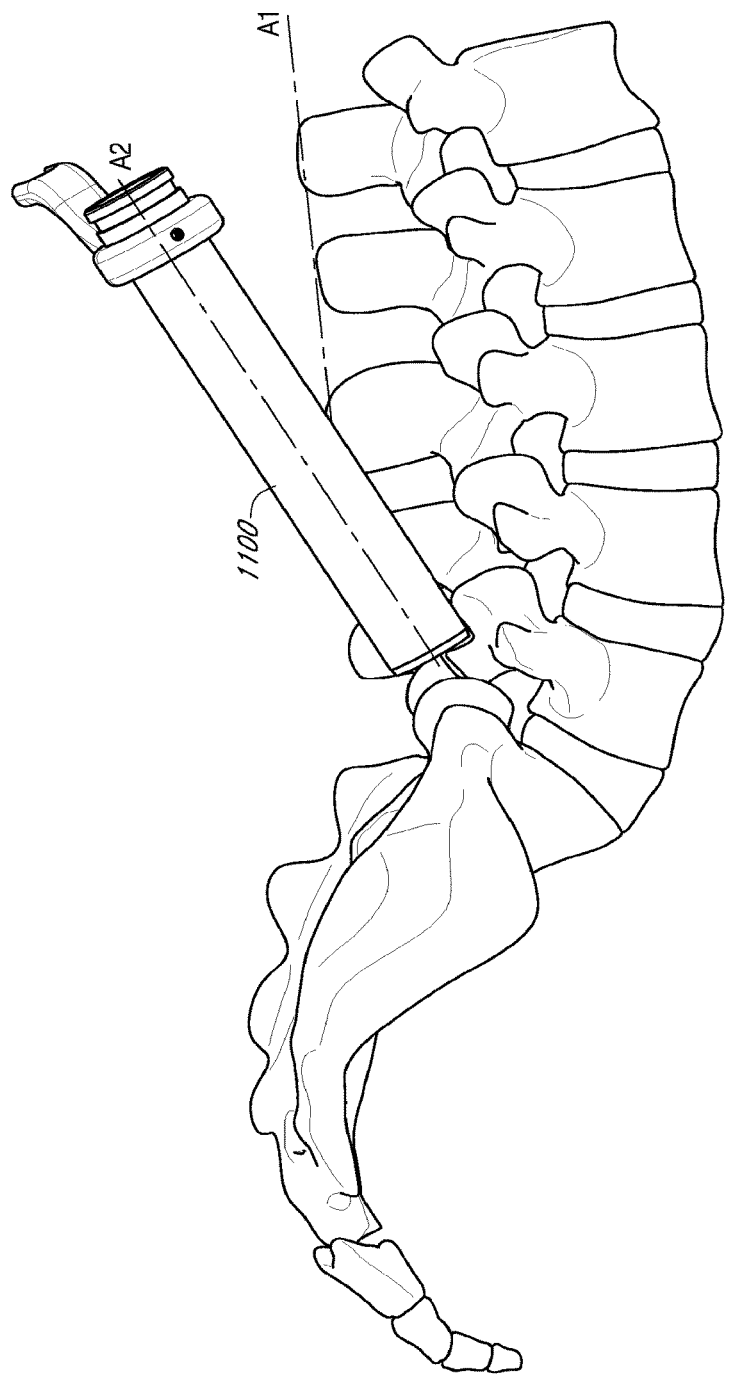
FIGS. 23A-23J illustrate various views of a cannula and method of insertion of an implant for pars defect repair.
Figure 23B:
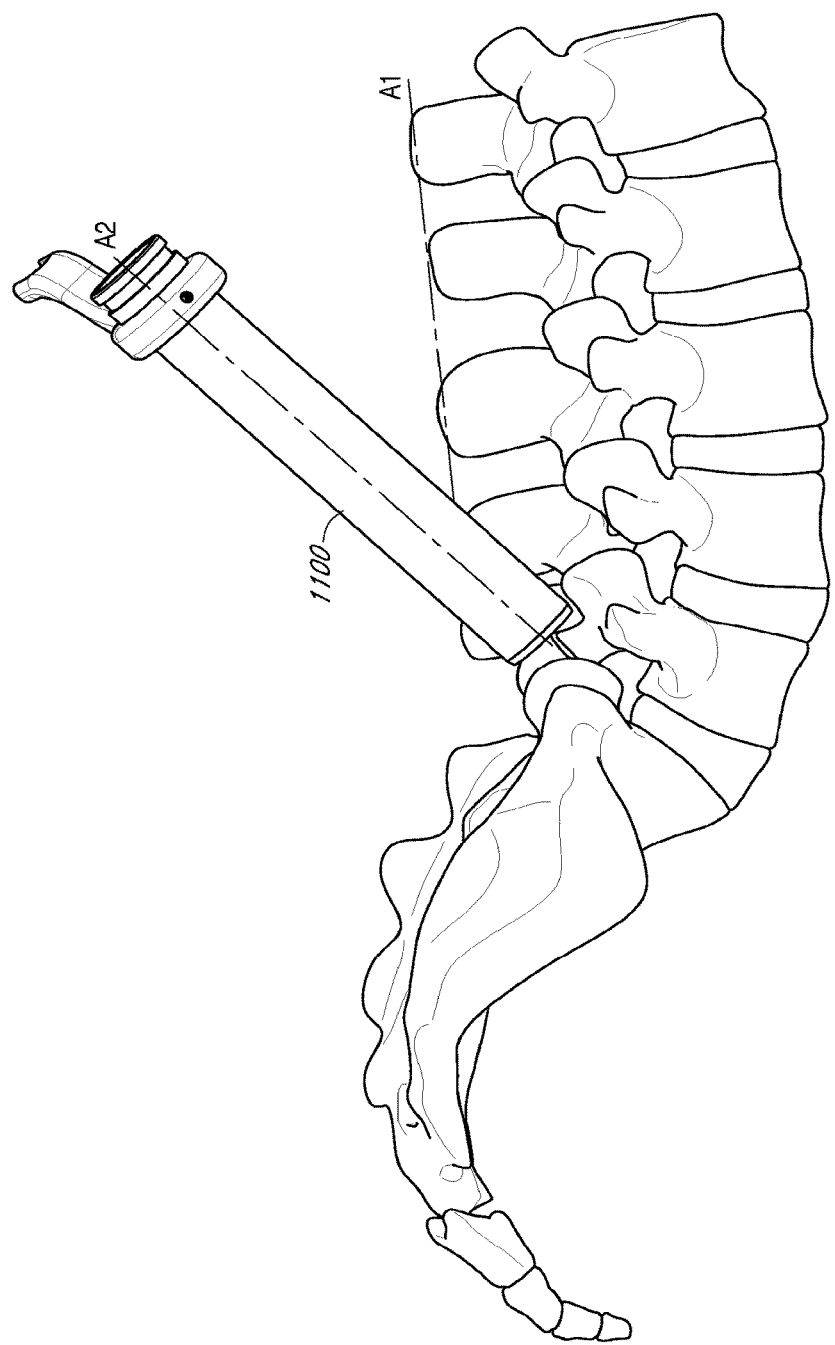
Figure 23C:
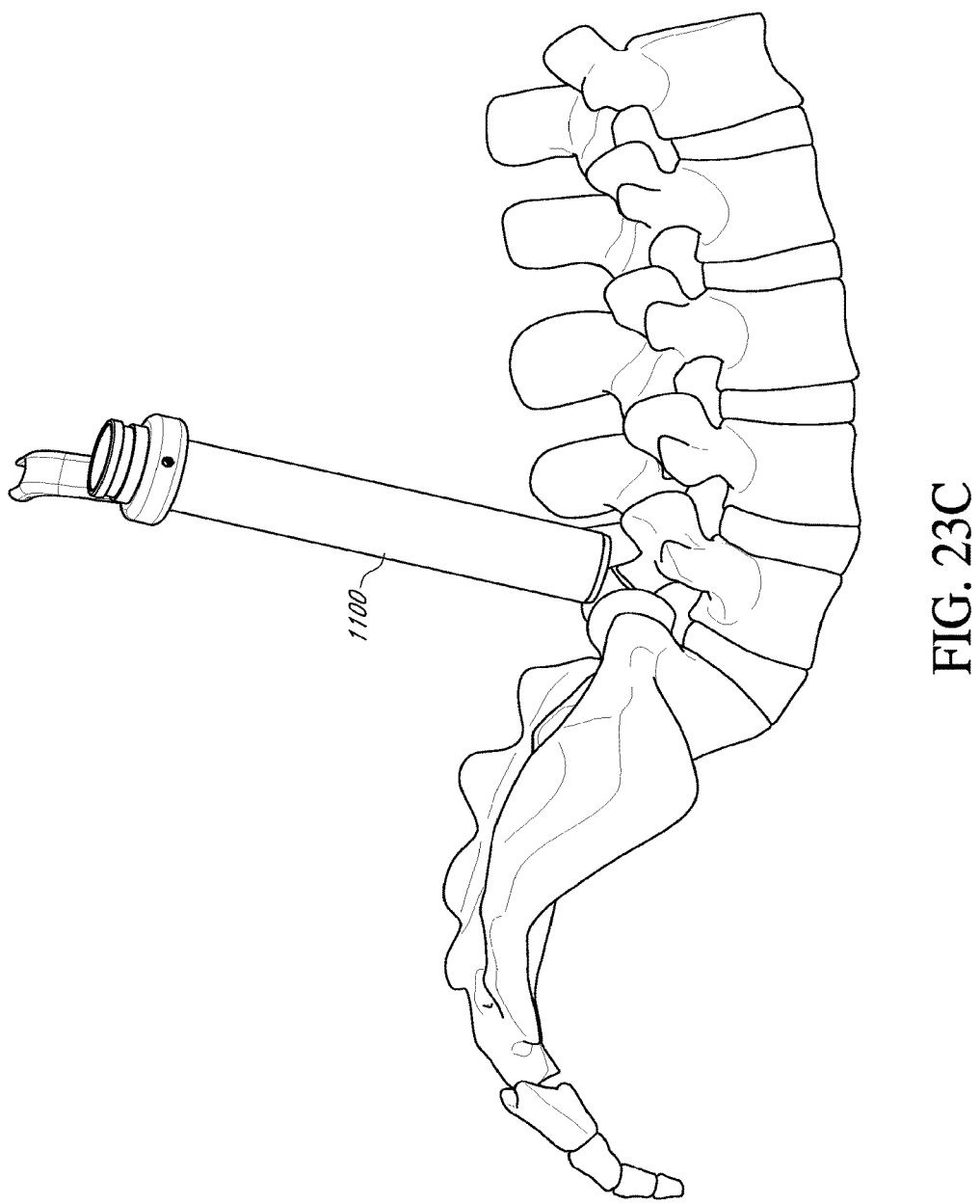
Figure 23D:
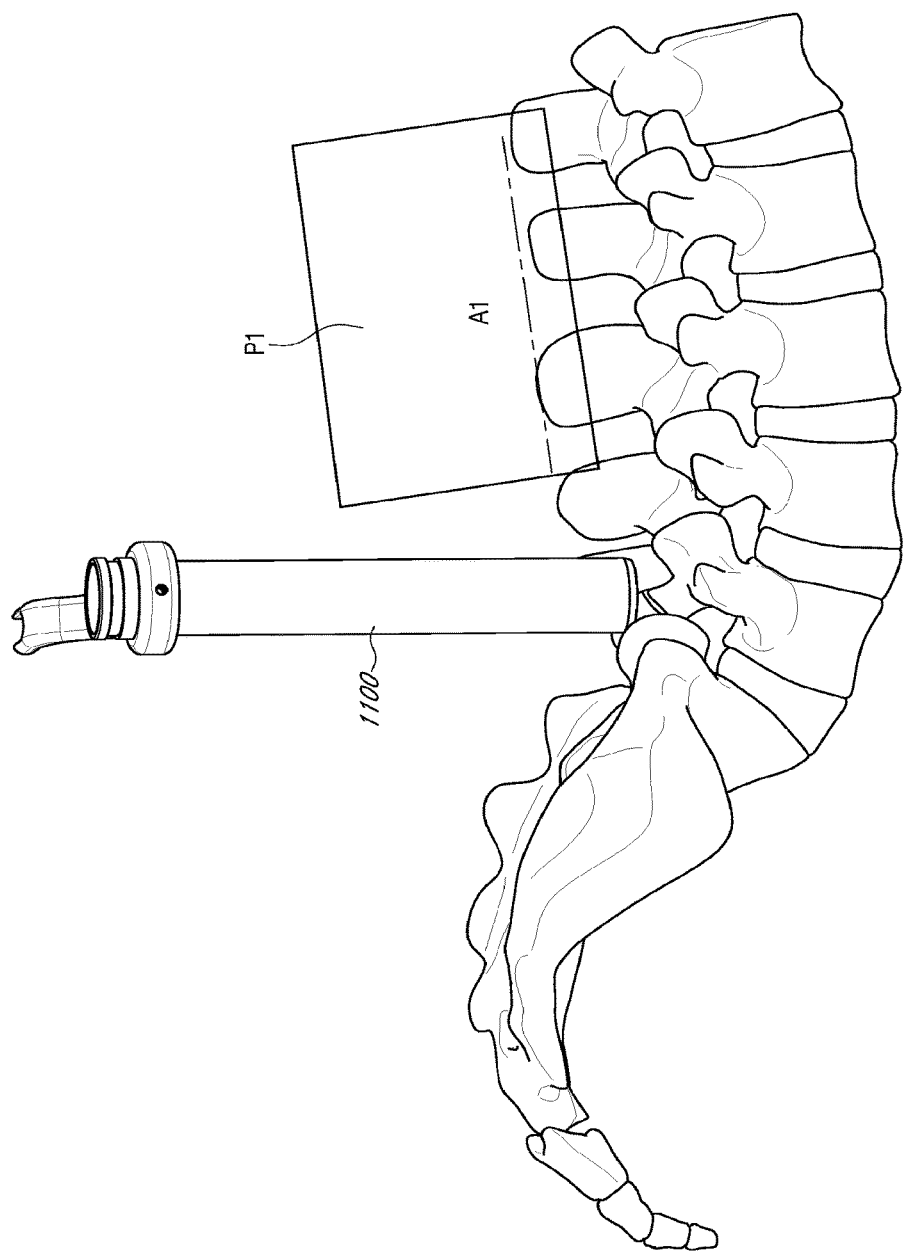
Figure 23E:
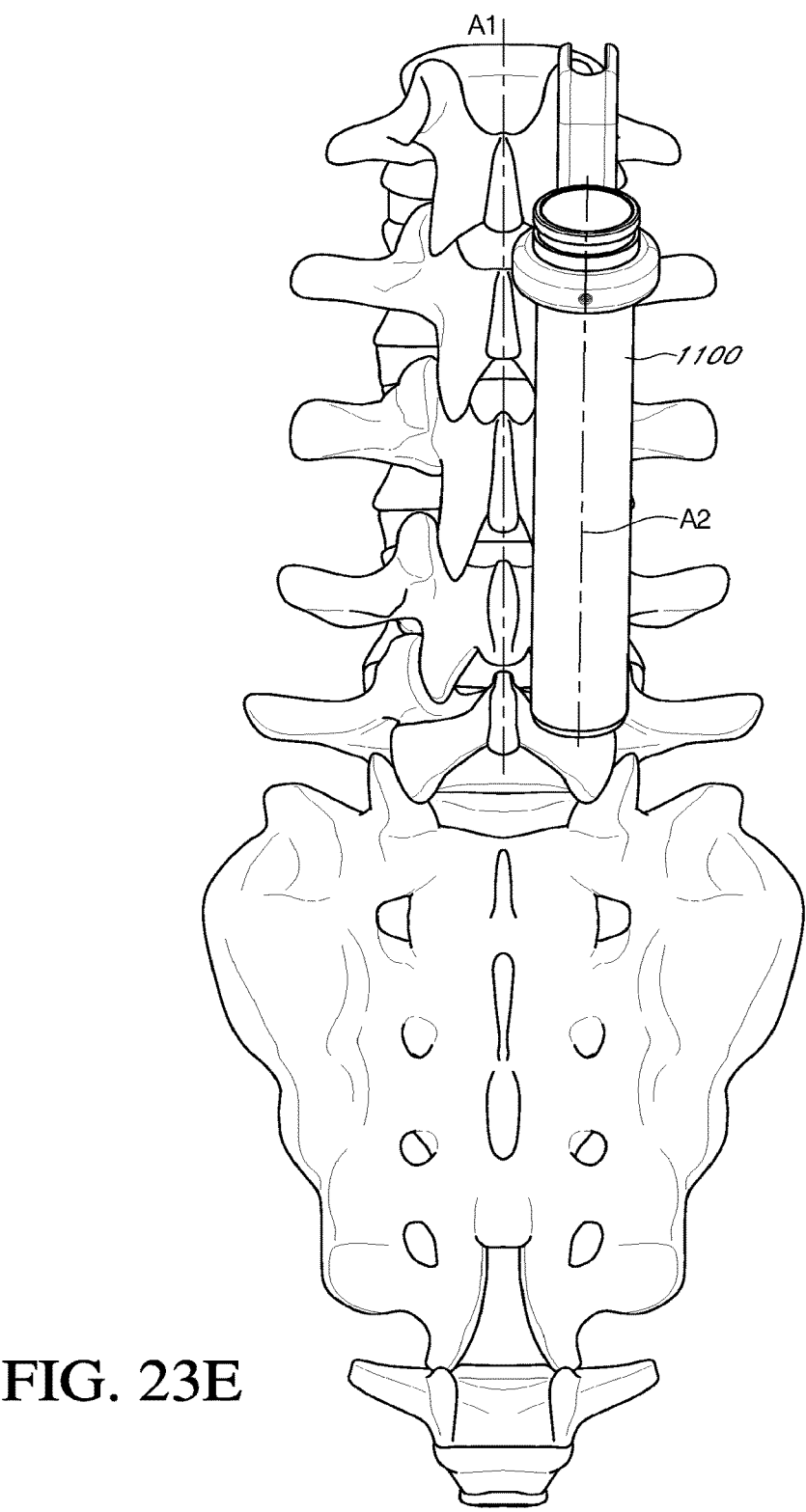
Figure 23F:
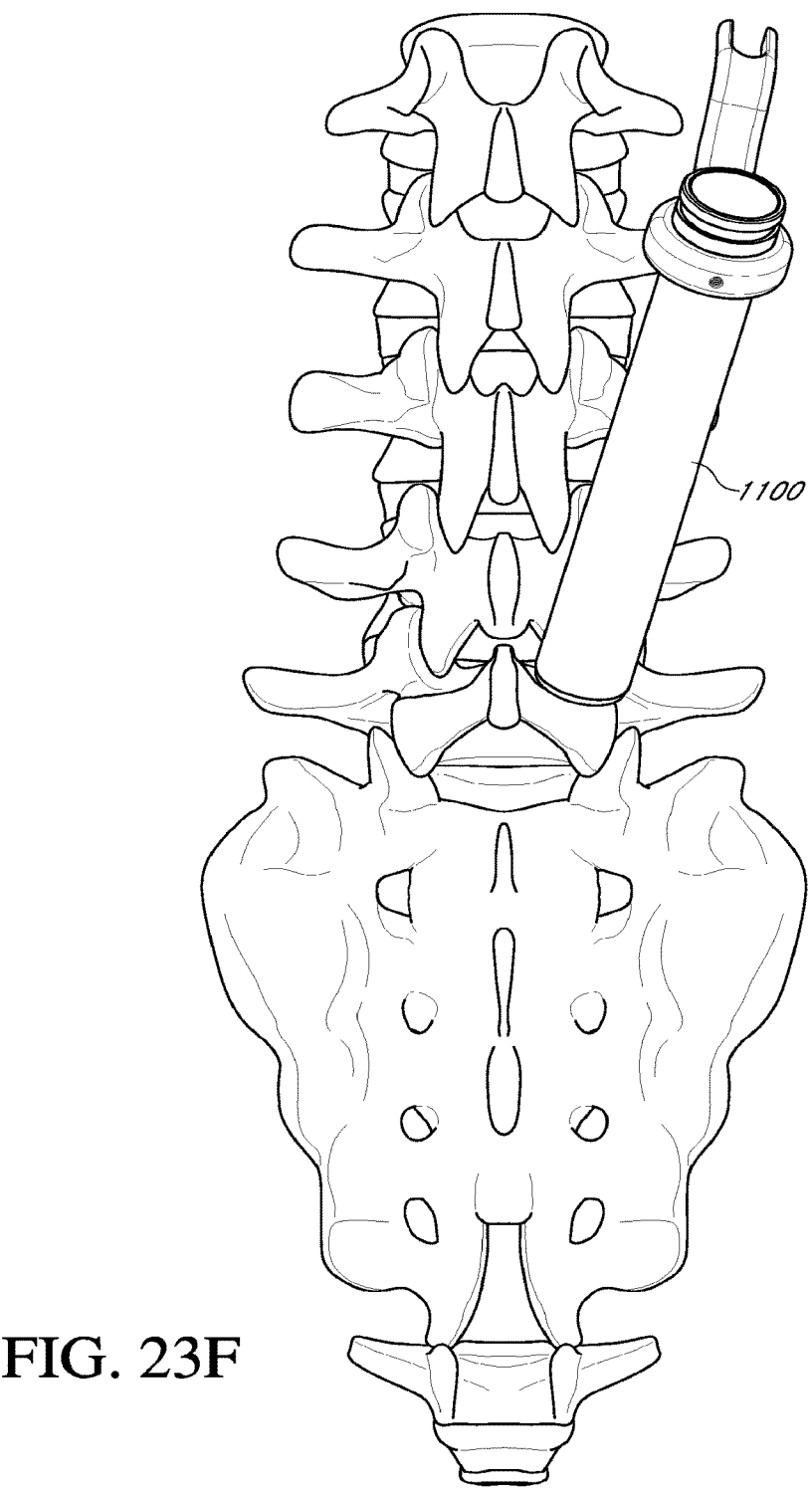
Figure 23G:
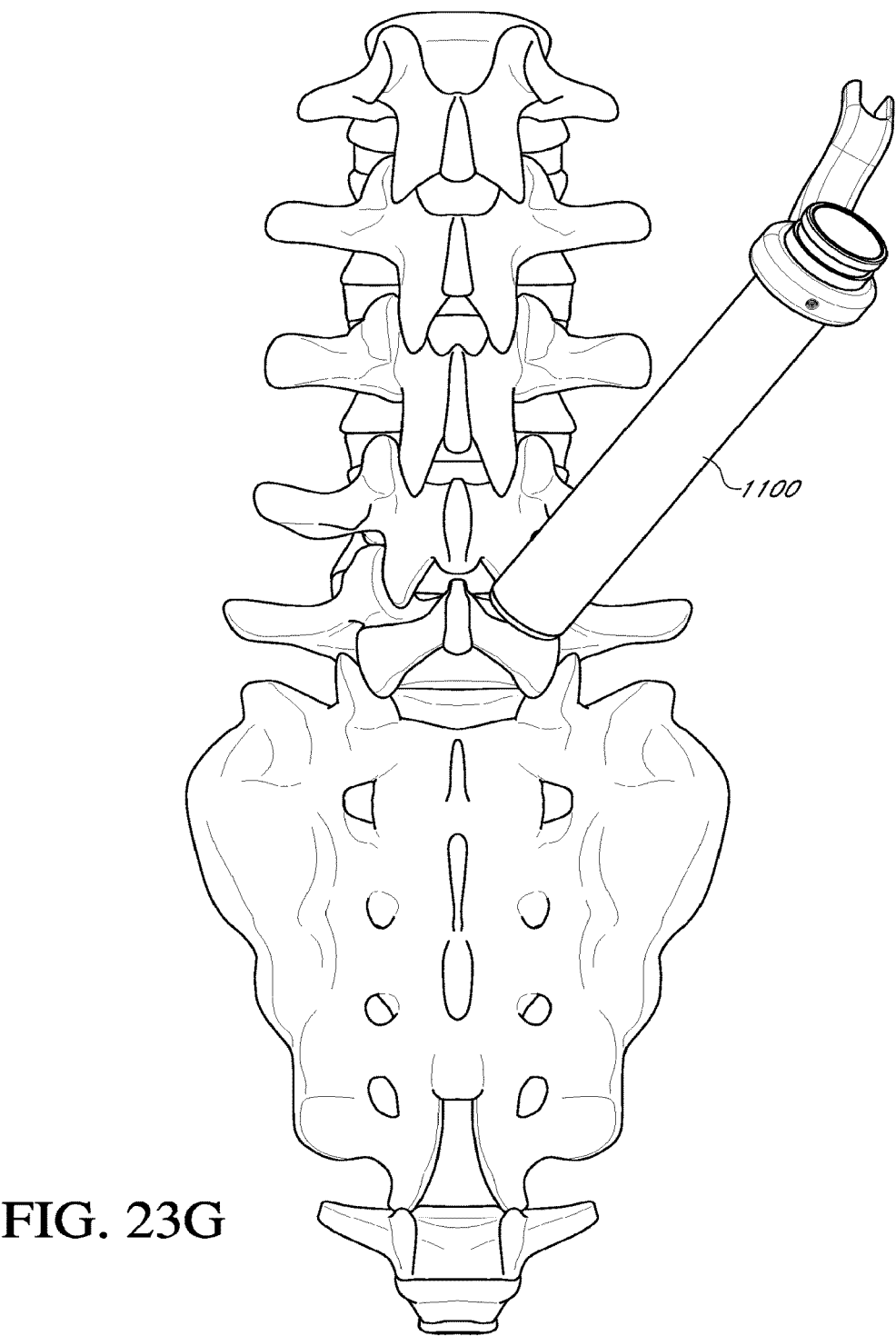
Figure 23H:
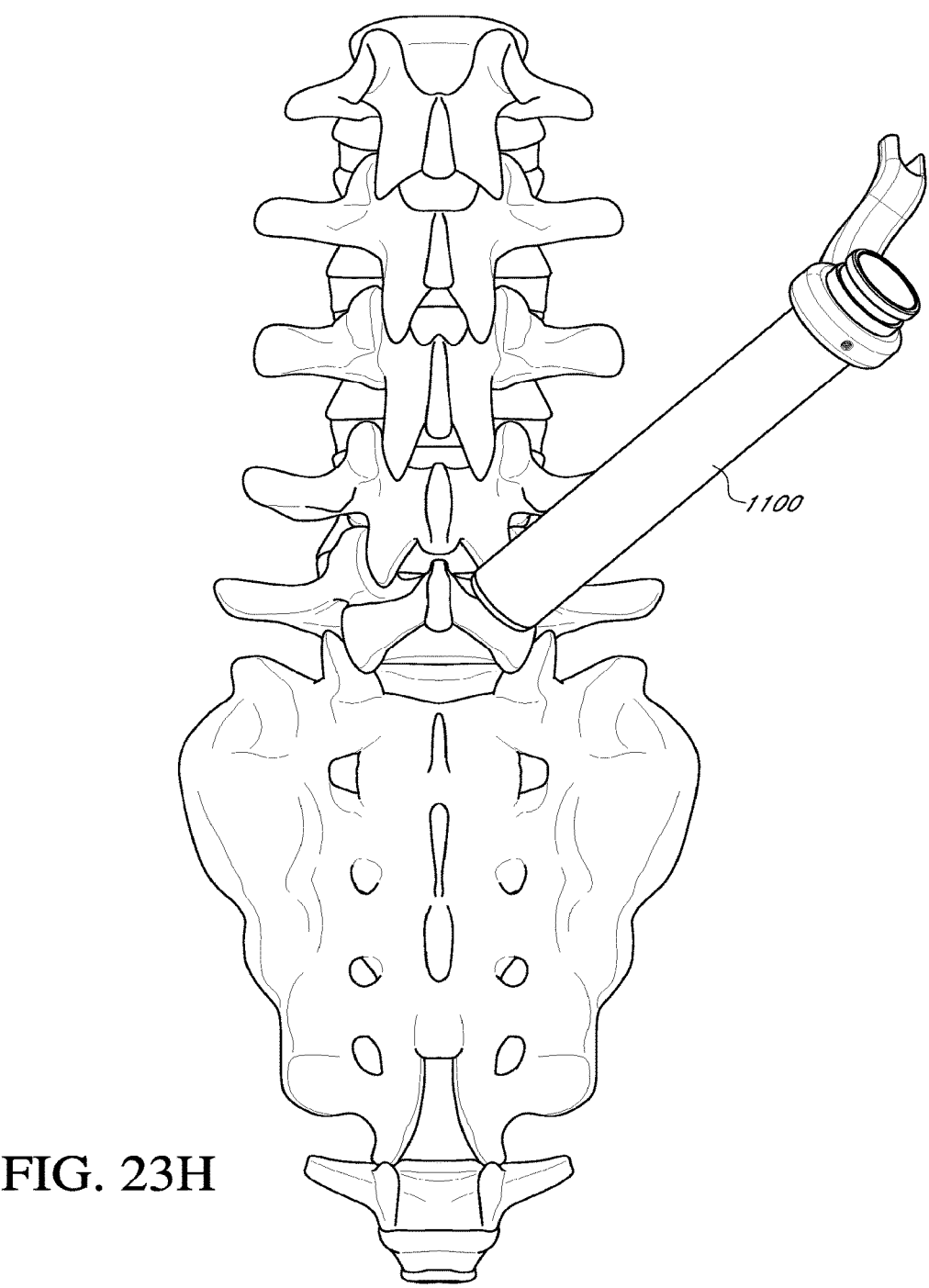
Figure 23I:
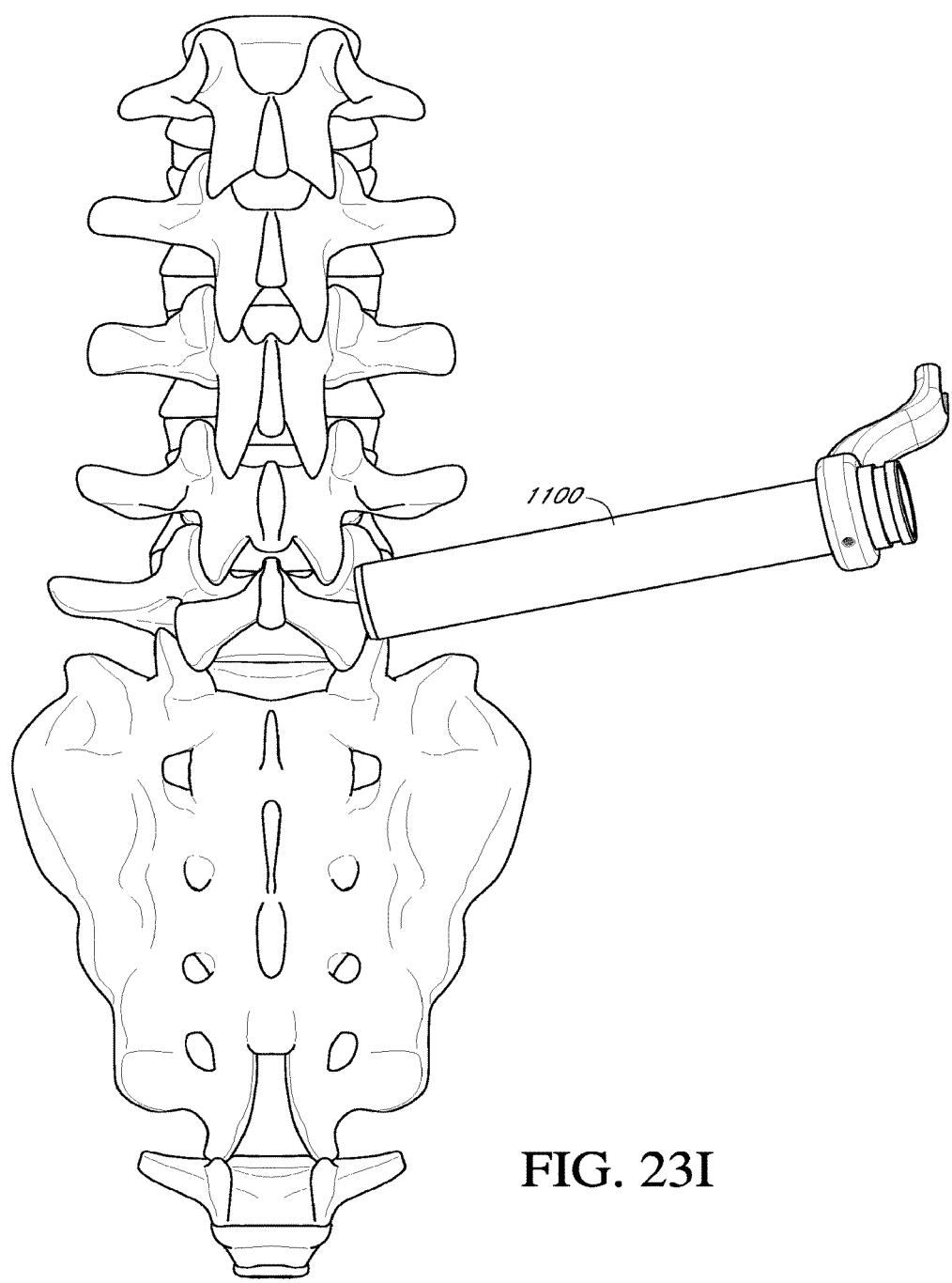
Figure 23J:
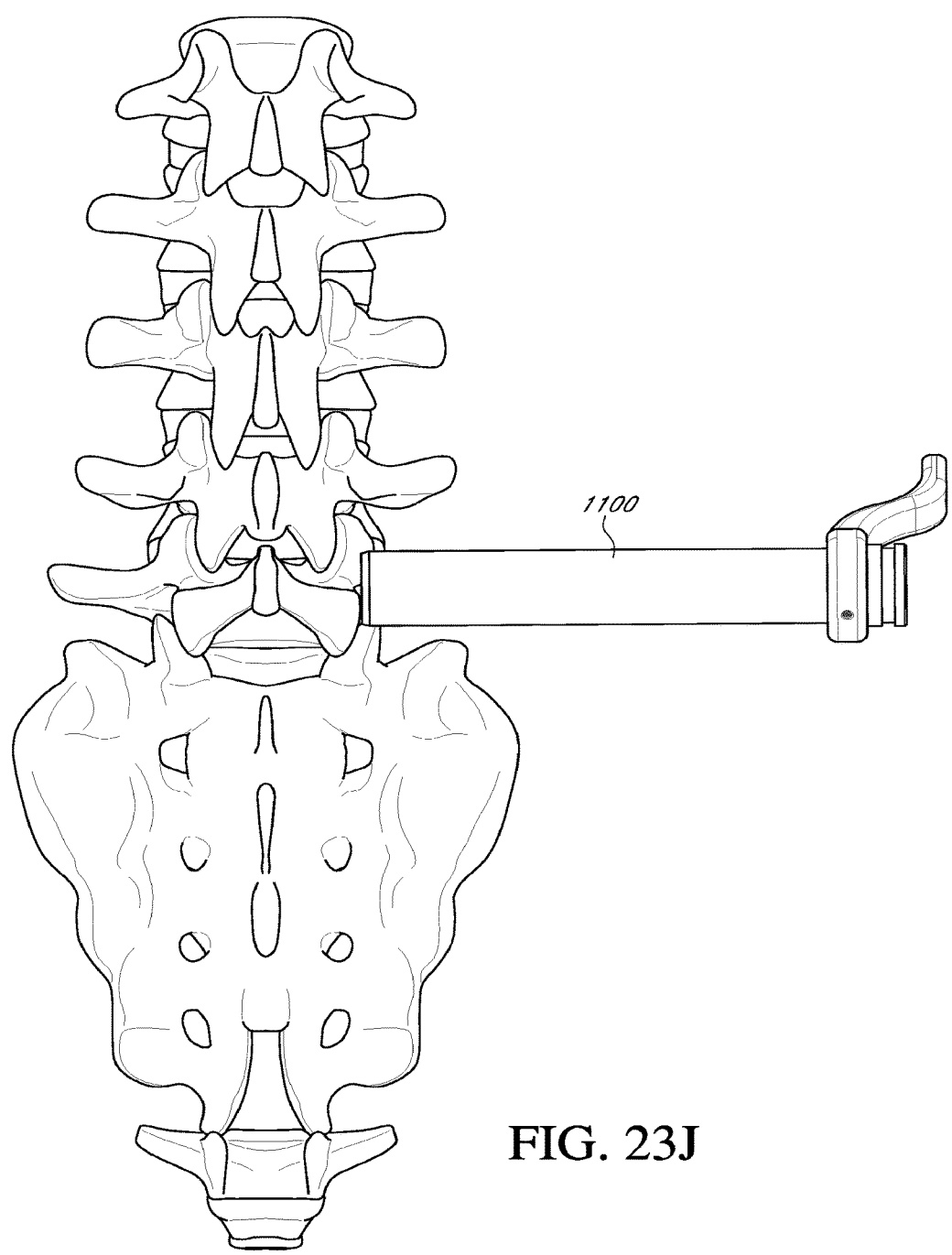
Figure 24A:
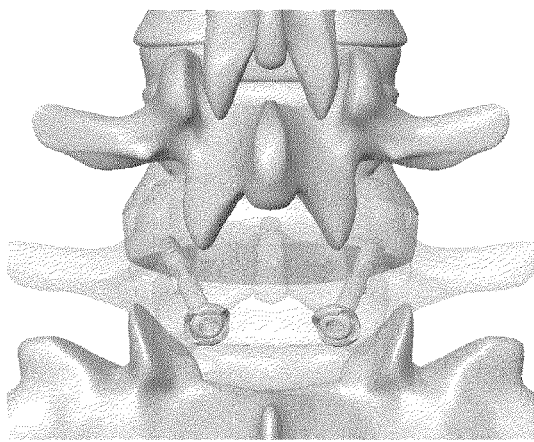
FIGS. 24A-D illustrate a compression screw positioned across a pars fracture.
Figure 24B:
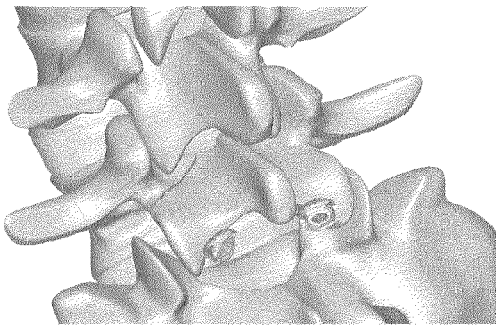
Figure 24C:
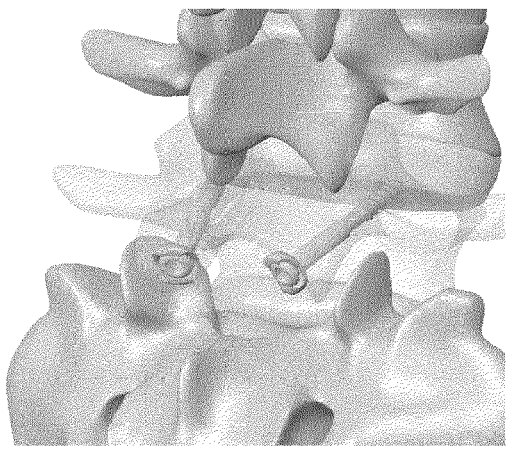
Figure 24D:
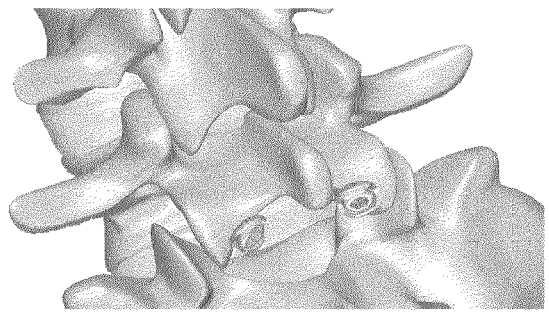

FIGS. 22A-22D illustrate various views of a compressible staple with spikes spanning a pars fracture. Compressible staple 1000 includes a first anchor 1001, a second anchor 1003, and a bridge 1005 coupling the two together. The implant 1000 is shown with the first anchor 1001 implanted into the vertebra 1007 superior to the fracture 1009, with the second anchor 1003 implanted into the vertebra 1007 inferior to the fracture 1009. FIG. 22A illustrates the implant spanning the fracture, while FIG. 22B provides the view with the vertebra shown in transparent view. FIGS. 22C and 22D illustrate two views of the implant in place after the fracture 1007 has healed.

In some embodiments, the compressible staple can be compressed across the fracture, during or after insertion of the implant, to compress the two parts of the vertebra together. In some embodiments, bone graft, bone cement, or bone growth promoters can be put in the fracture, or onto or around the implant itself. Although these drawings illustrate bilateral insertion of the implants, in other embodiments a single implant may be employed unilaterally.

In some embodiments, the implant or staple can include three anchors, four anchors, or more. Such implants can be particularly useful when dealing with complex fractures which can include multiple breaks or fracture lines across the vertebra. The various anchors can be coupled together via the bridge, and may be positioned with respect to the pars fracture so as to promote fusion across the break or breaks in the bone.

Another approach to repairing spondylolysis is direct insertion of a compression screw, for example fixation device 12 described above with respect to FIGS. 2-4, directly across the fracture. In other embodiments, a lag or Herbert screw can be used to apply compression across the fracture. As noted above, direct insertion of a traditional screw across the fracture is sometimes referred to as Buck's Technique. FIGS. 24A-D illustrate a compression screw, such as the fixation devices 12 described above with respect to FIGS. 2-15, positioned directly across the facture along an axis of insertion used in the Buck's Technique.

Such a procedure can be carried out under AP and lateral fluoroscopy. The AP view is adjusted to for the lordosis as it is preferable to view the disc margins in true AP fashion. The skin can be prepared and draped in the usual way. In one embodiment, a small midline incision can be made just large enough to allow a trocar to be inserted with ease, usually approximately 2 cm. The incison can be planned by palpation of the spinous processes and verification with a lateral image on fluoroscopy to establish the correct direction of the surgical track with a Kirshner wire held to the side of the patient. The trajectory aims to cross the lysis and can point to the top of the origin of the pedicle on lateral fluoroscopy.

Under AP and lateral fluoroscopy screening the sterile access needle can first placed on the edge of the lamina, again with the trajectory aiming to cross the lysis and pointing to the top of the origin of the pedicle on AP and lateral fluoroscopy. On AP screening an "up and out" trajectory can be seen i.e. the insertion point starts at the edge of the lamina and the projected wire trajectory runs in a superior and lateral direction towards the top of the pedicle. Once the correct entry point is confirmed, the needle can be gently tapped in place with a small hammer.

The inner stylet can then be freed by turning the handle and removed. A K-wire can the then advanced under fluoroscopy screening so as to cross the defect, to the superior half of the pedicle no further than the level of the posterior wall of the vertebra. Sometimes the wire may progress in an almost parasagittal plane. When correct placement of the K-wire is confirmed on AP and lateral fluoroscopy screening, the needle can be removed taking care not to pull out the K-wire at the same time. The lumbar fascia can then be incised in a parasagittal direction where the K-wire passes through. The incision should be long enough to accommodate the working sheath or cannula comfortably, approximately 1.5 cm.

The cannula can then be placed over the K-wire, taking care not to displace the wire, until it hits the lamina. Correct placement can be confirmed with fluoroscopy. The remainder of the procedure can be done under lateral fluoroscopy only. Using a cannulated power drill, the cannulated drill-bit can then be placed over the wire and the trajectory is drilled through the defect under fluoroscopy screening. The drill can include a positive stop in the shape of a sphere which prevents the drill advancing too far. There often is a distinct resistance when crossing the defect.

The cannulated hand driven tap is then placed over the K-wire and the screw hole is tapped. The tap can then be advanced just a little further than the tip of the drill which aids pull out strength, and then removed carefully so as to not pull out the K-wire. The screw implant can be loaded onto the driver. The driver is then put over the K-wire and the plastic clip is only removed just before insertion into the work sheath. Once engaged onto the bone the screw can be advanced through the trajectory under fluoroscopy with a continuous screwing clock-wise motion. Care is taken not to disengage i.e. pressure can be kept onto the screw and to avoid no pull-back on the driver.

A traction device can then be placed over the screw pin and pulled until no further pull can be applied; on fluoroscopy, the ring can now be seen to be flush to the bone and the central part of the screw can be seen to be a little shorter indicating compression. The pull pin remover may then be inserted over the K-wire and engaged. Four clockwise turns may be needed to disengage the pin from the screw and the pin can then be pulled out. The K-wire can then be removed and the procedure can be repeated on the opposite side in the same fashion through the same wound. A final fluoroscopy check can be carried out. The wound is closed in the usual fashion. Mostly only one or two stitches are required. Sometimes just steristrips will suffice.

Thus, for example, with the device described above, a method for repairing spondylolysis can comprise a advancing a fixation device (e.g., the fixation device 12) comprising a body having a first portion that forms a bone anchor (e.g., bone anchor 34 and/or helical flange 72) and a second portion that forms a proximal end of the fixation device, across a pars fracture using a Buck technique (e.g. such that the body spans the fracture); advancing a proximal anchor (e.g., proximal anchor 50) along the fixation device (e.g., by proximally retracting the body with respect to the proximal anchor and/or or in combination with distally pushing the body) to adjust compression across the facture. In a final position, the bone anchor can be positioned (at least partially on one side of the facture) and the proximal anchor can rest against (directly or indirectly) against bone on the other side of the fracture. In other embodiments, a lag or Herbert screw can be used to apply compression across the fracture. In some embodiment, the proximal anchor is advanced by rotation the proximal anchor over threads on the body In some embodiments, prior to insertion of the compression screw across the fracture using Buck's technique, the fracture site can be accessed through a separate incision made above the fracture—for example using a posterior or posterolateral approach. For example, a K-wire can be inserted into the fracture site using a posterior or posterolateral approach, and then a dilator or sequential dilators to provide a path for the surgeon to access the fracture site and do the necessary preparation. Alternatively, a Jamshidi needle can be used rather than K-wire and dilators. Such preparation of the fracture site can include rasping, eroding, grinding, burring etc. of the fracture site, removing scar tissue, cartilage formation, placement of bone graft material or bone cement, etc. This can be particularly advantageous for older patients who may have had fractures from prior years which may need direct preparation of the site in order to promote healing.

In various embodiments described herein, bone graft material (e.g., autograft, allograft, demineralized bone matrix), bone growth promoters (e.g., bone morphogenic proteins), and/or bone cement may be used in conjunction with the fixation devices described herein. For example, bone graft material, bone growth promoters, and/or bone cement can be introduced into the pars fracture before and/or after insertion of the fixation device(s). This may help promote fusion of the fracture, and/or to increase fixation. This can be particularly advantageous in cases in which the bone quality is poor, but the approach may be applied to any quality of bone. In some embodiments, the fixation device is cannulated. Accordingly, in such embodiments the bone graft, bone growth promoters, and/or bone cement can be introduced through the interior passageway after insertion of the fixation device. In some embodiments, the fixation device may be cannulated and may also include a plurality of exit holes. For example, a plurality of exit holes may be arranged on the outer surface of the fixation device. The exit holes may be in fluid communication with the interior passageway, such that bone graft material, bone growth promoters, and/or bone cement introduced through the interior passageway can exit through the plurality of exit holes. In some embodiments, one or more of the exit holes may be oriented in a direction transverse to the interior passageway. In some embodiments, the exit holes may be distributed along substantially the entire length of the fixation device. In other embodiments, the exit holes may be limited to one or more regions of the fixation device. For example, the exit holes may be limited to certain regions such that the bone graft material, bone growth promoters, and/or bone cement exits the fixation device in preferential areas to promote fusion. In some embodiments, the exit holes may be limited to the distal region, such that the exiting bone graft material, bone growth promoters, and/or bone cement improves fixation.

The fixation devices described above and herein may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful: 1) the blend of poly(p-dioxanone) and a lactide/glycolide copolymer, as disclosed in U.S. Pat. No. 4,646,741 which is incorporated by reference and (2) the glycolide-rich blend of two or more polymers, one polymer being a high lactide content polymer, and the other being a high glycolide content disclosed in U.S. Pat. No. 4,889,119 which is incorporated by reference. Additional bioabsorbable materials are disclosed in copending application Ser. No. 09/558,057 filed Apr. 26, 2000, the disclosure of which is incorporated in its entirety herein by reference.

The fixation devices described herein may be made from bone graft. The bone graft can be autologous (e.g., harvested from patient), allograft (e.g., cadaveric bone), or synthetic (e.g., biocompatible materials that have bone-like properties). The bone graft is expected to be absorbed by the body as the natural bone heals. The allograft can be formed into any structure designed engaging bone. The allograft can be shaped by any process known in the art.

With particular reference to FIGS. 3, 4, and 4A, the device 12, or a portion thereof, can comprise allograft. The device 12 includes the body 28 having the first portion 36 and the second portion 38. In the illustrated embodiment, the first portion 36 carries the distal anchor 34. The first portion 36, the second portion 38 or a segment thereof such as distal anchor 34 can comprise allograft. The allograft distal anchor 34 can be designed to engage cancellous and/or cortical bone. In some embodiments, the distal anchor 34 comprises an allograft, while the first portion 26 and second portion 38 comprise a different material. The device 12 includes the proximal anchor 50, which can comprise allograft. In some embodiments, the body 28 comprises an allograft, while the proximal anchor 50 comprises a different material. Other devices, or portions thereof, described herein could be made of allograft. For instance, the washer 66' of FIG. 8 could comprise allograft. The annular flange 202 and/or proximal anchor 204 of FIGS. 9-15 could comprise allograft. The devices shown in FIGS. 16A-17B, or a portion there of, can comprise allograft. For instance, the bridge 390a and/or the second anchor 392a can comprise allograft. Any portion of the devices described herein, including portions designed for direct contact with the bone such as anchors, can comprise allograft.

In other embodiments, a fixation device comprising an allograft is provided having a simpler design. The fixation device comprising an allograft can be an interference screw, similar to the interference screws common in ACL surgeries. The interference screw can include a head and a body, wherein the body is threaded. The head can be a larger diameter than the threads or approximately equal to the diameter of the threads. The head can be made of allograft, the body can be made of allograft or the entire fixation device can comprise allograft. The thread can be selected to cut through bone. The thread can be formed by any process known in the art for forming threads. The interference screw can have a pointed tip or a blunt tip. In some embodiments, the interference screw in hollow.

In other embodiments, the fixation device comprising an allograft can be a pin, which can include a head and a body. The head can be a larger diameter than the body or approximately equal to the diameter of the body. The head can be made of allograft, the body can be made of allograft or the entire fixation device can comprise allograft. The body can have a smooth surface or a roughened surface. The body can be porous or hollow. The body can have a pointed tip or a blunt tip. In some embodiments, the body has the same diameter along the length of the body, in other embodiments, the body is tapered.

In other embodiments, the fixation device comprising an allograft is a push fastener, which can include a head and a body. The head can be a larger diameter than the body or approximately equal to the diameter of the body. The head can be made of allograft, the body can be made of allograft or the entire fixation device can comprise allograft. The body can have a series of ridges projecting from a circumference of the body. In some embodiments, the ridges are formed of a flexible material. The body can have a pointed tip or a blunt tip. In some embodiments, the body is the same diameter throughout, in other embodiments, the body is tapered.

The fixation devices comprising allograft can be used in any method step or medical procedure described herein. For instance, the fixation devices comprising allograft can be used in the direct insertion of the device across the fracture (i.e., Buck's technique). The device can be threaded or non-threaded, as described herein. The fixation device can be held in place by a feature to engage at least one bone segment (e.g., threads, ridges, roughened surface). In other methods, the fixation device is held in place by other fixation methods (e.g., K-wires, fasteners, bone cement). The fixation devices comprising allograft can be used to treat a pars defect. This method could be useful for incomplete fractures (e.g., stress fractures). This method could be useful when the gap between bone fragments is small or when compression is not needed.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the embodiments described herein (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In one arrangement, the fixation devices or portions thereof described herein can be made form a bioabsorbable metallic material or metallic alloy such as magnesium, a magnesium alloy, zinc and/or a zinc alloy. Such bioabsorbable metallic materials can be particularly advantageous in the arrangements for use in spondyloysis repair. For example, bioabsorbable metallic materials are not traditionally used for spinal fusion because devices made from these materials often have less strength as compared than titanium or stainless steel. However, for fracture repair in the spine, applicants have found that this is not necessarily a disadvantage for certain applications because the strength of the device may be needed for only a limited amount of time (e.g., during the healing phase of the fracture which may be on the order of a few months).

FIGS. 23A-23J illustrate various views of a cannula and method of insertion of an implant for pars defect repair. As will be described below, in certain embodiments, the implants described above can be inserted posteriorly (above) to the facture, posterolaterally to the facture, and/or lateral to the facture. In such procedures, an inserter or cannula 1100 can be used. The cannula 1100 can include a central cannula for delivery of the implants described herein. The central cannula includes longitudinal axis A2, which in some embodiments, spans the length of the cannula 1100. In certain arrangements, an incision in the appropriate location (e.g., posteriorly (above) to the facture, posterolaterally to the facture, and/or lateral to the facture) can be created to access the fracture. A k-wire (or guide wire) can then be advanced into the fracture site to define an access path and then an access device or inserter (e.g., a dilator or sequential dilators) can then be advanced over the k-wire (or guide wire) or along the path defined by the k-wire (or guide wire) to provide an access path for the surgeon to access the fracture and do desired preparation work. In some embodiments, a wire and/or guide member may not be needed, or the surgeon could use a jamshidi type needle to target the area. Accordingly, in embodiments, an implant device such as described above with reference to FIGS. 1 and 16A-22D can be inserted along an axis path and/or within access devices that are orientated posteriorly (above) to the facture, posterolaterally to the facture, and/or lateral to the facture. Preparation of the fracture can also be conducted along and/or through the same access device used to insert the implant and/or along the same access path. For example, in an embodiment, the tools for preparing the facture can be inserted through the same cannula and/or the same access device (e.g., an earlier dilator) and/or along the same access path, incision and/or opening as the implant. Preparation of the fracture site can include rasping, eroding, grinding, burring etc. of the fracture site, removing bone tissue, scar tissue, cartilage formation, placement of bone graft material and/or bone cement.

Accordingly, an embodiment comprises a method for repairing spondylolysis creating an access path from a position posteriorly (above) to the facture, posterolaterally to the facture, and/or lateral to a pars facture to the pars fracture; preparing the pars facture through the access path; and securing the pars facture. Preparing the pars fracture through the access site can include at least one of removing bone, placing bone graft, rasping eroding, grinding or burring. Securing the pars facture can include inserting a fixation device such as an implant device described above with reference to FIGS. 1 and 16A-22D through the access path. The fixation device and the preparation of the pars fracture can occur through the same axis path, opening or device. One embodiment comprises method for repairing spondylolysis: creating an access path to the pars fracture from a position posteriorly (above) the pars fracture, posterolaterally to the pars facture, and/or lateral to a pars facture; inserting a fixation device through the access path; and securing the pars facture through the access path. In an embodiment, securing the pars facture can comprising utilizing the embodiments described herein and/or in the claims and in one arrangement comprises advancing a fixation device having a first anchor, a second anchor, and a bridge extending between the two towards a target site; positioning the first anchor of a fixation device against bone on one side of a pars fracture; positioning the second anchor of the fixation device against bone on the other side of the pars fracture; advancing the first and second anchors into bone and can comprise compressing the pars fracture with first and second bone anchors and/or shortening the distance between the first and second bone anchors.

The spinous processes generally align along an axis A1, along the length of the spine of a patient. The axis A1 can be contained within a plane P1, shown in FIG. 23D. The plane P1 extends from the spinous processes of the patient. In some embodiments, the plane P1 is the sagittal plane. During delivery of the implants described herein, longitudinal axis A2 of the cannula 1100 and/or guide device/member (e.g., ki-wire, guide wire and/or jamshidi) can be orientated at an angle with respect to the axis A1 and/or the plane P1 to create an access path. In some embodiments, the cannula 1100 and/or access path can be parallel to plane P1. In some embodiments, the cannula 1100 or access path can rotated to form an angle between axis A1 and longitudinal axis A2 for insertion of the implant and/or tools used to prepare the pars fracture. FIGS. 23A-23D show exemplary angles of the longitudinal axis A2 of the cannula 1100 and/or access path with respect to axis A1 during insertion of an implant and/or tool used to prepare the pars fracture. The range of angles can include 0 degrees, 0-10 degrees, 0-20 degrees, 0-30 degrees, 0-40 degrees, 0-50 degrees, 0-60 degrees, 0-70 degrees, 0-80 degrees, 0-90 degrees, between 30 and 60 degrees, between 50 and 70 degrees. In some embodiments, the longitudinal axis A2 of the cannula 1100 is not parallel to plane P1. The cannula 1100 is rotated to form an angle between plane P1 and longitudinal axis A2. FIGS. 23E-23J show exemplary angles of the longitudinal axis A2 of the cannula 1100 with respect to plane P1. The range of angles can include 0 degrees, 0-10 degrees, 0-20 degrees, 0-30 degrees, 0-40 degrees, 0-50 degrees, 0-60 degrees, 0-70 degrees, 0-80 degrees, 0-90 degrees, 0-100 degrees, between 30 and 60 degrees, between 50 and 70 degrees, between 60 and 90 degrees. In some embodiments, the cannula 1100 and/or access path and/or guide member/device is rotated to form a non-zero angle with the axis A1 and/or the plane P1. With the cannula 1100 positioned and/or access path along the angles shown and described instruments can be inserted through the cannula 1100 to prepare the facture site and/or an implant can be inserted through the cannula 1100 and/or along the access path to secure the facture site.

Accordingly, an embodiment comprises a method for repairing spondylolysis creating an access path along the angles shown or described above and/or orientating an access device along the angles shown and described above and described above; preparing the pars facture through the access path and/or access device; and securing the pars facture. Preparing the pars fracture through the access path or access device can include at least one of removing bone, placing bone graft, rasping eroding, grinding or burring. Securing the pars facture can include inserting a fixation device through the access path and/or an access device inserted along the access path. In certain arrangements the pars fracture is secured using a device such as the devices described above with reference reference to FIGS. 1 and 16A-22D. The insertion of the fixation device and the preparation of the pars fracture can occur through the same axis path, opening or device. One embodiment comprises a method for repairing spondylolysis: creating an access path to the pars fracture along the angles described above; and securing the pars facture through the access path. In an embodiment, securing the pars facture can comprise using the embodiments described above and/or in the claims and in one arrangement advancing a fixation device having a first anchor, a second anchor, and a bridge extending between the two towards a target site along; positioning the first anchor of a fixation device against bone on one side of a pars fracture; positioning the second anchor of the fixation device against bone on the other side of the pars fracture; advancing the first and second anchors into bone and can comprise compressing the pars fracture with first and second bone anchors and/or shortening the distance between the first and second bone anchors.

In other methods, the surgeon can utilize a midline incision for treatment of a unilateral or bilateral pars defect repair. As described herein, in certain embodiments, the implants described above can be inserted posteriorly (above) to the facture, posterolaterally to the facture, and/or lateral to the facture. In certain arrangements the pars fracture is secured using a device such as the devices described above with reference to FIGS. 1 and 16A-22D. In such procedures, a cannula 1100 can be used as described herein. In certain arrangements, an incision in the appropriate location (e.g., approximately the midlines) can be created to access one or both fractures. A k-wire (or guide wire) can then be advanced into the fracture site to define an access path and then an access device or inserter (e.g., a dilator or sequential dilators) can then be advanced over the k-wire (or guide wire) or along the path defined by the k-wire (or guide wire) to provide an access path for the surgeon to access the fracture and do desired preparation work. In some embodiments, a wire and/or guide member may not be needed, or the surgeon could use a jamshidi type needle to target the area. The mid-line incision can be used to treat a unilateral pars fractures or both sides of a pars fracture if the fracture is bilateral. For a bilateral fracture, the skin incision could be the same, and the surgeon could redirect the cannula in the desired direction to reach both sides. In this method, the surgeon would be making one midline incision instead of two separate incisions for each fracture.

Accordingly, an embodiment comprises a method for repairing spondylolysis comprising a bilateral pars facture creating an midline incision, creating an access path from a midline incision; preparing and/or securing first pars facture through a first access path; preparing and/or asecuring a second bilateral pars facture through a second access path from the same midline incision and securing the second bilateral pars facture. Preparing the pars fracture through the access site can include at least one of removing bone, placing bone graft, rasping eroding, grinding or burring. Securing the pars facture can include inserting a fixation device as described above through the access path. The fixation device and the preparation of the pars fracture can occur through the same axis path, opening or device.

The spinous processes generally align along an axis A1, along the length of the spine of a patient. The axis A1 can be contained within a plane P1, shown in FIG. 23D. The plane P1 extends from the spinous processes of the patient. The midline incision can be along axis A1. The midline incision can be contained within the plane P1. During delivery of the implants described herein, longitudinal axis A2 of the cannula 1100 and/or guide device/member (e.g., ki-wire, guide wire and/or jamshidi) can be orientated at an angle with respect to the axis A1 and/or the plane P1 to create an access path, as described herein.

Figure 25B:
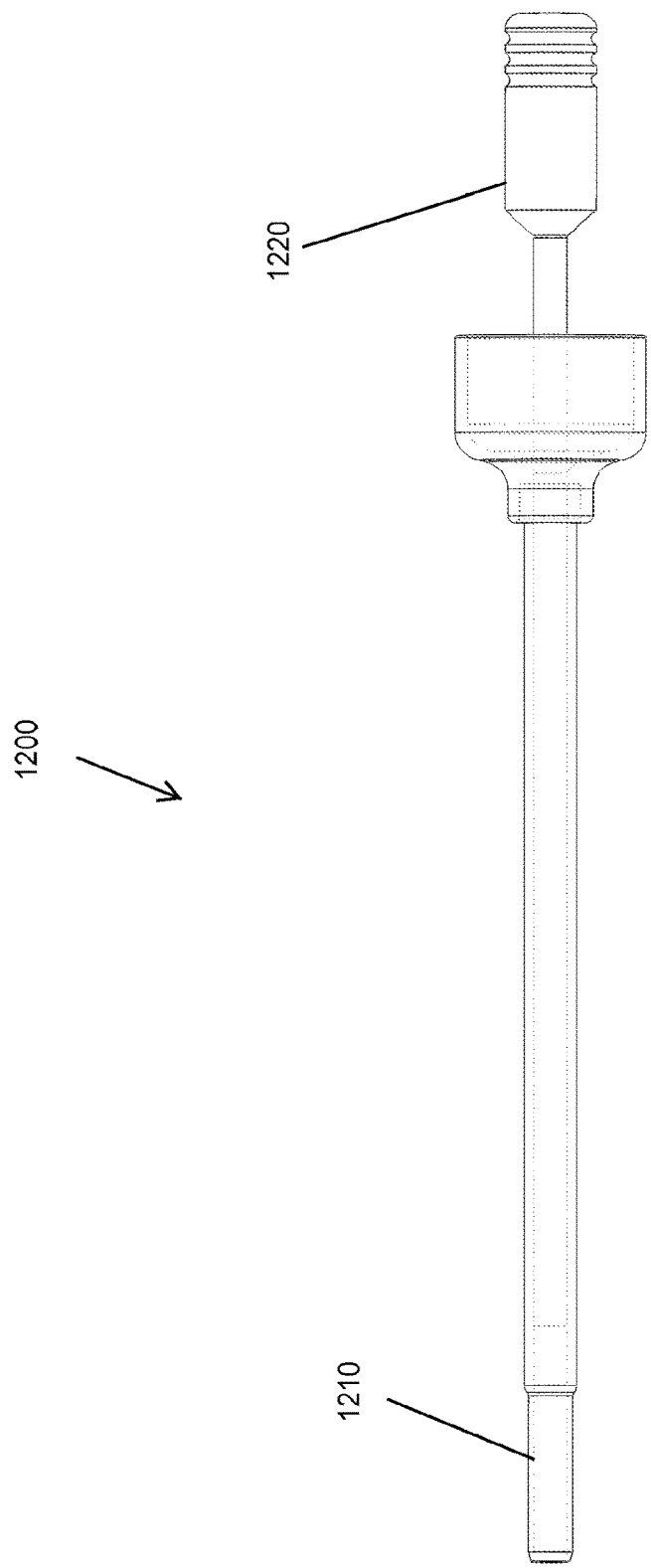
Figure 25C:
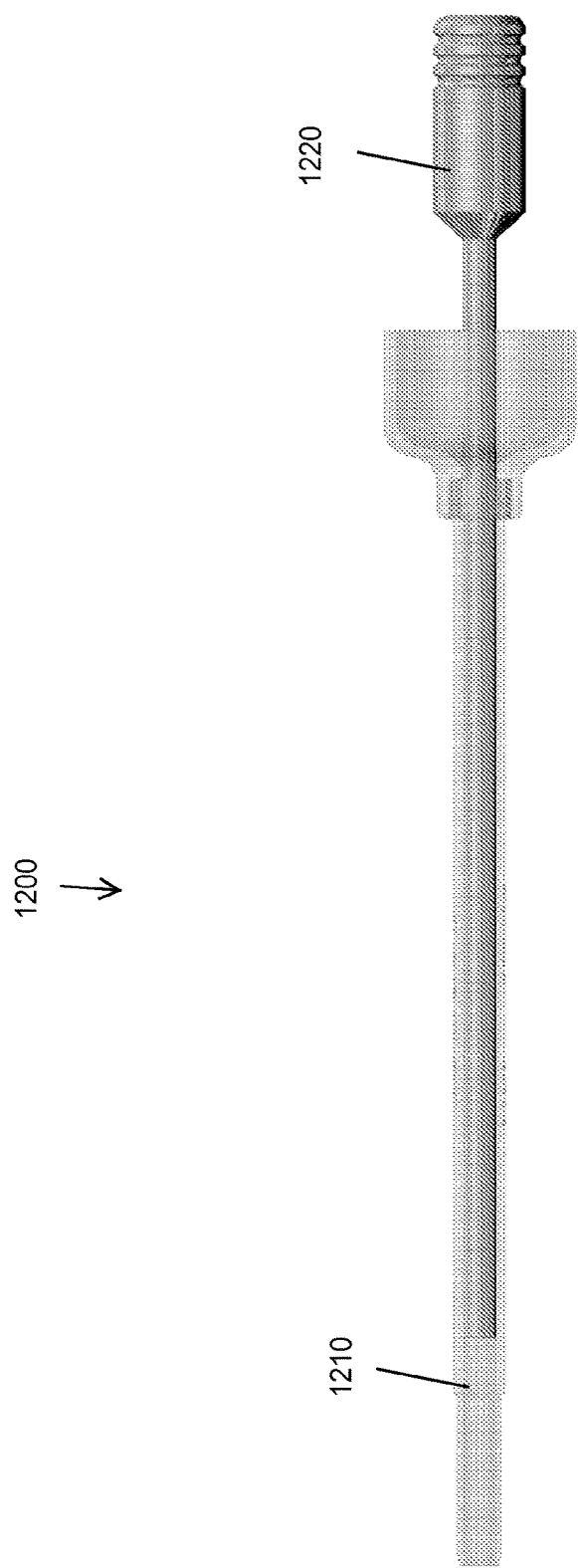
Figure 25F:
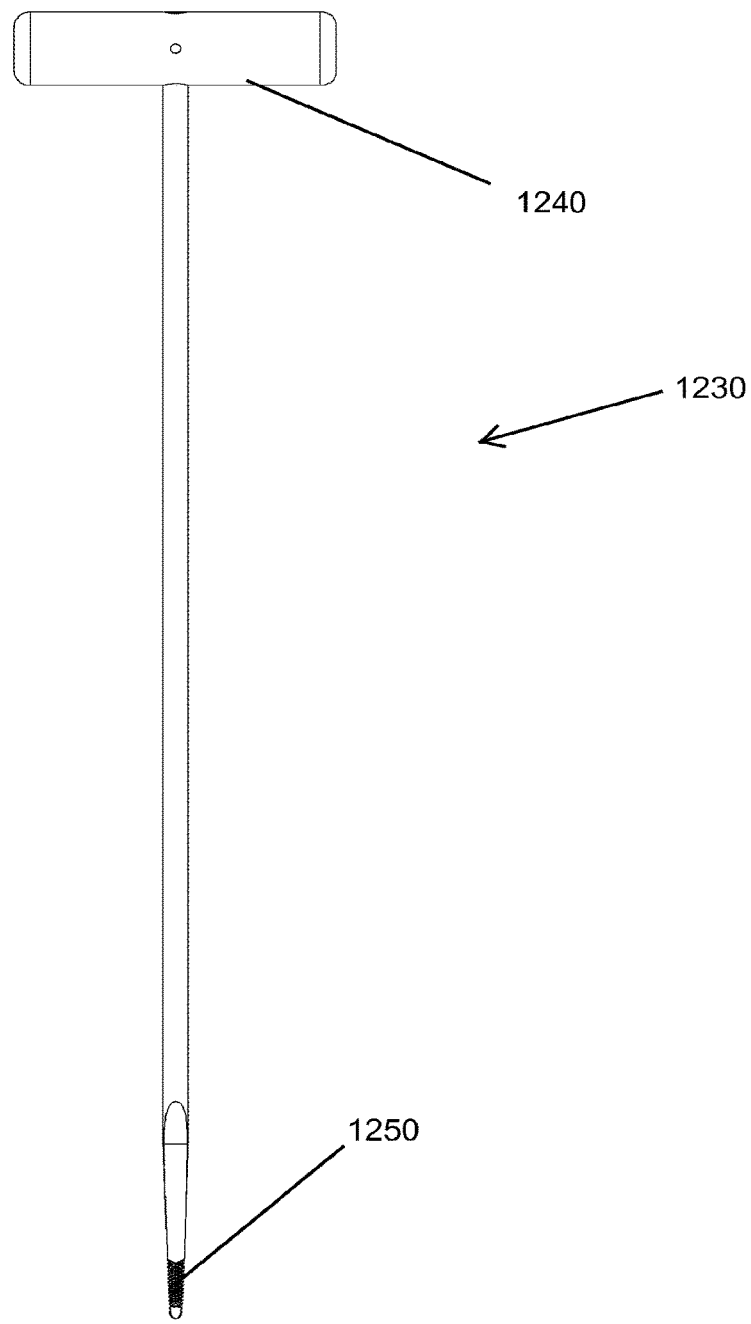
FIGS. 25F-G illustrate an embodiment of a tool delivered through the cannula of FIGS. 23A-23J.
Figure 25G:
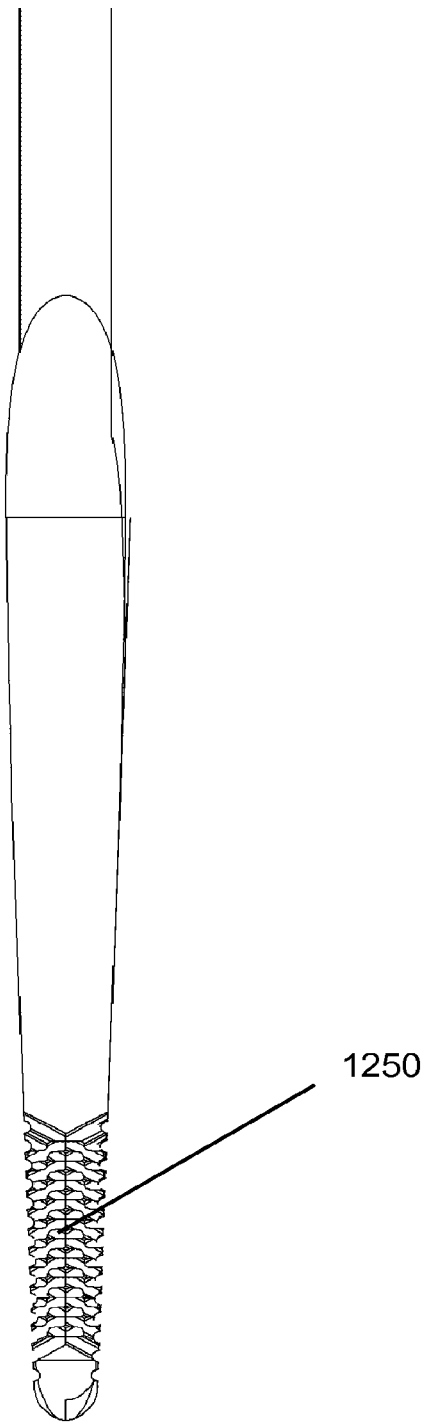

FIGS. 25A-G illustrate an embodiments of tools that can be delivered through the cannula 1100 of FIG. 23A-23J. FIGS. 25A-25E illustrate a bone graft inserter 1200. The bone graft inserter 1200 can include a cannula 1210 having a central lumen for bone graft material. The bone graft inserter 1200 can include a plunger 1220. The plunger 1220 can expel the bone graft material from the cannula 1210. FIGS. 25D and 25E show the bone graft inserter 1200 inserted within the central cannula of the cannula 1100. The cannula 1210 can be disposed within the cannula 1100 as shown. From this position, the plunger 1220 can be moved toward the spine of the patient thereby expelling bone graft material from both the cannula 1210 and the cannula 1100. FIGS. 25F-25G illustrate a rasp 1230. The rasp can include a handle 1240 and a distal tip 1250. The distal tip 1250 can include a surface for shaping and/or roughening bone. The surface can be sharpened. The surface can include serrations. FIG. 25G shows the rasp 1230 inserted within the central cannula of the cannula 1100. From this position, the distal tip 1250 can be moved toward the spine of the patient. The rasp 1230 can be used to change the surface of the bone while within the cannula 1100 as shown.

The terms "approximately", "about", and "substantially" as used herein represent an amount or characteristic close to the stated amount or characteristic that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount or characteristic. The term "up to about" as used herein has its ordinary meaning as known to those skilled in the art and may include 0 wt. %, minimum or trace wt. %, the given wt. %, and all wt. % in between.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

In the embodiments described above, it should be appreciated that the distal anchor may be configured to be used with a pre-drilled hole and/or self tapping.

The components of the above described embodiments may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present embodiments can be readily varied depending upon the intended application, as will be apparent to those of skill in the art in view of the disclosure herein. Moreover, although the present disclosure has been described in terms of certain preferred embodiments, other embodiments of the disclosure including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present disclosure is intended to be described solely by reference to the appended claims, and not limited to the preferred embodiments disclosed herein.

We claim:

1. A method for repairing spondylolysis comprising the steps of:

advancing a fixation device having a first anchor, a second anchor, and a bridge that extends between the first and second anchors towards a target site, wherein the first anchor includes a first portion and a second portion detachably coupled to the first portion;

positioning the first anchor of the fixation device against a bone on one side of a pars fracture;

positioning the second anchor of the fixation device against the bone on the other side of the pars fracture;

applying a rotational force to a rotatable coupling of the second portion of the first anchor, thereby advancing a distal anchor of the first portion of the first anchor into the bone;

axially shortening the first anchor by reducing a distance between the distal anchor and a proximal anchor of the first anchor, such that a locking element on the proximal anchor engages at least one retention structure on a body of the first anchor that prevents movement of the proximal anchor away from the distal anchor; and detaching and removing the second portion from the first portion after the axially shortening step.

2. The method of claim 1, wherein the first anchor comprises a compression screw.

3. The method of claim 2, wherein the body includes the distal anchor, the proximal anchor, and an inner member disposed within the body.

4. The method of claim 2, comprising the step of slidably moving the second anchor with respect to the first anchor.

5. The method of claim 1, further comprising the step of pulling the first and second anchors toward one another after being advanced into bone.

6. The method of claim 1, wherein the advancing step comprises advancing the first and second anchors into bone substantially simultaneously.

7. The method of claim 1, further comprising disposing bone graft material, bone growth promoters, and/or bone cement into the pars fracture.

8. The method of claim 1, wherein the advancing step further comprises the step of seating a flange against an outer surface of the bone so as to compress a fracture between the proximal and distal anchors.

9. The method of claim 8, wherein the flange is coupled to or integral with the bridge.

10. The method of claim 8, wherein the first anchor includes the flange.

11. A method for repairing spondylolysis comprising the steps of:

creating an access path from a position above, posterolaterally or lateral to a pars fracture;

inserting a fixation device through the access path, the fixation device including a first anchor, a second anchor, and a bridge that extends between the first and second anchors, wherein the fixation device further includes a flange;

advancing a distal anchor of the first anchor into bone, and axially shortening the first anchor by reducing a distance between the distal anchor and a proximal anchor of the first anchor, such that the flange seats against an outer surface of the bone so as to compress-against the bone; and securing the pars fracture.

12. The method of claim 11, wherein the step of creating an access path from a position above a pars fracture to the pars fracture comprises placing a guide member from a position above the fracture site into a fracture site and then advancing a dilator over the guide member to form the access path.

13. The method of claim 12, wherein the guide member comprises a k-wire or guide wire.

14. The method of claim 12, wherein the dilator comprises a series of sequential dilators.

15. The method of claim 11 wherein the fixation device is made at least partially from a bioabsorbable metallic material or metallic alloy.

16. The method of claim 15, wherein bioabsorbable metallic material or metallic alloy comprises magnesium, a magnesium alloy, zinc and/or a zinc alloy.

17. The method of claim 11, wherein the flange is coupled to or integral with the bridge.

18. The method of claim 11, wherein the first anchor includes the flange.

19. The method of claim 11, wherein the securing step comprises urging the first and second anchors toward each other.

* * * * *